United States Patent
Wilson et al.

(10) Patent No.: US 9,289,297 B2
(45) Date of Patent: Mar. 22, 2016

(54) MITRAL VALVE SPACER AND SYSTEM AND METHOD FOR IMPLANTING THE SAME

(71) Applicant: Cardiosolutions, Inc., Stoughton, MA (US)

(72) Inventors: Jonathan E. Wilson, Mattapoisett, MA (US); Glenn Kanner, Duxbury, MA (US); Eric Conley, South Berwick, ME (US); Amos Cruz, Wrentham, MA (US)

(73) Assignee: CardioSolutions, Inc., West Bridgewater, MA (US)

( * ) Notice: Subject to any disclaimer, the term of this patent is extended or adjusted under 35 U.S.C. 154(b) by 205 days.

(21) Appl. No.: 13/840,252

(22) Filed: Mar. 15, 2013

(65) Prior Publication Data

US 2014/0277405 A1     Sep. 18, 2014

(51) Int. Cl.
*A61F 2/24*     (2006.01)
*A61B 17/34*    (2006.01)
*A61B 17/00*    (2006.01)

(52) U.S. Cl.
CPC ........... *A61F 2/2466* (2013.01); *A61B 17/3478* (2013.01); *A61F 2/246* (2013.01); *A61B 2017/00243* (2013.01); *A61B 2017/00318* (2013.01); *A61B 2017/00323* (2013.01); *A61B 2017/00349* (2013.01); *A61F 2220/0016* (2013.01); *A61F 2250/0003* (2013.01)

(58) Field of Classification Search
USPC ......................................................... 606/195
See application file for complete search history.

(56) References Cited

U.S. PATENT DOCUMENTS

| | | | |
|---|---|---|---|
| 2,549,731 | A | 4/1951 | Wattley |
| 2,625,967 | A | 1/1953 | Stull |
| 3,197,788 | A | 8/1965 | Segger |
| 3,445,916 | A | 5/1969 | Schulte |
| 3,551,913 | A | 1/1971 | Shiley et al. |
| 3,586,029 | A | 6/1971 | Evers |
| 3,589,392 | A | 6/1971 | Meyer |
| 3,671,979 | A | 6/1972 | Moulopoulos |
| 3,689,942 | A | 9/1972 | Rapp |

(Continued)

FOREIGN PATENT DOCUMENTS

| | | |
|---|---|---|
| EP | 0125393 | 11/1984 |
| EP | 1323438 | 2/2003 |

(Continued)

OTHER PUBLICATIONS

PCT Notification of Transmittal of the International Search Report and the Written Opinion of the International Searching Authority, or the Declaration, PCT/US2014/027270, mailed Sep. 24, 2014 (8 pages).

(Continued)

*Primary Examiner* — Tuan V Nguyen
(74) *Attorney, Agent, or Firm* — Reza Mollaaghababa; Thomas Engellenner; Pepper Hamilton LLP

(57) ABSTRACT

A trans-femoral implant includes an anchor assembly and a balloon assembly configured to be separately delivered to an implant site within a heart. Once delivered, the anchor assembly and balloon assembly may be coupled to form an implant within the heart. The balloon anchor may include a fluid inflatable balloon that may be selectively filled via a balloon filling valve. The balloon assembly may further include a latching mechanism that may couple with a distal end of the anchor assembly, such that the length of the implant may be adjusted within the heart.

10 Claims, 43 Drawing Sheets

(56) References Cited

U.S. PATENT DOCUMENTS

| | | |
|---|---|---|
| 3,714,671 A | 2/1973 | Edwards et al. |
| 3,739,402 A | 6/1973 | Cooley et al. |
| 3,983,581 A | 10/1976 | Angell et al. |
| 4,079,468 A | 3/1978 | Liotta et al. |
| 4,084,268 A | 4/1978 | Ionescu et al. |
| 4,259,753 A | 4/1981 | Liotta et al. |
| 4,291,420 A | 9/1981 | Reul |
| 4,297,749 A | 11/1981 | Davis et al. |
| 4,439,185 A | 3/1984 | Lundquist |
| 4,535,757 A | 8/1985 | Webster, Jr. |
| 4,597,767 A | 7/1986 | Lenkei |
| 4,865,030 A | 9/1989 | Polyak |
| 4,960,424 A | 10/1990 | Grooters |
| 5,002,067 A | 3/1991 | Berthelsen et al. |
| 5,059,176 A * | 10/1991 | Winters .................... 604/99.04 |
| 5,217,484 A | 6/1993 | Marks |
| 5,222,973 A | 6/1993 | Sharpe et al. |
| 5,261,916 A | 11/1993 | Engelson |
| 5,304,195 A | 4/1994 | Twyford, Jr. et al. |
| 5,308,357 A | 5/1994 | Lichtman |
| 5,318,589 A | 6/1994 | Lichtman |
| 5,350,397 A | 9/1994 | Palermo et al. |
| 5,397,351 A | 3/1995 | Pavcnik et al. |
| 5,411,552 A | 5/1995 | Andersen et al. |
| 5,415,667 A | 5/1995 | Frater |
| 5,462,527 A | 10/1995 | Stevens-Wright et al. |
| 5,509,428 A | 4/1996 | Dunlop |
| 5,554,185 A | 9/1996 | Block et al. |
| 5,582,607 A | 12/1996 | Lackman |
| 5,611,800 A | 3/1997 | Davis et al. |
| 5,634,936 A | 6/1997 | Linden et al. |
| 5,638,827 A | 6/1997 | Palmer et al. |
| 5,649,949 A | 7/1997 | Wallace et al. |
| 5,653,712 A | 8/1997 | Stern |
| 5,665,100 A | 9/1997 | Yoon |
| 5,776,075 A | 7/1998 | Palmer |
| 5,792,179 A | 8/1998 | Sideris |
| 5,797,958 A | 8/1998 | Yoon |
| 5,814,098 A | 9/1998 | Hinnenkamp et al. |
| 5,840,081 A | 11/1998 | Andersen et al. |
| 5,891,130 A | 4/1999 | Palermo et al. |
| 5,895,391 A | 4/1999 | Farnholtz |
| 5,928,224 A | 7/1999 | Laufer |
| 5,957,865 A | 9/1999 | Backman et al. |
| 5,957,949 A | 9/1999 | Leonhardt et al. |
| 5,989,242 A | 11/1999 | Saadat et al. |
| 5,993,474 A | 11/1999 | Ouchi |
| 6,090,096 A | 7/2000 | St. Goar et al. |
| 6,152,144 A | 11/2000 | Lesh et al. |
| 6,168,614 B1 | 1/2001 | Andersen et al. |
| 6,183,512 B1 | 2/2001 | Howanec et al. |
| 6,190,373 B1 | 2/2001 | Palermo et al. |
| 6,217,610 B1 | 4/2001 | Carpentier et al. |
| 6,283,127 B1 | 9/2001 | Sterman et al. |
| 6,283,995 B1 | 9/2001 | Moe et al. |
| 6,287,339 B1 | 9/2001 | Vazquez et al. |
| 6,332,893 B1 | 12/2001 | Mortier et al. |
| 6,358,277 B1 | 3/2002 | Duran |
| 6,415,693 B1 | 7/2002 | Simon et al. |
| 6,416,549 B1 | 7/2002 | Chinn et al. |
| 6,419,695 B1 | 7/2002 | Gabbay |
| 6,440,132 B1 | 8/2002 | Jackson |
| 6,454,798 B1 | 9/2002 | Moe |
| 6,461,382 B1 | 10/2002 | Cao |
| 6,482,228 B1 | 11/2002 | Norred |
| 6,508,825 B1 | 1/2003 | Selmon et al. |
| 6,517,515 B1 | 2/2003 | Eidenschink |
| 6,592,606 B2 | 7/2003 | Huter et al. |
| 6,629,534 B1 | 10/2003 | St Goar et al. |
| 6,652,578 B2 | 11/2003 | Bailey et al. |
| 6,673,100 B2 | 1/2004 | Diaz et al. |
| 6,682,559 B2 | 1/2004 | Myers et al. |
| 6,695,866 B1 | 2/2004 | Kuehn et al. |
| 6,746,404 B2 | 6/2004 | Schwartz |
| 6,764,510 B2 | 7/2004 | Vidlund et al. |
| 6,767,362 B2 | 7/2004 | Schreck |
| 6,769,434 B2 | 8/2004 | Liddicoat et al. |
| 6,805,711 B2 | 10/2004 | Quijano et al. |
| 6,821,297 B2 | 11/2004 | Snyders |
| 6,830,584 B1 | 12/2004 | Sequin |
| 6,830,585 B1 | 12/2004 | Artof et al. |
| 6,849,081 B2 | 2/2005 | Sepetka et al. |
| 6,869,444 B2 | 3/2005 | Gabbay |
| 6,896,700 B2 | 5/2005 | Lu et al. |
| 6,911,043 B2 | 6/2005 | Myers et al. |
| 6,964,684 B2 | 11/2005 | Ortiz et al. |
| 6,971,998 B2 | 12/2005 | Rosenman et al. |
| 6,974,476 B2 | 12/2005 | McGuckin, Jr. et al. |
| 6,976,950 B2 | 12/2005 | Connors et al. |
| 7,018,406 B2 | 3/2006 | Sequin et al. |
| 7,056,286 B2 | 6/2006 | Ravenscroft et al. |
| 7,070,618 B2 | 7/2006 | Streeter |
| 7,077,862 B2 | 7/2006 | Vidlund et al. |
| 7,101,395 B2 | 9/2006 | Tremulis et al. |
| 7,112,219 B2 | 9/2006 | Vidlund et al. |
| 7,160,322 B2 | 1/2007 | Gabbay |
| 7,189,199 B2 | 3/2007 | McCarthy et al. |
| 7,247,134 B2 | 7/2007 | Vidlund et al. |
| 7,335,213 B1 | 2/2008 | Hyde et al. |
| 7,344,553 B2 | 3/2008 | Opolski et al. |
| 7,374,572 B2 | 5/2008 | Gabbay |
| 7,381,210 B2 | 6/2008 | Zarbatany et al. |
| 7,404,824 B1 | 7/2008 | Webler et al. |
| 7,657,326 B2 | 2/2010 | Bodner et al. |
| 7,678,145 B2 | 3/2010 | Vidlund et al. |
| 7,704,268 B2 | 4/2010 | Chanduszko |
| 7,713,282 B2 * | 5/2010 | Frazier et al. .................. 606/200 |
| 7,753,949 B2 | 7/2010 | Lamphere et al. |
| 7,785,366 B2 | 8/2010 | Maurer et al. |
| 7,927,370 B2 | 4/2011 | Webler et al. |
| 7,942,928 B2 | 5/2011 | Webler et al. |
| 7,963,973 B2 | 6/2011 | Nguyen et al. |
| 8,092,525 B2 | 1/2012 | Eliasen et al. |
| 8,118,822 B2 | 2/2012 | Schaller et al. |
| 8,216,302 B2 | 7/2012 | Wilson et al. |
| 8,486,136 B2 | 7/2013 | Maurer et al. |
| 8,506,623 B2 | 8/2013 | Wilson et al. |
| 2001/0007956 A1 | 7/2001 | Letac et al. |
| 2001/0010017 A1 | 7/2001 | Cribier et al. |
| 2001/0018611 A1 | 8/2001 | Solem et al. |
| 2002/0029080 A1 | 3/2002 | Mortier et al. |
| 2002/0032480 A1 | 3/2002 | Spence et al. |
| 2002/0042651 A1 | 4/2002 | Liddicoat et al. |
| 2002/0058995 A1 | 5/2002 | Stevens |
| 2002/0077566 A1 | 6/2002 | Laroya et al. |
| 2002/0081553 A1 | 6/2002 | Tramonte |
| 2002/0169377 A1 | 11/2002 | Khairkhahan et al. |
| 2002/0169502 A1 | 11/2002 | Mathis |
| 2002/0183838 A1 | 12/2002 | Liddicoat et al. |
| 2002/0188170 A1 | 12/2002 | Santamore et al. |
| 2003/0033009 A1 | 2/2003 | Gabbay |
| 2003/0040792 A1 | 2/2003 | Gabbay |
| 2003/0105519 A1 | 6/2003 | Fasol et al. |
| 2003/0120264 A1 | 6/2003 | Lattouf |
| 2003/0130731 A1 | 7/2003 | Vidlund et al. |
| 2003/0139751 A1 | 7/2003 | Evans et al. |
| 2003/0144574 A1 | 7/2003 | Heilman et al. |
| 2003/0181945 A1 | 9/2003 | Opolski et al. |
| 2003/0199975 A1 | 10/2003 | Gabbay |
| 2003/0208203 A1 | 11/2003 | Lim et al. |
| 2003/0212453 A1 | 11/2003 | Mathis et al. |
| 2004/0034366 A1 | 2/2004 | van der Burg et al. |
| 2004/0044402 A1 | 3/2004 | Jung et al. |
| 2004/0088047 A1 | 5/2004 | Spence et al. |
| 2004/0106989 A1 | 6/2004 | Wilson et al. |
| 2004/0122512 A1 | 6/2004 | Navia et al. |
| 2004/0127981 A1 | 7/2004 | Rahdert et al. |
| 2004/0127983 A1 | 7/2004 | Mortier et al. |
| 2004/0148020 A1 | 7/2004 | Vidlund et al. |
| 2004/0181256 A1 | 9/2004 | Glaser |
| 2004/0210304 A1 | 10/2004 | Sequin et al. |
| 2004/0210307 A1 | 10/2004 | Khairkhahan |
| 2004/0225353 A1 | 11/2004 | McGuckin, Jr. et al. |
| 2004/0225354 A1 | 11/2004 | Allen et al. |

(56) References Cited

U.S. PATENT DOCUMENTS

| | | |
|---|---|---|
| 2004/0243229 A1 | 12/2004 | Vidlund et al. |
| 2004/0260322 A1 | 12/2004 | Rudko et al. |
| 2005/0021056 A1 | 1/2005 | St. Goar et al. |
| 2005/0027337 A1 | 2/2005 | Rudko et al. |
| 2005/0033446 A1 | 2/2005 | Deem et al. |
| 2005/0038508 A1 | 2/2005 | Gabbay |
| 2005/0038509 A1 | 2/2005 | Ashe |
| 2005/0065591 A1 | 3/2005 | Moberg et al. |
| 2005/0070999 A1 | 3/2005 | Spence |
| 2005/0075727 A1 | 4/2005 | Wheatley |
| 2005/0090824 A1 | 4/2005 | Shluzas et al. |
| 2005/0131451 A1 | 6/2005 | Kleshinski et al. |
| 2005/0149182 A1 | 7/2005 | Alferness et al. |
| 2005/0159810 A1 | 7/2005 | Filsoufi |
| 2005/0222488 A1 | 10/2005 | Chang et al. |
| 2005/0288786 A1 | 12/2005 | Chanduszko |
| 2006/0020335 A1 | 1/2006 | Kowalsky et al. |
| 2006/0025855 A1 | 2/2006 | Lashinski et al. |
| 2006/0058871 A1 | 3/2006 | Zakay et al. |
| 2006/0084943 A1 | 4/2006 | Rosenman et al. |
| 2006/0129025 A1 | 6/2006 | Levine et al. |
| 2006/0149368 A1 | 7/2006 | Spence |
| 2006/0155326 A1 | 7/2006 | Aranyi |
| 2006/0178700 A1 | 8/2006 | Quinn |
| 2006/0195012 A1 | 8/2006 | Mortier et al. |
| 2006/0195185 A1 | 8/2006 | Lane et al. |
| 2006/0199995 A1 | 9/2006 | Vijay |
| 2006/0229708 A1 | 10/2006 | Powell et al. |
| 2006/0241745 A1 | 10/2006 | Solem |
| 2006/0253072 A1 | 11/2006 | Pai et al. |
| 2006/0293698 A1 | 12/2006 | Douk |
| 2007/0016286 A1 | 1/2007 | Herrmann et al. |
| 2007/0049980 A1 | 3/2007 | Zielinski et al. |
| 2007/0093890 A1 | 4/2007 | Eliasen et al. |
| 2007/0118151 A1 | 5/2007 | Davidson |
| 2007/0149995 A1 | 6/2007 | Quinn et al. |
| 2007/0167981 A1 | 7/2007 | Opolski et al. |
| 2007/0185571 A1 | 8/2007 | Kapadia et al. |
| 2007/0198050 A1 | 8/2007 | Ravenscroft et al. |
| 2007/0198082 A1 | 8/2007 | Kapadia et al. |
| 2007/0213578 A1 | 9/2007 | Khairkhahan et al. |
| 2007/0232981 A1 | 10/2007 | Ravenscroft et al. |
| 2007/0232992 A1 | 10/2007 | Kutsko et al. |
| 2007/0239154 A1 | 10/2007 | Shaolian et al. |
| 2007/0255399 A1 | 11/2007 | Eliasen et al. |
| 2007/0265700 A1 | 11/2007 | Eliasen et al. |
| 2007/0282429 A1 | 12/2007 | Hauser et al. |
| 2007/0293943 A1 | 12/2007 | Quinn |
| 2008/0125860 A1 | 5/2008 | Webler et al. |
| 2008/0125861 A1 | 5/2008 | Webler et al. |
| 2008/0183105 A1 | 7/2008 | Greenhalgh et al. |
| 2008/0195200 A1 | 8/2008 | Vidlund et al. |
| 2008/0288061 A1 | 11/2008 | Maurer et al. |
| 2009/0043382 A1 | 2/2009 | Maurer et al. |
| 2009/0048668 A1 | 2/2009 | Wilson et al. |
| 2009/0105814 A1 | 4/2009 | Groothuis et al. |
| 2009/0131849 A1 | 5/2009 | Maurer et al. |
| 2009/0131880 A1 | 5/2009 | Speziali et al. |
| 2009/0132033 A1 | 5/2009 | Maurer et al. |
| 2009/0163934 A1 | 6/2009 | Raschdorf, Jr. et al. |
| 2009/0240326 A1 | 9/2009 | Wilson et al. |
| 2010/0022948 A1 | 1/2010 | Wilson et al. |
| 2010/0324668 A1 | 12/2010 | Maurer et al. |
| 2012/0143320 A1 | 6/2012 | Eliassen et al. |
| 2015/0127097 A1 | 5/2015 | Neumann |

FOREIGN PATENT DOCUMENTS

| | | |
|---|---|---|
| GB | 1264472 | 2/1972 |
| GB | 1268484 | 3/1972 |
| GB | 1388064 | 3/1975 |
| WO | 03/049619 | 6/2003 |
| WO | WO2006032051 | 3/2006 |
| WO | 2006/064490 | 6/2006 |
| WO | 2006091597 | 8/2006 |
| WO | 2006/111391 | 10/2006 |
| WO | 2006127509 | 11/2006 |
| WO | 2007064810 | 6/2007 |
| WO | 2007078772 | 7/2007 |
| WO | 2007100409 | 9/2007 |
| WO | 2007/140470 | 12/2007 |
| WO | 2008079828 | 7/2008 |
| WO | 2009053952 | 4/2009 |

OTHER PUBLICATIONS

Harper, Evalve Announces Enrollment Completion of the Everest Randomized Study, http://www.evalveinc.com/europe/press/17.html, downloaded Feb. 24, 2009, 1-3.

Harper, Two-Year Follow-Up Data Demonstrates Preservation of Adequate Mitral Valve Area in Patients Treated with the MitraClip®-system, http://www.evalveinc.com/europe/press/21.html, downloaded Feb. 24, 2009, 1-3.

Hung et al., 3D Echocardiography: A Review of the Current Status and Future Directions, ASE Position Paper, Journal of the American Society of Echocardiography, Mar. 2007, 213-233.

Hung et al., Mechanism of Dynamic Regurgitant Orifice Area Variation of Functional Mitral Regurgitation-Physiologic Insights From the Proximal Flow Convergence Technique, Journal of the American College of Cardiology, Feb. 1999, vol. 33, No. 2, 538-545.

Hung et al., A Novel Approach for Reducing Ischemic Mitral Regurgitation by Injection of a Polymer of Reverse Remodel and Reposition Displaced Papillary Muscles, Circulation—Journal of the American Heart Association, Sep. 30, 2008, Downloaded from circ.ahajournals.org at National Insthealth Lib on Feb. 25, 2009, S262-S269.

Hytowitz, First U.S. Patients Enrolled in the Realism Continued Access Study, evalve, http://www.evalveinc.com/europe/press/22/html, downloaded Feb. 24, 2009, 2 pages.

International Search Report and Written Opinion dated Feb. 25, 2009 issued in PCT Application No. PCT/US08/83570, 13 pages.

International Search Report and Written Opinion dated Apr. 2, 2009 issued in PCT Application No. PCT/US08/83574, 8 pages.

Jilaihawi et al., Percutaneous Aortic Valve Replacement in Patients with Challenging Aortoiliofemoral Access, Catheterization and Cardiovascular Interventions, 2008, vol. 72, 885-890.

Jovin et al., Atrial Fibrillation and Mitral Valve Repair, Pace, Aug. 2008, vol. 31, 1057-1063.

Kahlert et al., Direct Assessment of Size and Shape of Noncircular Vena Contracta Area in Functional Versus Organic Mitral Regurgitation Using Real-Time Three-Dimensional Echocardiography, Valvular Heart Disease, Journal of the American Society of Echocardiography, Aug. 2008, vol. 21, No. 8, 912-921.

Kempfert et al, Minimally invasive off-pump valve-in-a-valve implantation: the atrial transcatheter approach for re-operative mitral valve replacement, European Heart Journal, 2008, vol. 29, 2382-2387.

Kerensky, Complications of Cardiac Catheterization and Strategies to Reduce Risks, Diagnostic and Therapeutic Cardiac Catheterization—Third Edition—Chapter 8, 1998, 17 pages.

Kodali et al., Transcatheter Valve Repair and Replacement, Downloaded from arjournals.annualreviews.org by National Institute of Health Library on Feb. 25, 2009, 14 pages.

Kwan et al., Geometric Differences of the Mitral Apparatus Between Ischemic and Dilated Cardiomyopathy With Significant Mitral Regurgitation—Real-Time Three—Dimensional Echocardiography Study, Circulation, Mar. 4, 2003, 1135-1140.

Leung et al, Percutaneous Mitral Valve Repair—An overview of the current devices and techniques, Coronory/Cardiac Interventions—Endovascular Today, Oct. 2006, 26-33.

Levine et al., Mechanistic Insights into Functional Mitral Regurgitation, Valvular Heart Disease, 2009, 125-129.

Little et al., Three-Dimensional Ultrasound Imaging Model of Mitral Valve Regurgitation: Design and Evaluation, Ultrasound in Medicine and Biology, 2008, vol. 34, No. 4, 647-654.

(56) References Cited

OTHER PUBLICATIONS

Llaneras et al., Large Animal Model of Ischemic Mitral Regurgitation, The Society of Thoracic Surgeons—Ischemic Mitral Insufficiency, 1994, vol. 57, 432-439.
Magne et al., Ischemic Mitral Regurgitation: A Complex Multifaceted Disease, Cardiology, 2009, vol. 112, 244-259.
McClure et al., Early and late outcomes in minimally invasive mitral valve repair: An eleven-year experience in 707 patients, Acquired Cardiovascular Disease, The Journal of Thoracic and Cardiovascular Surgery, Jan. 2009, vol. 137, No. 1, 70-75.
Modi et al., Minimally invasive mitral valve surgery: a systematic review and meta-analysis, European Journal of Cardio-Thoracic Surgery, 2008, vol. 34, 943-952.
Myers, Jr., et al., Color Doppler Velocity Accuracy Proximal to Regurgitant Orifices: Influence of Orifice Aspect Ratio, Ultrasound in Medicine and Biology, 1999, vol. 25, No. 5, 771-792.
Ning et al., Live three-dimensional transesophageal echocardiography in mitral valve surgery, Chinese Medical Journal, 2008, vol. 121, No. 20, 2037-2041.
Nötzold et al., Microemboli in aortic valve replacement, Future Drugs Ltd, Expert Rev. Cardiovasc. Ther., vol. 4, No. 6, 2006, 853-859.
Onundarson et al., Warfarin anticoagulation intensity in specialist-based and in computer-assisted dosing practice, International Journal of Laboratory Hematology, 2008, vol. 30, 382-389.
Otsuji et al., Insights From Three-Dimensional Echocardiography Into the Mechanism of Functional Mitral Regurgitation—Direct In Vivo Demonstration of Altered Leaflet Tethering Geometry, Circulation, Sep. 16, 1997, vol. 96, No. 6, 1999-2008.
Fukuda et al., Maintenance of Geometric Alterations Associated with Percutaneous Mitral Valve Repair: Real-Time Three-Dimensional Echocardiographic Assessment in an Ovine Model, J. Heart Valve Dis, May 2008, vol. 17, No. 3, 276-282.
Pai et al., Effect of Atrial Fibrillation on the Dynamics of Mitral Annular Area, J. Heart Valve Dis., Jan. 2003, vol. 12, No. 1, 31-37.
Palacios et al., Safety and Feasibility of Acute Percutaneous Septal Sinus Shortening: First-In-Human Experience, Catheterization and Cardiovascular Interventions, 2007, vol. 69, 513-518.
Paniagua et al., First Human Case of Retrograde Transcatheter Implantation of an Aortic Valve Prosthesis, Texas Heart Institute Journal, Transcatheter Aortic Valve Prosthesis, 2005, vol. 32, No. 3, 393-398.
Rodés-Cabau et al., Feasibility and Initial Results of Percutaneous Aortic Valve Implantation Including Selection of the Transfemoral or Transapical Approach in Patients With Severe Aortic Stenosis, The American Journal of Cardiology, 2008, 1240-1246.
Satpathy et al., Delayed Defibrillator Lead Perforation: An Increasing Phenomenon, Pace, Jan. 2008, vol. 31, 10-12.
Schofer, Percutaneous MVR: Clinical Evaluation—The Carillon Experience, EuroPCR 2007, Barcelona, Spain, May 22-25, 2007, 35 pages.
Schwammenthal et al., Dynamics of Mitral Regurgitant Flow and Orifice Area—Physiologic Application of the Proximal Flow Convergence Method: Clinical Data and Experimental Testing, Circulation, Jul. 1994, vol. 90, No. 1, 307-322.
Spencer, Viacor, Inc. Announces First Patient Treated in PTOLEMY-2 Study, http://www.viacorinc.com/viacor_news.html, Nov. 14, 2008, downloaded Feb. 24, 2009, 2 pages.
Sterliński et al., Subacute cardiac perforations associated with active fixation leads, Clinical Research Leads and Lead Extraction, Europace, 2009, vol. 11, 206-212.
Turakhia et al., Rates and severity of perforation from implantable cardioverter-defibrillator leads: A 4-year study, J Interv Card Electrophysiol, 2009, vol. 24, 47-52.
Vahanian, The Cardiologist's Perspective on the Future of Percutaneous Mitral Valve Repair, Euro PCR07, May 22-25, 2007, 53 pages.
Vahanian, Coronary Sinus and Direct Annuloplasty Percutaneous Mitral Valve Repair, Innovations in Cardiovascular Interventions, Dec. 7-9, 2008, Tel-Aviv, Israel, 45 pages.
Vahanian, Edwards MONARC system—Evolution Interim Results, 31 pages.
Vahanian, Overview on Percutaneous Mitral Valve Technology, Euro PCR07, Transcatheter Valve Symposium, Barcelona, May 22-25, 2007, 29 pages.
Van Gelder et al., Diagnosis and Management of Inadvertently Placed Pacing and ICD Leads in the Left Ventricle: A Multicenter Experience and Review of the Literature, Pace, May 2000, vol. 23, 877-883.
Vranckx et al., The TandemHeart®, percutaneous transseptal left ventricular assist device: a safeguard in high-risk percutaneous coronary interventions. The six-year Rotterdam experience, Clinical research EuroInterv., 2008, vol. 4, 331-337.
Wolf et al., Solid and gaseous cerebral micorembolization after biologic and mechanical aortic valve replacement: Investigation with multirange and multifrequency transcranial Doppler ultrasound, The Journal of Thoracic and Cardiovascular Surgery, Mar. 2008, vol. 135, No. 3, 512-520.
Xiangming et al., In Vivo Characterization of Attachment Safety Between Cardiac Pacing Lead and Canine Heart Muscle*, Acta Mechanica Solida Sinica, Sep. 2007, vol. 20, No. 3, 189-197.
Yamaura et al., Geometrical Demonstration and Three-Dimensional Quantitative Analysis of the Mitral Valve With Real-Time Three-Dimensional Echocardiography: Novel Anatomical Image Creation System, J Echocardiogr, 2004, vol. 2, No. 4, 99-104.
Yosefy et al., Proximal Flow Convergence Region as Assessed by Real-time 3-Dimensional Echocardiography: Challenging the Hemispheric Assumption, Journal of the American Society of Echocardiography, Apr. 2007, vol., No. 4, 389-396.
U.S. Office Action dated Jul. 8, 2009 issued in U.S. Appl. No. 11/258,828, 7 pages.
International Search Report and Written Opinion dated Aug. 11, 2009 issued in PCT Application No. PCT/US2009/046995, 11 pages.
U.S. Office Action dated Sep. 29, 2009 issued in U.S. Appl. No. 12/209,686, 9 pages.
U.S. Office Action dated Dec. 15, 2009 issued in U.S. Appl. No. 11/258,828, 12 pages.
U.S. Office Action dated Jan. 8, 2010 issued in U.S. Appl. No. 11/748,147, 63 pages.
U.S. Office Action dated Jan. 14, 2010 issued in U.S. Appl. No. 11/940,674, 59 pages.
U.S. Office Action dated Jan. 25, 2010 issued in U.S. Appl. No. 11/748,121, 9 pages.
U.S. Office Action dated Feb. 4, 2010 issued in U.S. Appl. No. 11/748,138, 58 pages.
U.S. Office Action dated Jun. 2, 2010 issued in U.S. Appl. No. 12/209,686, 15 pages.
U.S. Office Action dated Jun. 28, 2010 issued in U.S. Appl. No. 11/258,828, 14 pages.
Notice of Allowance dated Jul. 1, 2010 issued in U.S. Appl. No. 11/940,674, 6 pages.
International Search Report and Written Opinion dated Jul. 6, 2010 issued in PCT Patent Application No. PCT/US2010/032764, 9 pages.
U.S. Office Action dated Jul. 20, 2010 issued in U.S. Appl. No. 11/748,147, 15 pages.
Ryhänen et al., In vivo biocompatibility evaluation of nickel-titanium shape memory metal alloy: Muscle and perineural tissue responses and encapsule membrane thickness, Muscle and Perineural Tissue Response to Nitinol, Jan. 19, 1998, pp. 481-488.
U.S. Office Action dated Aug. 30, 2010 issued in U.S. Appl. No. 11/748,138, 9 pages.
U.S. Office Action dated Aug. 31, 2010 issued in U.S. Appl. No. 11/748,121, 11 pages.
International Search Report and Written Opinion dated Sep. 21, 2010 issued in PCT Patent Application No. PCT/US2010/043360, 9 pages.
Extended European search report dated Nov. 30, 2010 issued in European Patent Application No. 08850467.5, 6 pages.
Extended European search report dated Nov. 30, 2010 issued in European Patent Application No. 08755418.4, 7 pages.
Extended European search report dated Nov. 30, 2010 issued in European Patent Application No. 08849442.2, 6 pages.
Extended European Search Report dated Dec. 1, 2010 issued in European Patent Application No. 08755426.7, 6 pages.

(56) References Cited

OTHER PUBLICATIONS

Extended European Search Report dated Dec. 14, 2010 issued in European Patent Application No. 06816336.9, 7 pages.
U.S. Office Action dated Mar. 21, 2011 issued in U.S. Appl. No. 11/258,828, 22 pages.
U.S. Office Action dated Mar. 29, 2011 issued in U.S. Appl. No. 11/748,121, 14 pages.
U.S. Office Action dated Apr. 4, 2011 issued in U.S. Appl. No. 11/940,724, 65 pages.
European Examination Report dated Aug. 4, 2011 issued in European Patent No. 06 816 336.9, 3 pages.
U.S. Office Action dated Aug. 29, 2011 issued in U.S. Appl. No. 11/940,694, 11 pages.
European Examination Report dated Aug. 11, 2011 issued in European Patent No. 08 755 418.4, 3 pages.
Notice of Allowance dated Oct. 31, 2011 issued in U.S. Appl. No. 11/258,828, 10 pages.
Preliminary Report on Patentability dated Nov. 1, 2011 issued in PCT Patent Application No. PCT/US2010/032764, 4 pages.
U.S. Office Action dated Nov. 3, 2011 issued in U.S. Appl. No. 12/872,228, 8 pages.
Notice of Allowance dated Dec. 14, 2011 issued in U.S. Appl. No. 12/431,399, 12 pages.
U.S. Office Action dated Dec. 21, 2011, issued in U.S. Appl. No. 11/748,121, 9 pages.
U.S. Office Action dated Jan. 18, 2012 issued in U.S. Appl. No. 11/940,724, 10 pages.
International Preliminary Report on Patentability dated Jan. 31, 2012 issued in PCT Patent Application No. PCT/US2010/043360, 7 pages.
U.S. Office Action dated Feb. 15, 2012 issued in U.S. Appl. No. 11/940,694, 9 pages.
U.S. Notice of Allowance dated Mar. 8, 2012 issued in U.S. Appl. No. 12/872,228, 7 pages.
U.S. Office Action dated Jun. 20, 2012 issued in U.S. Appl. No. 11/940,694, 9 pages.
U.S. Office Action dated Jun. 21, 2012 issued in U.S. Appl. No. 11/748,147, 29 pages.
Notice of Allowance dated Jul. 20, 2012 issued in U.S. Appl. No. 11/748,121, 10 pages.
U.S. Office Action dated Sep. 19, 2012 issued in U.S. Appl. No. 12/510,929, 10 pages.
U.S. Office Action dated Oct. 9, 2012, issued in U.S. Appl. No. 12/872,228, 7 pages.
U.S. Notice of Allowance dated Nov. 21, 2012, issued in U.S. Appl. No. 11/748,121, 8 pages.
Canadian Office Action dated Sep. 18, 2012 issued in Canadian Patent Application No. 2,627,517, 2 pages.
Intent to Grant dated Jan. 2, 2013 issued in European Patent Application No. 06816336.9, 7 pages.
Notice of Allowance dated Jan. 9, 2013 issued in U.S. Appl. No. 11/748,121, 7 pages.
Bailey et al, "Surgical Repair of Mitral Insufficiency" Feb. 1951 (pp. 125-137).
Bailey et al, "Closed Intracardiac Tactile Surgery" Jul. 1952 (pp. 1-24).
Bailey et al., "The Surgical Correction of Mitral Insufficiency by the Use of Pericardial Grafts" Dec. 1954 (pp. 551-627).
Benichoux et al., "A Method of Surgical Correction of Mitral Insufficiency" 1955 (pp. 148-158).
Blalock, "A Consideration of Some of the Problems in Cardiovascular Surgery" Jun. 1951 (pp. 543-571).
Borrie, "Mitral Insufficiency: Experimental Circular Suture Around the Artioventricular Ring" 1955 (pp. 687-697).
Carter et al. "Surgical Treatment of Mitral Insufficiency" 1953 (pp. 574-583).
European Search Report dated Jul. 12, 1984 cited in EP0125393.
"French catheter scale chart" http://en.wikipedia.org/wiki/French_catheter_scale_chart, Dec. 20, 2006, 1 page.

"General Physical Properties of PVA Sponge (values are not guaranteed)", Ceiba Technologies, http://www.ceibatech.com/PVASpongeDate.htm, Dec. 20, 2006 3 pages.
Glenn et al., "The Implantation of a Vascularized Graft in the Chambers of the Heart" 1954 (pp. 5-11).
Glenn et al, "The Surgical Treatment of Mitral Insufficiency: the Fate of Vascularized Transchamber Intracardiac Graft" Apr. 1955 (pp. 510-518).
Glenn et al., "The Surgical Treatment of Mitral Insufficiency with Particular Reference to the Application of a Vertically Suspended Graft" Jul. 1956 (pp. 59-77).
Glover, et al., "The Fate of Intracardiac Pericardial Grafts as Applied to the Closure of Septal Defects and to the Relief of Mitral Insufficiency" 1952 (pp. 178-185).
Harken et al., "The Surgical Correction of Mitral Insufficienty" Surgical Forum 1954 (pp. 4-7).
Harken et al, "The Surgical Correction of Mitral Insufficiency" The Journal of Thoracic Surgery 1954 (pp. 604-627).
Henderson et al., "The Surgical Treatment of Mitral Insufficiency" Jun. 1953 (pp. 858-868).
International Search and Written Opinion mailed May 11, 2007 filed in corresponding PCT patent application PCT/US06/39011(8 pages).
Johns et al., Mitral Insufficiency: the Experimental Use of a Mobile Polyvinyl sponge Prosthesis: Sep. 1954 (pp. 335-341).
Moore, et al., "Unsuitability of Transventricular Autogenous Slings for Diminishing Valvular Insufficiency" Feb. 1953 (pp. 173-182).
"PVA Datasheet", www.sponge-pva.com/data.htm, Dec. 20, 2006, 2 pages.
"PVA Sponge W (wet) & D (dry)", Ceiba Technologies, http://www.ceibatech.com/PVASpongeW&D.htm, Dec. 20, 2007 5 pages.
Sakakibara, "A Surgical Approach to the Correction of Mitral Insufficiency" Aug. 1955 (pp. 196-203).
SPI-Chem™ Vinylec® (Formvar®) Resins, http://www.2spi.com/catalog/submat/formvar-resins.shtml, Dec. 20, 2006, 5 pages.
Trippel et al, "Reinforced Ivalon Sponge as an Aortic Prosthesis*", Annals of Surgery, Feb. 1960, vol. 151, No. 2, pp. 216-224.
"Vinylec® Resins", http://www.2spi.com/catalog/submat/vinylec-physical.html, Dec. 20, 2006, 1 page.
Matthews, Anatomy of the Heart, Definitions Cardiology Explained and Presented by Robert Matthews, MD, http://www.rjmatthewsmd.com/Definitions/anatomy_ofthe_heart.htm, printed Jul. 28, 2008, 265 pages.
Mullens, Vascular access, Cardiac Catheterization in Congenital Heart Disease; Pediatric and Adult, 2006, Chapter 4, pp. 115-117, 5 pages, Blackwell Futura, USA.
Mullens, Aortic valve dilation, Cardiac Catheterization in Congenital Heart Disease; Pediatric and Adult, 2006, Chapter 19, pp. 487-489, 5 pages, Blackwell Futura, USA.
Mullens, Foreign body removal, Cardiac Catheterization in Congenital Heart Disease; Pediatric and Adult, 2006, Chapter 12, pp. 350-377, 30 pages, Blackwell Futura, USA.
Mullens, Flow directed catheters ("floating" balloon catheters), Cardiac Catheterization in Congenital Heart Disease; Pediatric and Adult, 2006, Chapter 7, pp. 213-221, 9 pages, Blackwell Futura, USA.
Acar et al., AREVA: Multicenter Randomized Comparison of Low-Dose Versus Standard-Dose Anticoagulation in Patients With Mechanical Prosthetic Heart Valves, Circulation, Nov. 1, 1996, 2107-12, vol. 94, No. 9.
Acker et al., Mitral valve surgery in heart failure: Insights from the Acorn Clinical Trial, Surgery for Acquired Cardiovascular Disease, The Journal of Thoracic and Cardiovascular Surgery, Sep. 2006, 568-577.e4, vol. 132, No. 3.
Babaliaros et al., Emerging Applications for Transseptal Left Heart Catheterization—Old Techniques for New Procedures, Journal of the American College of Cardiology, Jun. 3, 2008, 2116-22, vol. 51, No. 22.
Kuck et al., Best of Structural Heart Disease Abstracts, TCT-124, The American Journal of Cardiology, Oct. 20-25, 2007, 58L.
Rinaldi et al., Best of Structural Heart Disease Abstracts, TCT-123, The American Journal of Cardiology, Oct. 20-25, 2007, 57L.
Siminiak et al., Best of Structural Heart Disease Abstracts, TCT-125, The American Journal of Cardiology, Oct. 20-25, 2007, 58L.

(56) References Cited

OTHER PUBLICATIONS

B-Lundqvist et al., Transseptal Left Heart Catheterization: A Review of 278 Studies, Clin. Cardiol., Jan. 1986, 21-26, vol. 9.
Bonow et al., ACC/AHA 2006 Guidelines for the Management of Patients With Valvular Heart Disease: Executive Summary, Circulation—Journal of the American Heart Association, Downloaded from circ.ahajournals.org, Jul. 31, 2008, 449-527.
Braunberger et al., Very Long-Term Results (More Than 20 Years) of Valve Repair With Carpentier's Techniques in Nonrheumatic Mitral Valve Insufficiency, Downloaded from circ.ahajournals.org, Aug. 26, 2008, I-8-I-11.
Bryan et al., Prospective randomized comparison of CarboMedics and St. Jude Medical bileaflet mechanical heart valve prostheses: Ten-year follow-up, The Journal of Thoracic and Cardiovascular Surgery, Mar. 2007, 614-622.e2, vol. 133, No. 3.
Burkhoff et al., A randomized multicenter clinical study to evaluate the safety and efficacy of the TandemHeart percutaneous ventricular assist device versus conventional therapy with intraaortic balloon pumping for treatment of cardiogenic shock, American Heart Journal, Sep. 2006, 469.e1-469.e8, vol. 152, No. 3.
Byrne et al., Percutaneous Mitral Annular Reduction Provides Continued Benefit in an Ovine Model of Dilated Cardiomyopathy, Downloaded from circ.ahajournals.org, Aug. 26, 2008, 3088-92.
Carpentier et al., Reconstructive surgery of mitral valve incompetence Ten-year appraisal, The Journal of Thoracic and Cardiovascular Surgery, Mar. 1980, 338-348, vol. 79, No. 3.
Casselman et al., Mitral Valve Surgery Can Now Routinely Be Performed Endoscopically, Downloaded from circ. ahajournals.org, Aug. 26, 2008, II-48 -II-54.
Cauchemez et al., High-Flow Perfusion of Sheaths for Prevention of Thromboembolic Complications During Complex Catheter Ablation in the Left Atrium, Journal of Cardiovascular Electrophysiology, Mar. 2004, 276-283, vol. 15, No. 3.
ClinicalTrials.gov, Aachen Safety and Efficacy of the Percutaneous Transvenous Mitral Annuloplasty Device to Reduce Mitral Regurgitation (PTOLEMY), http://clinicaltrials.gov/ct2/show/NCT00572091?term=mitral+regurgitation&rank=2, Aug. 25, 2008, 1-3.
ClinicalTrials.gov, Feasibility Study of a Percutaneous Mitral Valve Repair System., http://clinicaltrials.gov/ct2/show/NCT00209339?term=mitral+valve&rank=3, Aug. 25, 2008, 1-4.
ClinicalTrials.gov, Montreal Safety and Efficacy of the Percutaneous Transvenous Mitral Annuloplasty Device (PTOLEMY), http://clinicaltrials.gov/ct2/show/NCT00571610?term=mitral+regurgitation&rank=13, Aug. 25, 2008, 1-4.
ClinicalTrials.gov, Pivotal Study of a Percutaneous Mitral Valve Repair System, http://clinicaltrials.gov/ct2/show/NCT00209274?term=mitral+valve&rank=1, Aug. 25, 2008, 1-4.
ClinicalTrials.gov, RESTOR-MV: Randomized Evaluation of a Surgical Treatment for Off-Pump Repair of the Mitral Valve, http://clinicaltrials.gov/ct2/show/NCT00120276?term=myocor&rank=1, Aug. 25, 2008, 1-5.
ClinicalTrials.gov, Safety and Efficacy of the Percutaneous Transvenous Mitral Annuloplasty Device to Reduce Mitral Regurgitation (PTOLEMY), http://clinicaltrials.gov/ct2/show/NCT00568230?term=mitral+valve&rank=53, Aug. 25, 2008, 1-3.
ClinicalTrials.gov, VIVID—Valvular and Ventricular Improvement Via iCoapsys Delivery—Feasibility Study, http://clinicaltrials.gov/ct2/show/NCT00512005?term=mitral+valve&rank=12, Aug. 25, 2008, 1-4.
Crabtree et al., Recurrent Mitral Regurgitation and Risk Factors for Early and Late Mortality After Mitral Valve Repair for Functional Ischemic Mitral Regurgitation, The Society of Thoracic Surgeons, 2008, 1537-43, 85.
Criber et al., Early Experience With Percutaneous Transcatheter Implantation of Heart Valve Prosthesis for the Treatment of End-Stage Inoperable Patients With Calcific Aortic Stenosis, Journal of the American College of Cardiology, Feb. 18, 2004, 698-703, vol. 43, No. 4.

De Bonis et al., Similar long-term results of mitral valve repair for anterior compared with posterior leaflet prolapse, The Journal of Thoracic and Cardiovascular Surgery, Feb. 2006, 364-370, vol. 131, No. 2.
Deloche et al., Valve repair with Carpentier techniques the second decade, The Journal of Thoracic and Cardiovascular Surgery, Jun. 1990, 990-1002, vol. 99, No. 6.
De Simone et al., A clinical study of annular geometry and dynamics in patients with ischemic mitral regurgitation: new insights into asymmetrical ring annuloplasty, European Journal of Cardio-thoracic Surgery, 2006, 355-361, 29.
Detaint et al., Surgical Correction of Mitral Regurgitation in the Elderly—Outcomes and Recent Improvements, Downloaded from circ.ahajournals.org, Aug. 26, 2008, 265-272.
Dubreuil et al., Percutaneous Mitral Valve Annuloplasty for Ischemic Mitral Regurgitation: First in Man Experience With a Tempory Implant, Catheterization and Cardiovascular Interventions, 2007, 1053-61, 69.
Duffy et al., Feasibility and Short-Term Efficacy of Percutaneous Mitral Annular Reduction for the Therapy of Funcitonal Mitral Regurgitation in Patients With Heart Failure, Catheterization and Cardiovascular Interventions, 2006, 205-210, 68.
Epstein et al., Gross and Microscopic Pathological Changes Associated With Nonthoracotomy Implantable Defibrillator Leads, Downloaded from circ.ahajournals.org, Jul. 23, 2008, 1517-24.
Epstein et al., Embolic Complications Associated With Radiofrequency Catheter Ablation, The American Journal of Cardiology, Mar. 15, 1996, 655-658, vol. 77.
Fagundes et al., Safety of Single Transseptal Puncture for Ablation of Atrial Fibrillation: Retrospective Study from a Large Cohort of Patients, Journal of Cardiovascular Electrophysiology, Dec. 2007, 1277-81, vol. 18, No. 12.
Feldman et al., Patient selection for percutaneous mitral valve repair: insight from early clinical trial applications, Nature Clinical Practice Cardiovascular Medicine, Feb. 2008, 84-90, vol. 5, No. 2.
Feldman et al., Percutaneous Mitral Valve Repair Using the Edge-to-Edge Technique—Six-Month Results of the Everest Phase I Clinical Trial, Journal of the American College of Cardiology, Dec. 6, 2005, 2134-40, vol. 46, No. 11.
Fernandez et al., Early and late-phase events after valve replacement with the St. Jude Medical prosthesis in 1200 patients, The Journal of Thoracic and Cardiovascular Surgery, Feb. 1994, 394-407, vol. 107, No. 2.
Gillinov et al., Durability of Mitral Valve Repair for Degenerative Disease, The Journal of Thoracic and Cardiovascular Surgery, Nov. 1998, 734-743, vol. 116, No. 5.
Grossi et al., Intraoperative Effects of the Coapsys Annuloplasty System in a Randomized Evaluation (RESTOR-MV) of Functional Ischemic Mitral Regurgitation, The Society of Thoracic Surgeons, 2005, 1706-11, 80.
Grossi et al., Late Results of Mitral Valve Reconstruction in the Elderly, The Society of Thoracic Surgeons, 2000, 1224-6, 70.
Grossi et al., Minimally Invasive Mitral Valve Surgery: A 6-Year Experience With 714 Patients, the Society of Thoracic Surgeons, 2002, 660-4, 74.
Hendren et al., Mitral Valve Repair for Ischemic Mitral Insufficiency, The Society of Thoracic Surgeons, 1991, 1246-52, 52.
Heupler et al., Infection Prevention Guidelines for Cardiac Catheterization Laboratories, Catheterization and Cardiovascular Diagnosis, 1992, 260-263, 25.
Hvass et al., Papillary Muscle Sling: A New Functional Approach to Mitral Repair in Patients With Ischemic Left Ventricular Dysfunction and Functional Mitral Regurgitation, The Society of Thoracic Surgeons, 2003, 809-11, 75.
Ibrahim et al., The St. Jude Medical prosthesis—A thirteen-year experience, The Journal of Thoracic and Cardiovascular Surgery, Aug. 1994, 221-230, vol. 108, No. 2.
Iskandar et al., Tricuspid Valve Malfunction and Ventricular Pacemaker Lead: Case Report and Review of the Literature, Echocardiography: A Jrnl of CV Ultrasound & Allied Tech., 2006, 692-697, vol. 23, No. 8.

(56) References Cited

OTHER PUBLICATIONS

Kasegawa et al., Mitral Valve Repair for Anterior Leaflet Prolapse With Expanded Polytetrafluoroethylene Sutures, The Society of Thoracic Surgeons, 2006, 1625-31, 81.
Kaye et al., Feasibility and Short-Term Efficacy of Percutaneous Mitral Annular Reduction for the Therapy of Heart Failure-Induced Mitral Regurgitation, Downloaded from circ.ahajournals.org, Aug. 26, 2008, 1795-97.
International Search Report and Written Opinion dated Sep. 22, 2008 issued in PCT Application No. PCT/US08/63560, 11 pages.
International Search Report and Written Opinion dated Sep. 29, 2008 issued in PCT Application No. PCT/US08/63568, 12 pages.
Kerensky, Complications of Cardiac Catheterization and Strategies to Reduce Risks, Diagnostic and Therapeutic Cardiac Catheterization, 1998, Chapter 8, 91-105.
Koertke et al., INR Self-Management Permits Lower Anticoagulation Levels After Mechanical Heart Valve Replacement, downloaded from circ.ahajournals.org, Aug. 26, 2008, II-75-II-78.
Kratz et al., St. Jude Prosthesis for Aortic and Mitral Valve Replacement: A Ten-Year Experience, The Society of Thoracic Surgeons, 1993, 462-8, 56.
Kron et al., Surgical Relocation of the Posterior Papillary Muscle in Chronic Ischemic Mitral Regurgitation, The Society of Thoracic Surgeons, 2002, 600-1, 74.
Kuwahara et al., Mechanism of Recurrent/Persistent Ischemic/Functional Mitral Regurgitation in the Chronic Phase After Surgical Annuloplasty—Importance of Augmented Posterior Leaflet Tethering, Circulation, Jul. 4, 2006, I-529-I-534.
Laskey et al., Multivariable Model for Prediction of Risk of Significant Complication During Diagnostic Cardiac Catheterization, Catheterization and Cardiovascular Diagnosis, 1993, 185-190, 30.
Lee et al., Mitral Valve Reconstruction: Experience Related to Early and Late Mortality and Reoperation, J Heart Valve Dis, Nov. 2005, 715-721, vol. 14, No. 6.
Liddicoat et al., Percutaneous Mitral Valve Repair: A Feasibility Study in an Ovine Model of Acute Ischemic Mitral Regurgitation, Catheterization and Cardiovascular Interventions, 2003, 410-416, 60.
Lim et al., Percutaneous Transthoracic Ventricular Puncture for Diagnostic and Interventional Catheterization, Catheterization and Cardiovascular Interventions, 2008, 915-918, 71.
Lin et al., Severe Symptomatic Tricuspid Valve Regurgitation Due to Permanent Pacemaker or Implantable Cardioverter-Defibrillator Leads, Journal of the American College of Cardiology, May 17, 2005, 1672-5, vol. 45, No. 10.
Lozonschi et al., Transapical Mitral Valved Stent Implantation, The Society of Thoracic Surgeons, 2008, 745-8, 86.
Mack, Percutaneous Therapies for Mitral Regurgitation: Where Do We Stand and Where Are We Going? Do Current Devices Really Represent a Step Forward Compared to Surgery?, 2007 Heart Valve Summit, Jun. 7, 2007, 59 pages.
Maleki et al., Intracardiac Ultrasound Detection of Thrombus on Transseptal Sheath: Incidence, Treatment, and Prevention, Journal of Cardiovascular Electrophysiology, Jun. 2005, 561-565, vol. 16, No. 6.
Maniu et al., Acute and Chronic Reduction of Functional Mitral Regurgitation in Experimental Heart Failure by Percutaneous Mitral Annuloplasty, Journal of the American College of Cardiology, Oct. 19, 2004, 1652-61, vol. 44, No. 8.
McGee et al., Recurrent mitral regurgitation after annuloplasty for functional ischemic mitral regurgitation, Surgery for Acquired Cardiovascular Disease, The Journal of Thoracic and Cardiovascular Surgery, Dec. 2004, 916-924.e4, vol. 128, No. 6.
Mehra et al., Surgery for Severe Mitral Regurgitation and Left Ventricular Failure: What Do We Really Know?, Journal of Cardiac Failure, Mar. 2008, 145-150. vol. 14, No. 2.
Menicanti et al., Functional Ischemic Mitral Regurgitation in Anterior Ventricular Remodeling: Results of Surgical Ventricular Restoration with and Without Mitral Repair, Heart Failure Reviews, 2004, 317-327, 9.
Messas et al., Efficacy of Chordal Cutting to Relieve Chronic Persistent Ischemic Mitral Regurgitation, Circulation, Sep. 9, 2003, II-111-II-115.
Meurin et al., Thromboembolic events early after mitral valve repair: Incidence and predictive factors, International Journal of Cardiology, 2008, 45-52, 126.
Mirable et al., What are the characteristics of patients with severe, symptomatic, mitral regurgitation who are denied surgery?, The European Society of Cardiology, 2007, 1358-65, 28.
Mitchell et al., Complications, Cardiac catheterization and coronary intervention, Chapter 9, 2008, 238-270.
Mishra et al., Coapsys Mitral Annuloplasty for Chronic Functional Ischemic Mitral Regurgitation: 1-Year Results, The Society of Thoracic Surgeons, 2006, 42-46, 81.
Morgan et al., Left Heart Catheterization by Direct Ventricular Puncture: Withstanding the Test of Time, Catheterization and Cardiovascular Diagnosis, 1989, 87-90, 16.
Murday et al., A Prospective Controlled Trial of St. Jude Versus Starr Edwards Aortic and Mitral Valve Prostheses, The Society of Thoracic Surgeons, 2003, 66-74, 76.
Nifong et al., Robotic mitral valve surgery: A United States multicenter trial, The Journal of Thoracic and Cardiovascular Surgery, Jun. 2005, 1395-1404, vol. 129, No. 6.
Noto et al., Cardiac Catheterization 1990: A Report of the Registry of the Society for Cardiac Angiography and Interventions (SCA&I), Catheterization and Cardiovascular Diagnosis, 1991, 75-83, 24.
Ohlow et al., Incidence and outcome of femoral vascular complications among 18,165 patients undergoing cardiac catheterisation, International Journal of Cardiology, 2008, 1-6.
Piazza et al., Transcatheter Mitral Valve Repair for Functional Mitral Regurgitation: Coronary Sinus Approach, Journal of Interventional Cardiology, 2007, 495-508, vol. 20, No. 6.
Pedersen et al., iCoapsys Mitral Valve Repair System: Percutaneous Implantation in an Animal Model, Catheterization and Cardiovascular Interventions, 2008, 125-131, 72.
Prifti et al., Ischemic Mitral Valve Regurgitation Grade II-III: Correction in Patients with Impaired Left Ventricular Function undergoing Simultaneous Coronary Revascularization, J Heart Valve Dis, Nov. 2001, 754-762, vol. 10, No. 6.
Richardson et al., Is a port-access mitral valve repair superior to the sternotomy approach in accelerating postoperative recovery?, Interactive CardioVascular and Thoracic Surgery, Downloaded from icvts.ctsnetjournals.org, Aug. 26, 2008, 670-683, 7.
Ruiz, New Percutaneous Approaches for Mitral Regurgitation, Lenox Hill Heart and Vascular Institute of New York, May 13-16, 2008, 26 pages.
Rumel et al., Section on Cardiovascular Diseases—The Correction of Mitral Insufficiency With a Trans-Valvular Polyvinyl Formalinized Plastic (Ivalon) Sponge Prosthesis, American College of Chest Physicians, Apr. 1958, Downloaded from chestjournal.org, Jul. 23, 2008, 401-413.
Seeburger et al., Minimal invasive mitral valve repair for mitral regurgitation: results of 1339 consecutive patients, European Journal of Cardio-thoracic Surgery, 2008, 1-6.
Southard et al., Current Catheter-Based Treatments of Functional Mitral Regurgitation, Cardiac Interventions Today, Jun. 2007, 41-44.
Svensson et al., United States Feasibility Study of Transcatheter Insertion of a Stented Aortic Valve by the Left Ventricular Apex, The Society of Thoracic Surgeons, 2008, 46-55, 86.
Toledano et al., Mitral regurgitation: Determinants for referral for cardiac surgery by Canadian cardiologists, Can J. Cardiol, Mar. 1, 2007, 209-214, vol. 23, No. 3.
Tops et al., Percutaneous Valve Procedures: An Update, Curr Probl Cardiol, Aug. 2008, 417-426.
Walther et al., Transapical minimally invasive aortic valve implantation; the initial 50 patients, European Journal of Cardio-thoracic Surgery, 2008, 983-988, 33.
Webb et al., Percutaneous Mitral Annuloplasty With the MONARC System: Preliminary Results From the Evolution Trial, TCT-103, The American Journal of Cardiology, Oct. 22-27, 2006, 49M.
Webb et al., Percutaneous Transvenous Mitral Annuloplasty—Initial Human Experience with Device Implantation in the Coronary Sinus, downloaded from circ.ahajournals.org, Aug. 26, 2008, 851-855.

(56) References Cited

OTHER PUBLICATIONS

Webster et al., Impact of transvenous ventricular pacing leads on tricuspid regurgitation in pediatric and congenital heart disease patients, J Interv Card Electrophysiol, 2008, 65-68, 21.

Ye et al., Six-month outcome of transapical transcatheter aortic valve implantation in the initial seven patients, European Journal of Cardiothoracic Surgery, 2007, 16-21, 31.

Yoshida, et al., Assessment of Left-to-Right Atrial Shunting After Percutaneous Mitral Valvuloplasty by Transesophageal Color Doppler Flow-Mapping, Circulation, Dec. 1989, 1521-1526, vol. 80, No. 6.

Zhou et al., Thromboembolic Complications of Cardiac Radiofrequency Catheter Ablation: A Review of the Reported Incidence, Pathogenesis and Current Research Directions, Journal of Cardiovascular Electrophysiology, Apr. 1999, 611-620, vol. 10, No. 4.

Eisenhauer et al., Closure of Prosthetic Paravalvular Mitral Regurgitation With the Gianturco-Grifka Vascular Occlusion Device, Catheterization and Cardiovascular Interventions, 2001, 5 pages, vol. 54.

Hourihan et al., Transcatheter Umbrella Closure of Valvular and Paravalvular Leaks, American College of Cardiology, Nov. 15, 1992, 7 pages, vol. 20, No. 6.

Moscucci et al., Coil Embolization of a Periprosthetic Mitral Valve Leak Associated With Severe Hemolytic Anemia, Images in Cardiovascular Medicine, American Heart Association, Inc., 2001, 2 pages, vol. 104.

Rashkind et al. Nonsurgical closure of patent ductus arteriosus: clinical application of the Rashkind PDA Occluder System, Therapy and Prevention—Congenital Heart Disease, Mar. 1987, 10 pages, vol. 75, No. 3.

Ryhänen et al., Invivo biocompatibility evaluation of nickel-titanium shape memory metal alloy: Muscle and perineural tissue responses and encapsule membrane thickness, Muscle and Perineural Tissue Response to Nitinol, Reveived Aug. 11, 1997; accepted Jan. 19, 1998, 8 pages.

International Search Report and Written Opinion dated Jan. 16, 2009 issued in PCT Application No. PCT/US08/83497, 10 pages.

Balzer et al., Real-time transesophageal three-dimensional echocardiography for guidance of percutaneous cardiac interventions: first experience, Clinical Research in Cardiology, May 29, 2008, 565-574, vol. 97, No. 9.

Carlson et al., Lead Perforation: Incidence in Registries, Pace Industry Viewpoint, Jan. 2008, 13-15, vol. 31.

Clinical Trials.gov, Comparing the Effectiveness of a Mitral Valve Repair Procedure in Combination With Coronary Artery Bypass Grafting (CABG) Versus CABG Alone in People with Moderate Ischemic Mitral Regurgitation, http://clinicaltrials.gov/ct2/show/record/NCT00806988?term=mitral+repair&rank=7, Feb. 24, 2009, 1-3.

Clinical Trials.gov, Safety and Efficacy Study of the PTMA Device to Reduce Mitral Valve Regurgitation in Patients With Heart Failure (PTOLEMY2Canada), http://clinicaltrials.gov/ct2/show/study/NCT00815386?term=Viacor&rank=3, Verified by Viacor Dec. 2008, Downloaded from internet Feb. 24, 2009, 1-3.

Clinical Trials.gov, Study of Safety and Efficacy of the Percutaneous Reduction of Mitral Valve Regurgitation in Heart Failure Patients (PTOLEMY-2), http://clinicaltrials.gov/ct2/show/NCT00787293?term=Viacor&rank=5, Verified by Viacor Nov. 2008, Downloaded from internet Feb. 24, 2009, 1-2.

Cohen, Trans-Septal Technique for Tandemheart Insertion, Lenox Hill Heart and Vascular Institute of New York, Barcelona May 22-May 25, 2007, 18 pages.

Corbisiero et al., Does Size Really Matter? A Comparison of the Riata Lead Family Based on Size and Its Relation to Performance, Pace, Jun. 2008, vol. 31, 722-726.

Criber et al., Treatment of Calcific Aortic Stenosis With the Percutaneous Heart Valve—Mid-Term Follow-Up From the Initial Feasibility Studies: The French Experience, Journal of the American College of Cardiology, Mar. 21, 2006, vol. 47, No. 6, 1241-1223.

Danik et al., Timing of delayed perforation with the St. Jude Riata lead: A single-center experience and a review of the literature, Heart Rhythm Society, Dec. 2008, vol. 5, No. 12, 1667-1672.

Del Valle-Fernández et al., Transcatheter heart valves for the treatment of aortic stenosis: state-of-the-art, Minerva Cardioangiologica, Oct. 2008, vol. 56, No. 5, 543-556.

Douthitt, Cardiac Dimensions® Inc. Receives CE Mark for CARILLON™ Mitral Contour System™, Cardiac Dimensions—News, htpp://www.cardiacdimensions.com/usa/press-release-2-4-09.html, downloaded Feb. 24, 2009, 1-2.

Dvorin, Endovalve Inc., Pioneering percutaneous mitral valve replacement., Start-Up Windhover's Review of Emerging Medical Ventures, Jun./Jul. 2006, vol. 11, No. 7, 1-2.

Eltchaninoff, Clinical results of percutaneous aortic valve implantation, Euro PCR07, Cribier-Edwards, May 25, 2007, 30 pages.

Evalve reports 1st MitraClip treatments in the Netherlands, Medical Device Daily, Feb. 19, 2009, vol. 13, No. 32, 2 pages.

A first for MiCardia's Dynoplasty, Medical Device Daily, Feb. 19, 2009, vol. 13, No. 32, 1 page.

Fitts et al., Fluoroscopy-Guided Femoral Artery Puncture Reduces the Risk of PCI-Related Vascular Complications, Journal of Interventional Cardiology, vol. 21, No. 3, 2008, 273-278.

Gelsomino et al., Left ventricular diastolic function after restrictive mitral ring annuloplasty in chronic ischemic mitral regurgitation and its predictive value on outcome and recurrence of regurgitation, International Journal of Cardiology, vol. 132, 2009, 419-428.

Geyfman et al., Cardiac Tamponade as Complication of Active-Fixation Atrial Lead Perforations: Proposed Mechanism and Management Algorithm, PACE, Apr. 2007, vol. 30, 498-501.

Gorman et al., Surgical Therapy for Mitral Regurgitation: The Key to Preventing Heart Failure?, Prevention of Heart Failure After Myocardial Infarction, 2008, 211-215.

Notice of Allowance dated Jun. 3, 2013 issued in U.S. Appl. No. 12/872,228, 7 pages.

Final Office Action dated Jun. 19, 2013 issued in U.S. Appl. No. 11/748,147, 10 pages.

Notice of Allowance dated Jul. 8, 2013 issued in Canadian Patent Application No. 2,627,517, 1 page.

Notice of Allowance dated Aug. 1, 2013 issued in U.S. Appl. No. 12/510,929, 10 pages.

Notice of Allowance dated Aug. 12, 2013 issued in U.S. Appl. No. 11/940,724, 26 pages.

International Preliminary Report on Patentability dated May 27, 2010 issued in PCT/US2008/083574, 4 pages.

International Preliminary Report on Patentability and Written Opinion, issued in PCT/US2008/063560, dated Nov. 26, 2009, 8 pages.

International Preliminary Report and Written Opnion issued in PCT/US2008/083570, dated May 27, 2010, 4 pages.

Notice of Allowance dated Oct. 24, 2013 issued in U.S. Appl. No. 11/748,147, 12 pages.

Office Action dated Nov. 1, 2013 issued in U.S. Appl. No. 13/347,522, 6 pages.

European Office Action dated Nov. 7, 2013 issued in European Patent Application No. 10 804 952.9, 5 pages.

European Intent to Grant dated Feb. 22, 2013 issued in European Patent Application No. 08 755 418.4, 7 pages.

European Search Report dated Mar. 6, 2013 issued in European Patent Application No. 10804952.9, 8 pages.

Notice of Allowance dated Mar. 8, 2013 issued in U.S. Appl. No. 11/748,138, 9 pages.

Final Office Action dated Mar. 13, 2013 issued in U.S. Appl. No. 11/748,147, 10 pages.

Final Office Action dated Mar. 22, 2013 issued in U.S. Appl. No. 12/510,929, 13 pages.

Notice of Allowance dated Apr. 11, 2013 issued in U.S. Appl. No. 13/545,927, 12 pages.

Supplemental Notice of Allowability dated May 2, 2013 issued in U.S. Appl. No. 13/545,927, 5 pages.

\* cited by examiner

FIGURE 14A
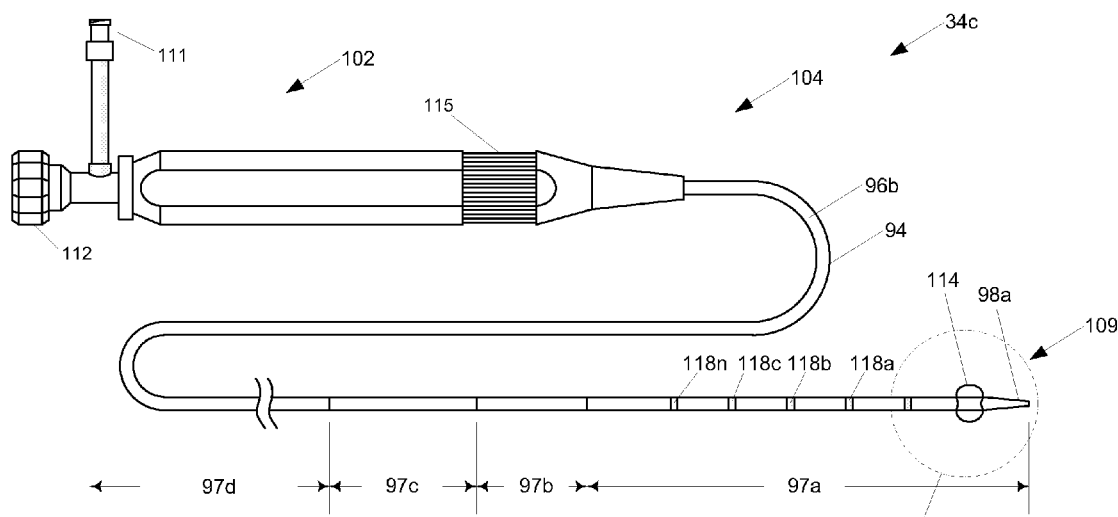
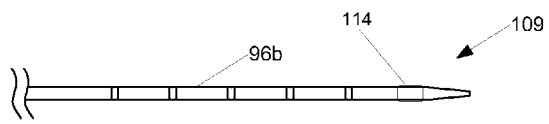
FIGURE 14B
Close-up section of tip
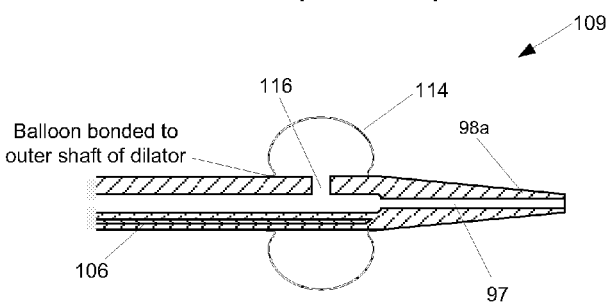
FIGURE 14C

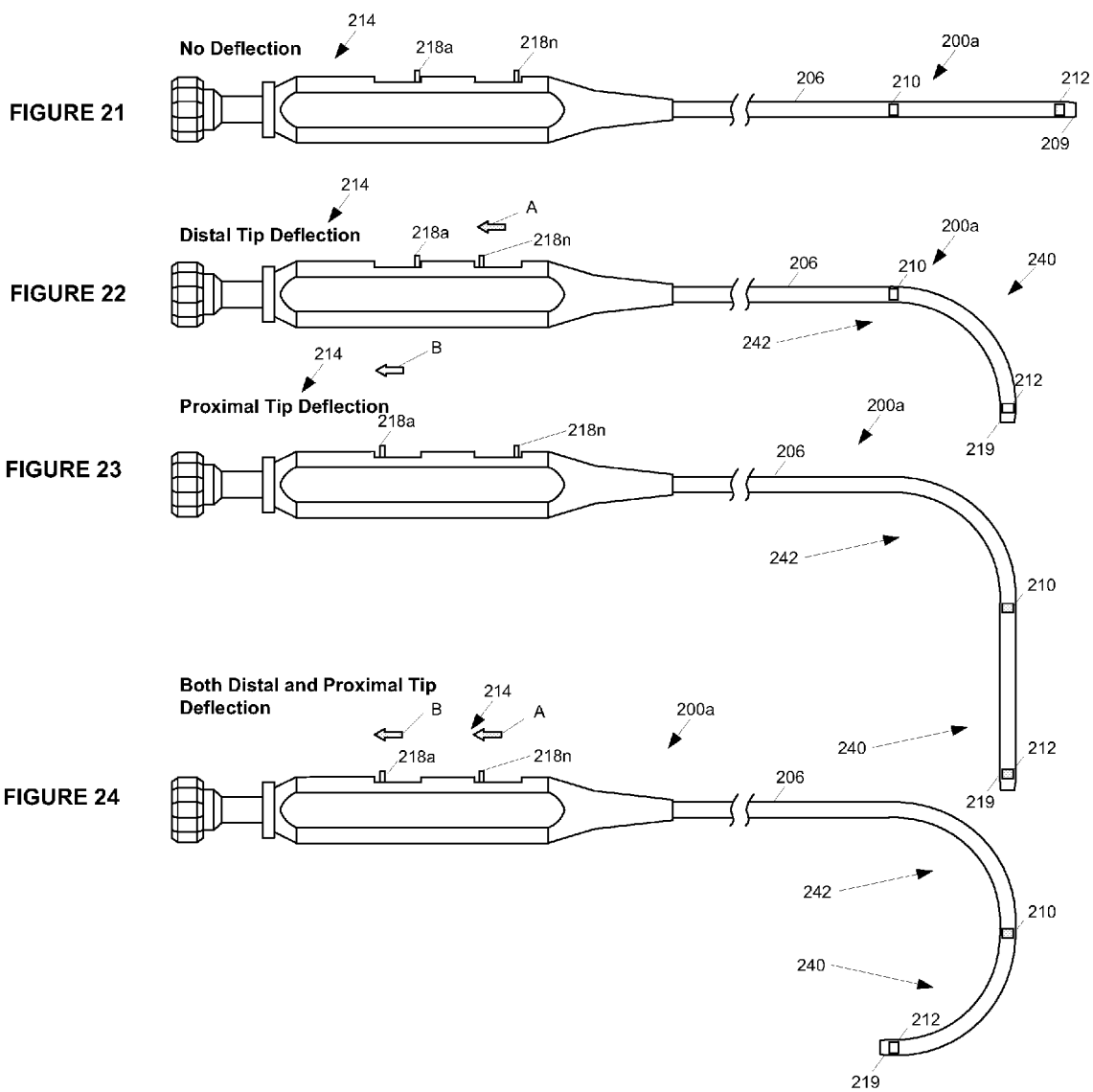

Exploded Balloon Assembly

Balloon Assembly Perspective view

Bending Withdrawal Sequence of the Steerable Catheter
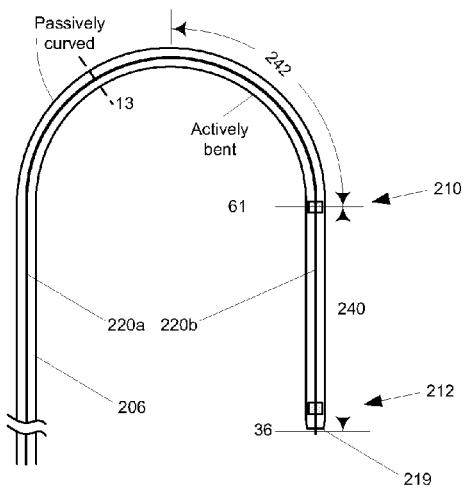
FIGURE 40
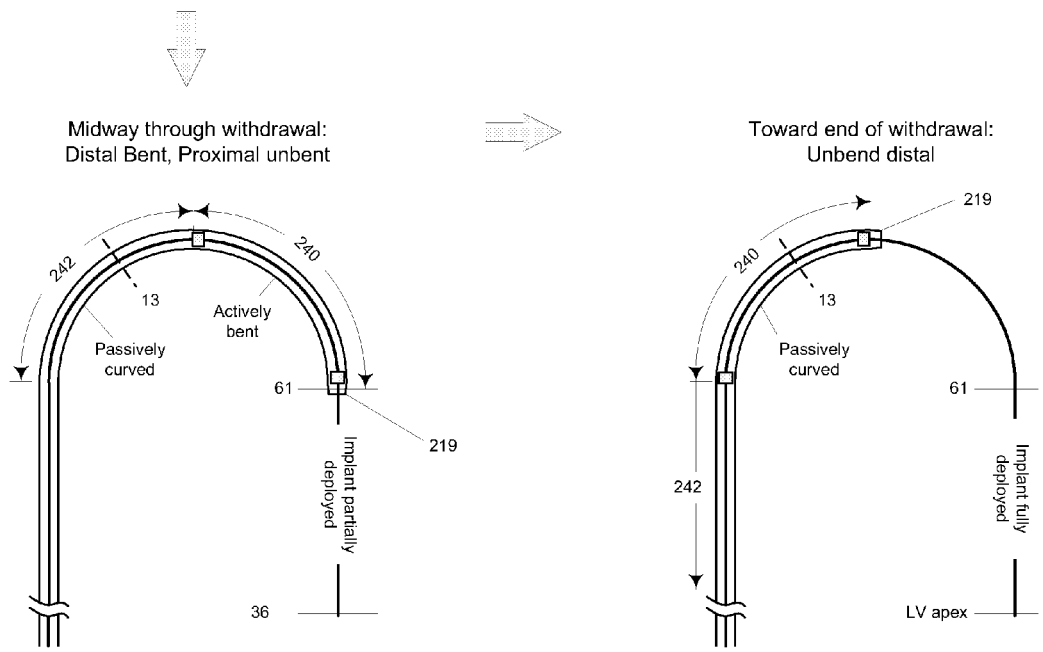
FIGURE 41
FIGURE 42

MITRAL VALVE SPACER AND SYSTEM AND METHOD FOR IMPLANTING THE SAME

FIELD

The present disclosure relates to the repair and/or correction of dysfunctional heart valves, and more particularly pertains to heart valve implants and systems and methods for delivery and implementation of the same.

BACKGROUND

The human heart has four chambers, the left and right atrium and the left and right ventricles. The chambers of the heart alternately expand and contract to pump blood through the vessels of the body. The cycle of the heart includes the simultaneous contraction of the left and right atria, passing blood from the atria to the left and right ventricles. The left and right ventricles then simultaneously contract forcing blood from the heart and through the vessels of the body. In addition to the four chambers, the heart also includes a check valve at the upstream end of each chamber to ensure that blood flows in the correct direction through the body as the heart chambers expand and contract. These valves may become damaged, or otherwise fail to function properly, resulting in their inability to properly close when the downstream chamber contracts. Failure of the valves to properly close may allow blood to flow backward through the valve resulting in decreased blood flow and lower blood pressure.

Mitral regurgitation is a common variety of heart valve dysfunction or insufficiency. Mitral regurgitation occurs when the mitral valve separating the left coronary atrium and the left ventricle fails to properly close. As a result, upon contraction of the left ventricle blood may leak or flow from the left ventricle back into the left atrium, rather than being forced through the aorta. Any disorder that weakens or damages the mitral valve can prevent it from closing properly, thereby causing leakage or regurgitation. Mitral regurgitation is considered to be chronic when the condition persists rather than occurring for only a short period of time.

Regardless of the cause, mitral regurgitation may result in a decrease in blood flow through the body (cardiac output). Correction of mitral regurgitation typically requires surgical intervention. Surgical valve repair or replacement may be carried out as an open heart procedure. The repair or replacement surgery may last in the range of about three to five hours, and may be carried out with the patient under general anesthesia. The nature of the surgical procedure requires the patient to be placed on a heart-lung machine. Because of the severity/complexity/danger associated with open heart surgical procedures, corrective surgery for mitral regurgitation is typically not recommended until the patient's ejection fraction drops below 60% and/or the left ventricle is larger than 45 mm at rest.

BRIEF DESCRIPTION OF THE DRAWINGS

Features and advantage of the claimed subject matter will be apparent from the following description of embodiments consistent therewith, which description should be considered in conjunction with the accompanying drawings, wherein:

FIG. 14A illustrates a perspective view of a yet another embodiment of a dilator consistent with the present disclosure;

FIG. 14B illustrates a perspective view of one embodiment of the dilator shown in a deflected or retracted position consistent with the present disclosure;

FIG. 14C illustrates a perspective view of one embodiment of the dilator shown in an inflated or expanded position consistent with the present disclosure;

FIGS. 20A-D illustrate various views of another embodiment of a steerable catheter consistent with the present disclosure;

FIG. 21 illustrates a perspective view of an embodiment of a steerable catheter in a non-deflected position consistent with the present disclosure;

FIG. 22 illustrates a perspective view of an embodiment of a steerable catheter with the distal tip in a deflected position consistent with the present disclosure;

FIG. 23 illustrates a perspective view of an embodiment of a steerable catheter with the proximal tip in a deflected position consistent with the present disclosure;

FIG. 24 illustrates a perspective view of an embodiment of a steerable catheter with the distal tip and the proximal tip in a deflected position consistent with the present disclosure;

FIGS. 40-42 illustrate one embodiment of a withdrawal sequence for a steerable catheter consistent with the present disclosure.

DESCRIPTION

Figure 1:
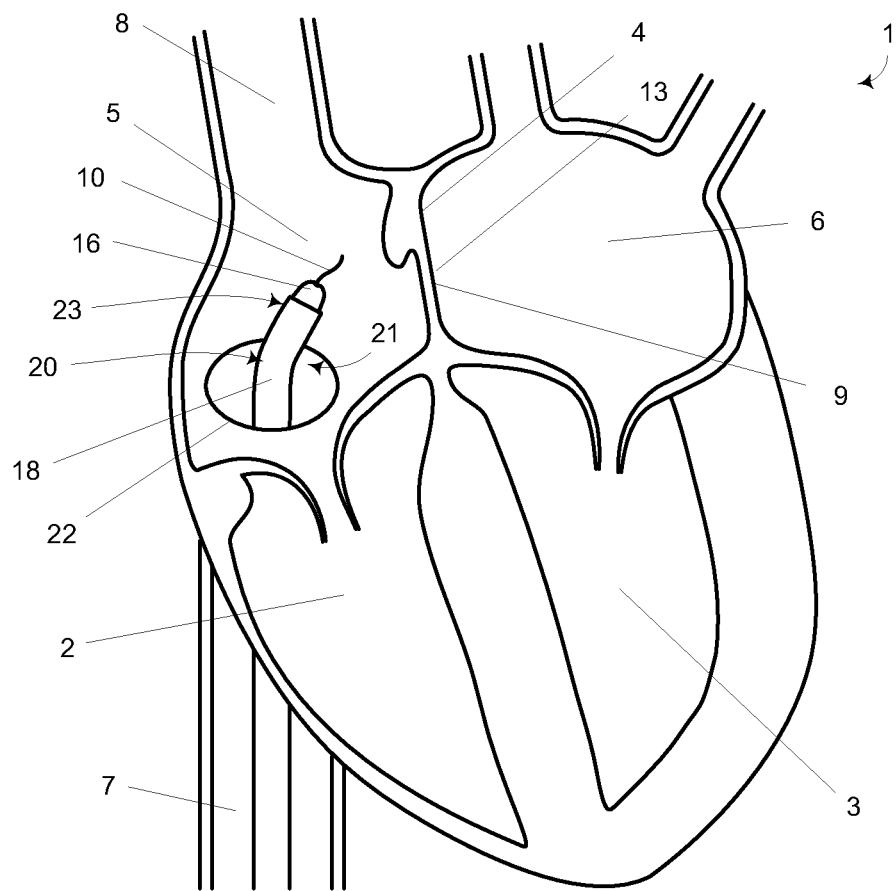
FIG. 1 illustrates a perspective view of an embodiment of a transseptal catheter in the right atrium consistent with the present disclosure.

The present disclosure relates to a system and method of implanting a heart implant. For example, the system and method according to one embodiment of the present disclosure may be used to implant a heart valve implant which may suitably be used in connection with the treatment, diagnostics and/or correction of a dysfunctional or inoperative heart valve. One suitable implementation for a heart valve implant consistent with the present disclosure is the treatment of mitral valve regurgitation. For the ease of explanation, the heart valve implant herein is described in terms of a mitral valve implant, such as may be used in treating mitral valve regurgitation as described in U.S. patent application Ser. No. 11/258,828 filed Oct. 26, 2005 and U.S. patent application Ser. No. 12/209,686 filed Sep. 12, 2008, both of which are fully incorporated herein by reference. However, a heart valve implant consistent with the present disclosure may be employed for treating, diagnosing and/or correcting other dysfunctional or inoperative heart valves, such as the heart valve implant(s) discussed herein in connection with FIGS. 28 to 39.

It should be understood that the technology of the present disclosure (including the implant described in connection with FIGS. 28 to 39) is not limited to mitral valve implants and systems and methods of implanting mitral valve implants. Indeed, the systems and methods according to the present disclosure may be used to implant heart implants configured to be used in connection with the treatment, diagnostics and/or correction of other heart conditions. For example, and without limitation, the system and method consistent with the present disclosure may be used to implant a regurgitation implant configured to induce a controlled regurgitation in a heart valve (such as, but not limited to, a mitral heart valve), for example, in a manner that is generally consistent with advanced disease of the heart. The regurgitation implant may include a regurgitation implant as described in U.S. patent Ser. No. 11/940,724 filed Nov. 15, 2007 and U.S. patent application Ser. No. 12/209,686 filed Sep. 12, 2008, both of which are fully incorporated herein by reference.

According to one embodiment, a heart implant consistent with the present disclosure may comprise a heart valve implant configured to interact with at least a portion of an existing heart valve to prevent and/or reduce regurgitation. For example, at least a portion of one or more cusps or leaflets of the heart valve may interact with, engage, and/or seal against at least a portion of the heart valve implant when the heart valve is in a closed condition. The interaction, engagement and/or sealing between at least a portion of at least one cusp or leaflet and at least a portion of the heart valve implant may reduce and/or eliminate regurgitation in a heart valve, for example, providing insufficient sealing, including only a single cusp, e.g., following removal of a diseased and/or damaged cusp, and/or having a ruptured chordae. A heart valve implant consistent with the present disclosure may be used in connection with various additional and/or alternative defects and/or deficiencies.

For the ease of explanation, one embodiment of the system and method consistent with the present disclosure is described in terms of a system and method for implanting a mitral valve implant, such as may be used in treating mitral valve regurgitation. By way of an overview, the system and method may generally comprise placing a guide wire into the left ventricle and advancing a mitral valve implant through a delivery catheter and into the left ventricle. For example, a guide wire may be initially placed into the left atrium of the heart, for example, by way of transseptal puncture of the heart from the right atrium through the fossa ovalis into the left atrium. A dilator may then be advanced along the guide wire to the left atrium and may be passed through the mitral valve into the left ventricle. The dilator may include a balloon which may be inflated to facilitate passing the dilator through the mitral valve without damaging the mitral valve or becoming entangled in the mitral valve chordae. A steerable catheter may then be advanced along the dilator into the left ventrical. The steerable catheter may be positioned within the left ventrical to the approximate location in which the implant will be secured. The implant may then be advanced through the steerable catheter and secured to the native cardiac tissue.

Referring now to FIG. 1, a cross-sectional schematic view of a portion of a four chamber heart 1 is illustrated. The outflow tracts of the right and left ventricles 2, 3 are not shown in order to better illustrate the septum 4 between the right and left atria 5, 6. As shown, the inferior vena cava (IVC) 7 and superior vena cava (SVC) 8 communicate with the right atrium 5 which is separated from the left atrium 6 by the intra-atrial septum 4. While not a limitation of the present disclosure, it is may be advantageous to make the transseptal puncture 13 through the fossa ovalis 9 since the fossa ovalis 9 is thinnest portion of the intra-atrial septum 4.

According to one embodiment consistent with the present disclosure, a guide wire 10 may be advanced up the IVC 7 and into the right atrium 5. The guide wire 10 may include any guide wire configured to be advanced up the IVC 7 and into the right atrium 5. Consistent with one embodiment, the guide wire 10 may be the same as the delivery guide wire discussed herein; however, the guide wire 10 may also be separate and distinct from the delivery guide wire. Without limitation, access to the right atrium 5 may be accomplished by way of the Seldinger wire technique. For example, the right femoral vein (not shown) may be accessed with a hollow needle (not shown) and a guide wire 10 may be inserted. The needle may be removed and a dilator 16 may be inserted over the guide wire 10. The sheath 18 of a catheter 20 (such as, but not limited to, a Mullins catheter or the like) having a pre-bent region 21 proximate the distal tip 23 of the catheter 20 may be inserted over the dilator 16. The sheath 18, dilator 16, catheter 20 and guide wire 10 may then be advanced up the IVC 7 through the opening 22 into the right atrium 5 as generally illustrated in FIG. 1.

Figure 2:
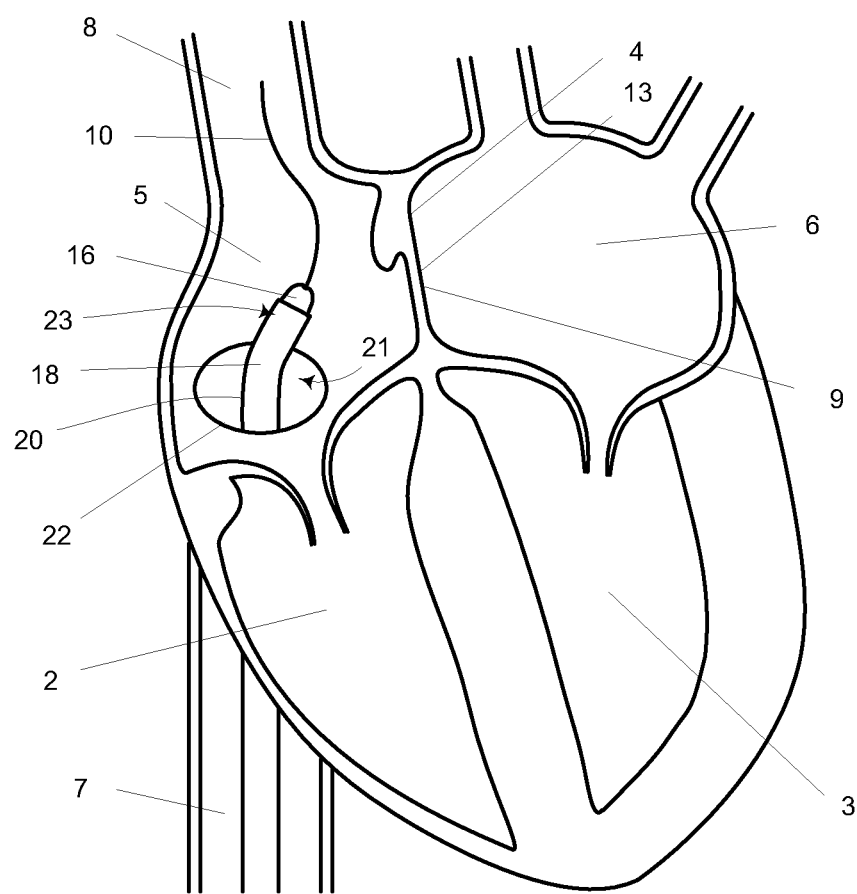
FIG. 2 illustrates a perspective view of an embodiment of a guide wire advanced into the superior vena cava consistent with the present disclosure.
Figure 3:
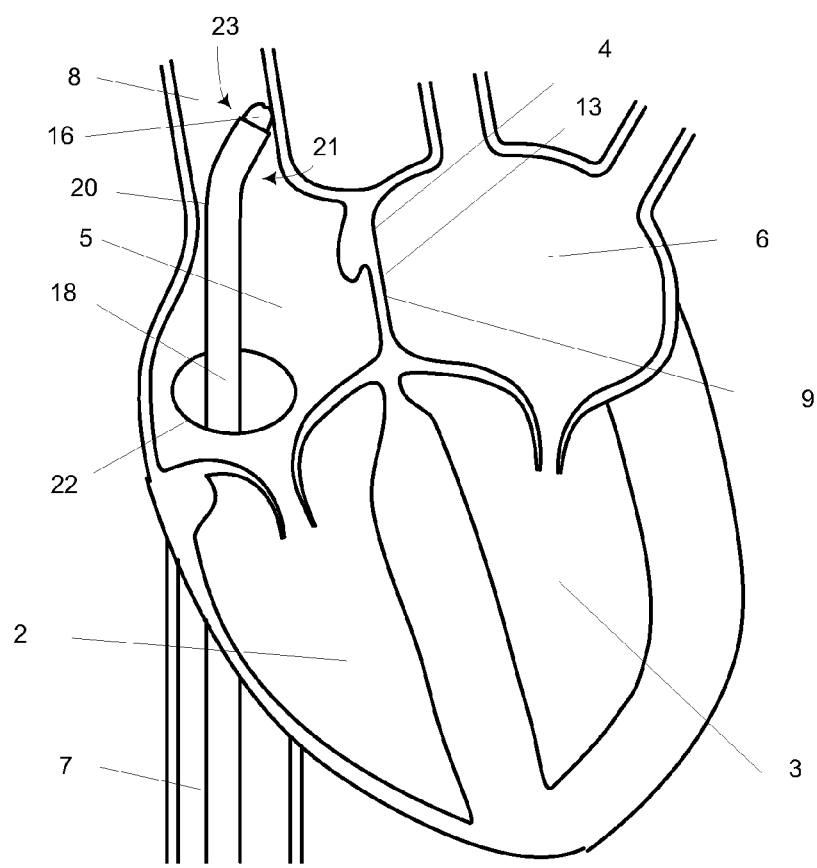
FIG. 3 illustrates a perspective view of an embodiment of a catheter advanced into the superior vena cava consistent with the present disclosure.

With the sheath 18, dilator 16, catheter 20 and guide wire 10 in the right atrium 5, access to the left atrium 6 may be achieved by transseptal puncture 13 from the right atrium 5 through the intra-atrial septum 4. For example, at least a portion of the guide wire 10 may be advanced out of the distal tip 23 of the dilator 16, sheath 18 and/or catheter 20 as generally shown in FIG. 2. According to an embodiment, the guide wire 10 may be at least partially advanced into the SVC 8 as generally illustrated in FIG. 2 and the distal tip 23 of the catheter 20 may then be at least partially advanced along the guide wire 10 into the SVC 8 as generally illustrated in FIG. 3. Because the SVC 8 is a thin-walled vein, it may be advantageous to place the guide wire 10 in the SVC 8 and then advance the catheter 20 along the guide wire 10 since the spring-tipped atraumatic guide wire 10 reduces the potential for damaging the SVC 8 compared to the catheter 20 and dilator 16.

Figure 4:
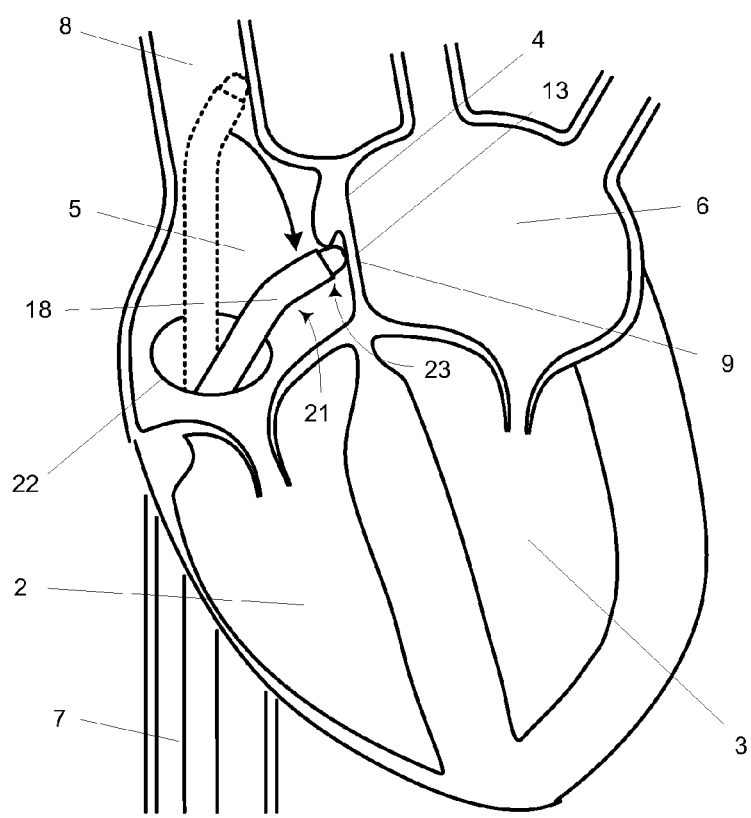
FIG. 4 illustrates a perspective view of an embodiment of a catheter tip against the fossa ovalis consistent with the present disclosure.
Figure 5:
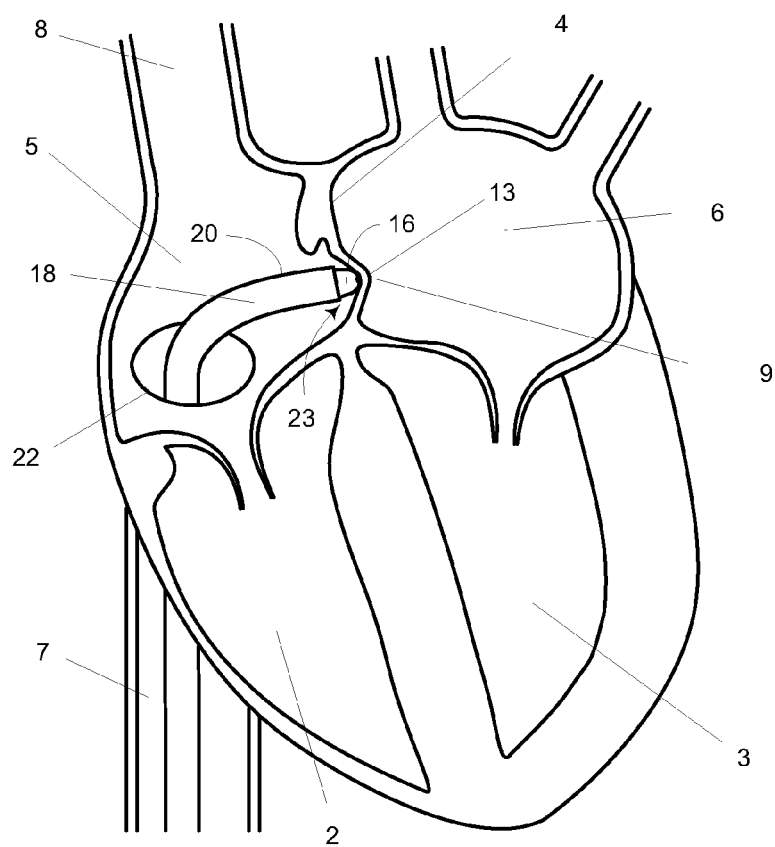
FIG. 5 illustrates a perspective view of an embodiment of a catheter tenting the fossa ovalis consistent with the present disclosure.

With the distal tip 23 at least partially received in the SVC 8, the guide wire 10 may be retracted into the dilator 16 and the catheter 20 may be retracted (i.e., pulled downward) such that the pre-bent portion 21 of the sheath 18 facilitates guiding the distal tip 23 to the fossa ovalis 9 as generally illustrated in FIG. 4. For example, using one or more visualization techniques (such as, but not limited to, intracardiac echo (ICE), fluoroscopy, and the like), the sheath 18 may be retracted proximally, dragging the distal tip 23 along the intra-atrial septum 4 until the distal tip 23 is positioned proximate to the fossa ovalis 9. Optionally, the position of the sheath 18 relative to the fossa ovalis 9 may be confirmed by gently pushing the sheath 18 distally against the intra-atrial septum 4 to "tent" the fossa ovalis 9 as generally illustrated in FIG. 5. The "tenting" of the fossa ovalis 9 may be seen on ICE, fluoroscopy or the like.

Figure 6:
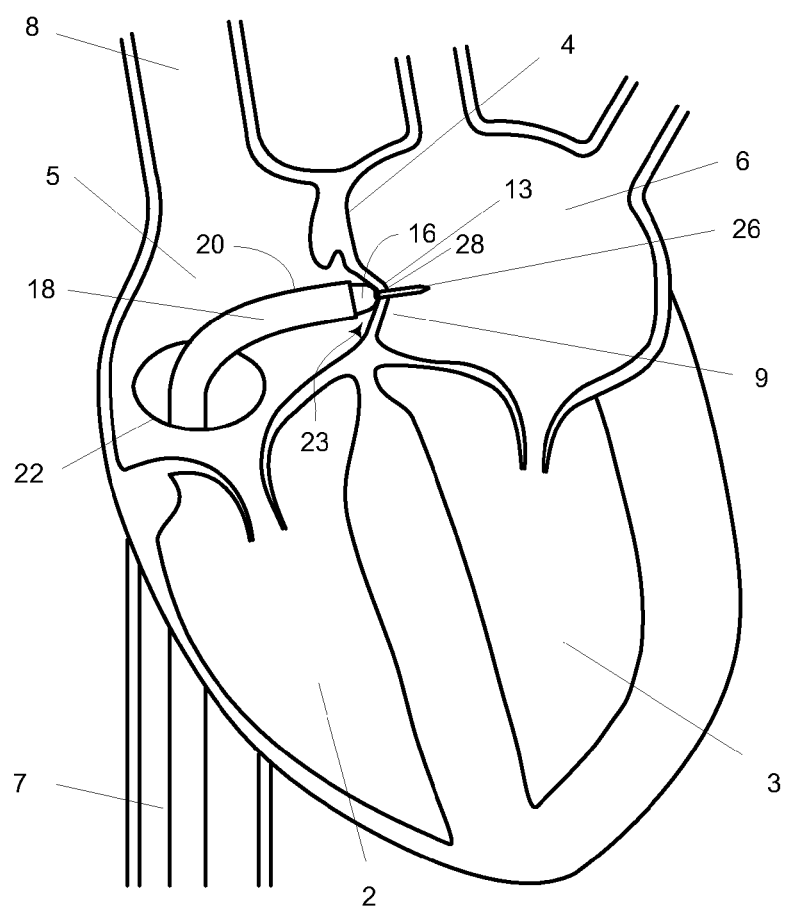
FIG. 6 illustrates a perspective view of an embodiment of a needle puncturing the fossa ovalis consistent with the present disclosure.
Figure 7:
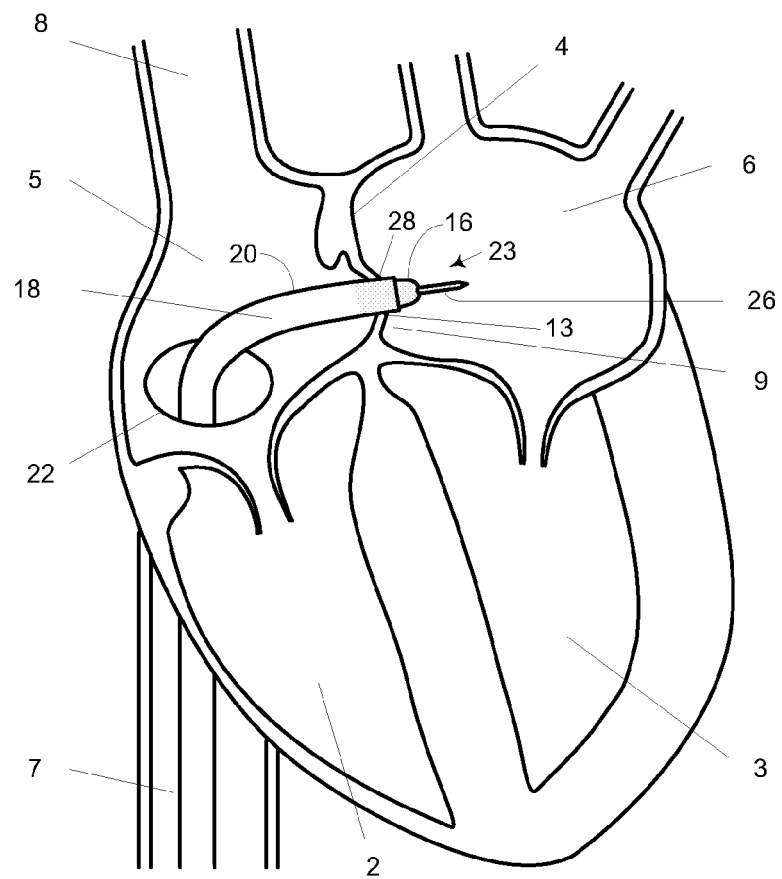
FIG. 7 illustrates a perspective view of an embodiment of a transseptal catheter punctured through the fossa ovalis consistent with the present disclosure.
Figure 8:
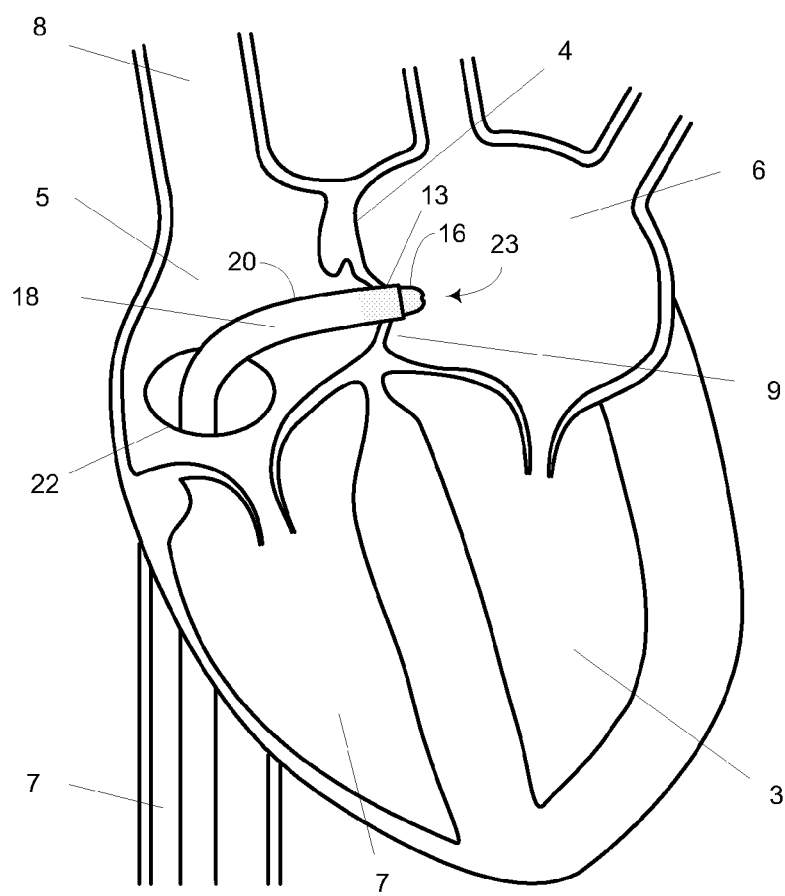
FIG. 8 illustrates a perspective view of an embodiment of a transseptal catheter punctured through the fossa ovalis with its distal tip in the left atrium with the needle removed consistent with the present disclosure.

With the distal tip 23 proximate and/or contacting the fossa ovalis 9, the guide wire 10 may be removed from the catheter 20 and a transseptal needle 26 may be advanced through the catheter 20 towards the distal end 23 of the catheter 20 as generally shown in FIG. 6. The position of the catheter 20 may optionally be confirmed (for example, but not limited to, by "tenting") and the transseptal needle 26 may be advanced out of the distal tip 23 to form a puncture 28 through the fossa ovalis 9 and into the left atrium 6. The sheath 16, dilator 28 and catheter 20 may than be advanced through the puncture 28 of the fossa ovalis 9 and into the left atrium 6 as generally shown in FIG. 7. Once the sheath 16, dilator 28 and catheter 20 are through the fossa ovalis 9, the needle 26 may be removed from the catheter 20 as generally shown in FIG. 8.

Figure 9:
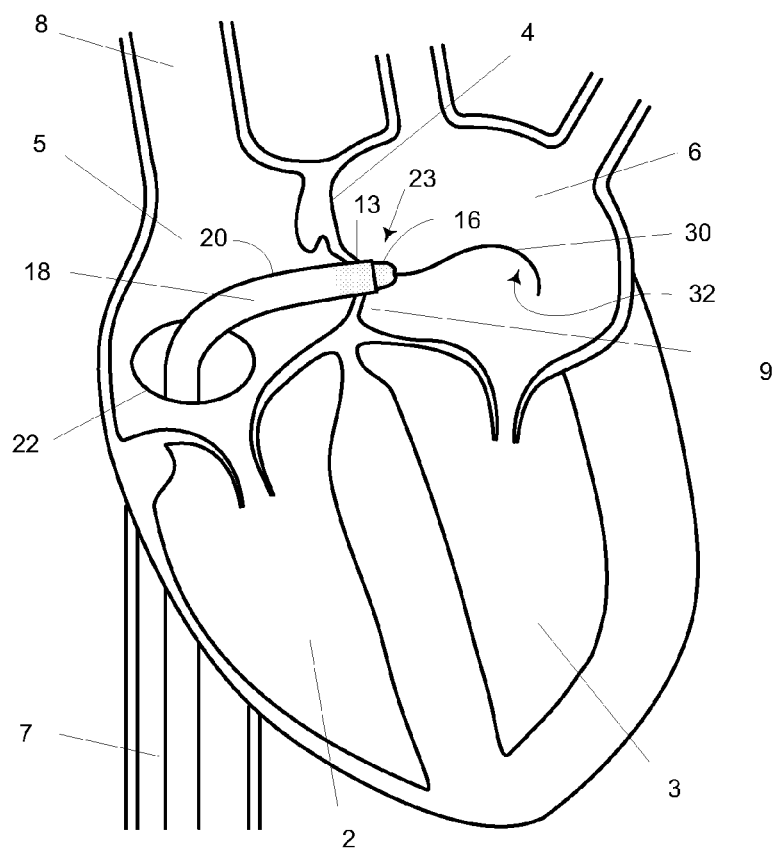
FIG. 9 illustrates a perspective view of an embodiment of a delivery guide wire advanced into the left atrium through the transseptal catheter consistent with the present disclosure.
Figure 10:
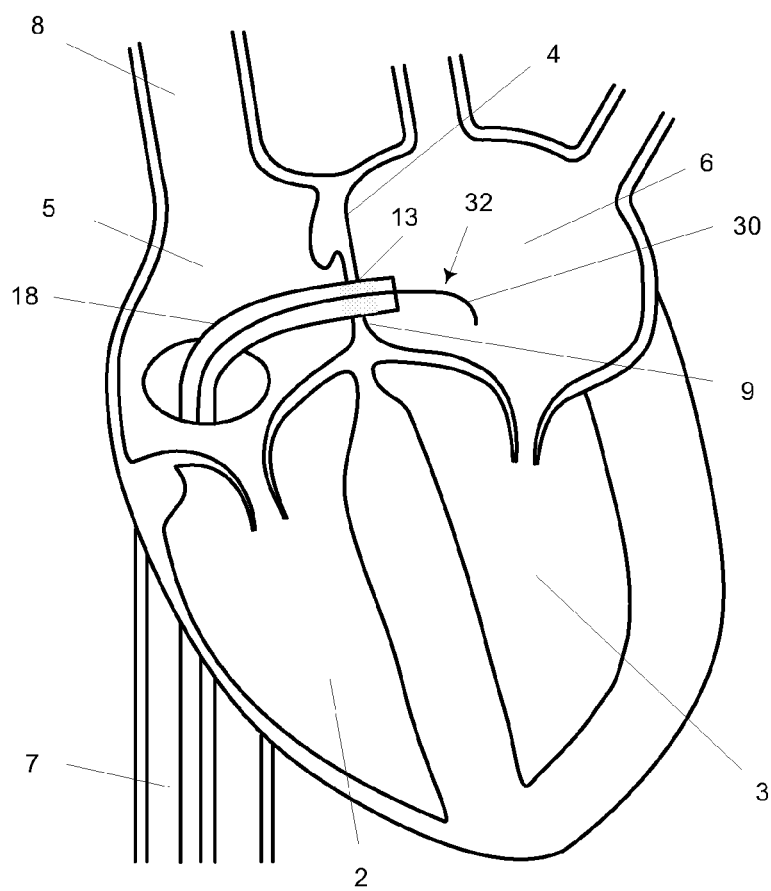
FIG. 10 illustrates a perspective view of an embodiment of a sheath and dilator removed with a delivery guide wire in the left atrium consistent with the present disclosure.

With the catheter 20 in the left atrium 6, a delivery guide wire 30 may be advanced through the catheter 20 until at least a portion of the distal tip 32 of the delivery guide wire 30 extends from the distal tip 23 of the catheter 20 and into the left atrium 6 as generally illustrated in FIG. 9. Once the distal tip 32 of the delivery guide wire 30 is disposed in the left atrium 6, the dilator 16 and the sheath 18 may be removed, leaving just the delivery guide wire 30 in the left atrium 6 as generally illustrated in FIG. 10.

The delivery guide wire 30 may be used as a guide for advancing other devices into the heart 1, and ultimately, into the left ventricle 3. Accordingly to at least one embodiment, the delivery guide wire 30 may be sufficiently stiff to resist undesirable bending and/or kinking and to resist undesirable movement of the distal tip 32. For example, the delivery guide wire 30 may comprise a stiff, 0.018" diameter guide wire having a stiffness of approximately 19,900,000 psi. The stiffness of the delivery guide wire 30 was determined as follows.

When a force is applied to a long thin column, there is no movement of the column until a minimum critical buckling force is achieved, $P_{cr}$, then further buckling occurs, though the force does not increase. For a long column of uniform cross-section and length l, which buckles under a critical force, $P_{cr}$, the following formula applies:

$$P_{cr} = n\pi^2 \frac{EI}{L^2}$$

Where:
n=a constant that is equal to 4 if both ends of the column are clamped and cannot move or rotate.
E=Modulus of elasticity of the material (psi)
I=Moment of inertia (in$^4$)
For a circular cross-section the moment of inertia is:

$$I = \frac{\pi d^4}{64}$$

Substituting for l in the first equation for $P_{cr}$ leads to:

$$P_{cr} = n\pi^3 \frac{Ed^4}{64L^2}$$

And solving for the modulus leads to:

$$E = \frac{64L^2 P_{cr}}{n\pi^3 d^4}$$

Based on the above, an 8 cm section of the delivery guide wire 30 was tested and a buckling force of 0.41 lbs. was determined. Therefore, $$E = \frac{64(3.15)^2(0.41)}{4\pi^3(0.018)^4} = 19,900,000 \text{ psi}$$

This stiffness (modulus of elasticity) of the delivery guide wire 30 may therefore be approximately 19,900,000 psi. Of course, the delivery guide wire 30 may have a stiffness greater than or less than 19,900,000 psi.

According to at least one other embodiment, the delivery guide wire 30 may include a typical 0.018" guide wire (for example a 0.018" angled standard exchange guide wire made by Merit Medical Systems of South Jordan, Utah, Model H20STDA18260EX which was determined to have a stiffness of approximately 1,360,000 psi based on the same methodology). In either embodiment, the delivery guide wire 30 may have a diameter greater than or less than 0.018".

Figure 11:
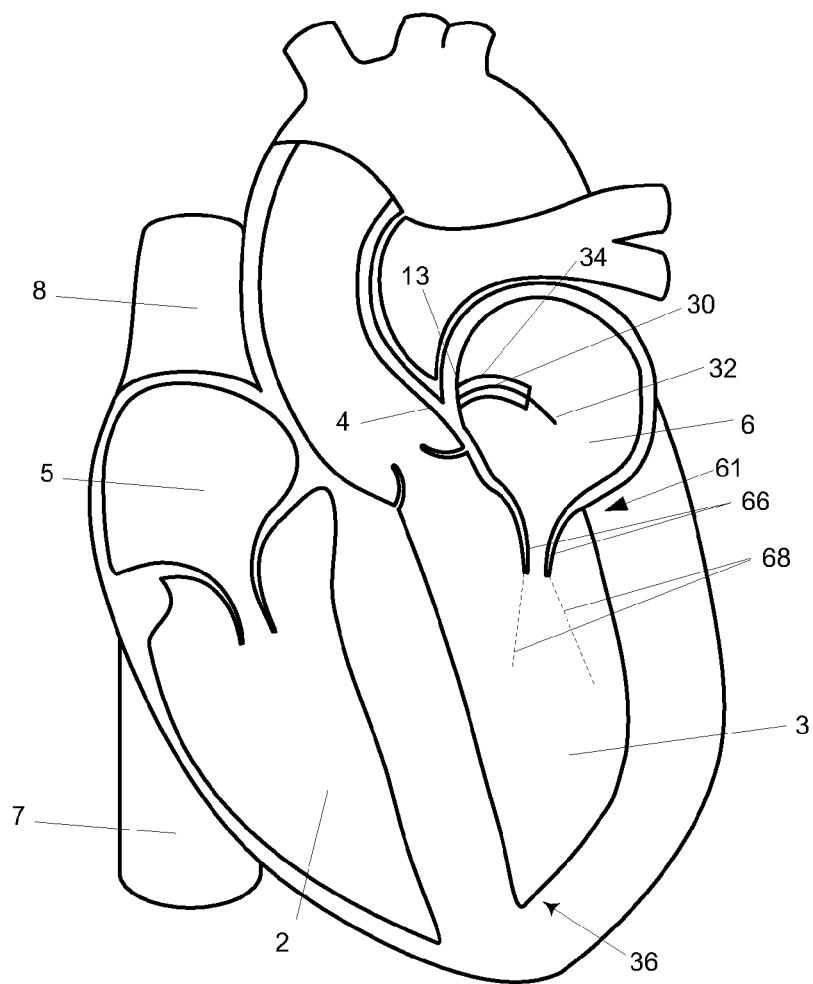
FIG. 11 illustrates a perspective view of an embodiment of a dilator advanced to the left atrium consistent with the present disclosure.

Turning now to FIG. 11, a dilator 34 may be advanced over the delivery guide wire 30 into the left atrium 6. The dilator 34 may be configured to pass through the mitral valve 61 into the left ventricle 3 without damaging the mitral valve 61 or becoming entangled in the mitral valve 61 (for example, the cusps 66, the chordae and/or papillary muscles 68 of the mitral valve 61). According to at least one embodiment, the dilator 34 of the present disclosure may be used to eliminate the delivery guide wire as disclosed in U.S. patent application Ser. No. 12/209,686 filed Sep. 12, 2008. However, it may be appreciated that the system and method disclosed in the present disclosure (and in particular the dilator 34) is not inconsistent with the system and method in U.S. patent application Ser. No. 12/209,686, and as such, the system and method disclosed in the present disclosure (including the dilator 34) may be used in conjunction with the system and method in U.S. patent application Ser. No. 12/209,686.

Figure 12:
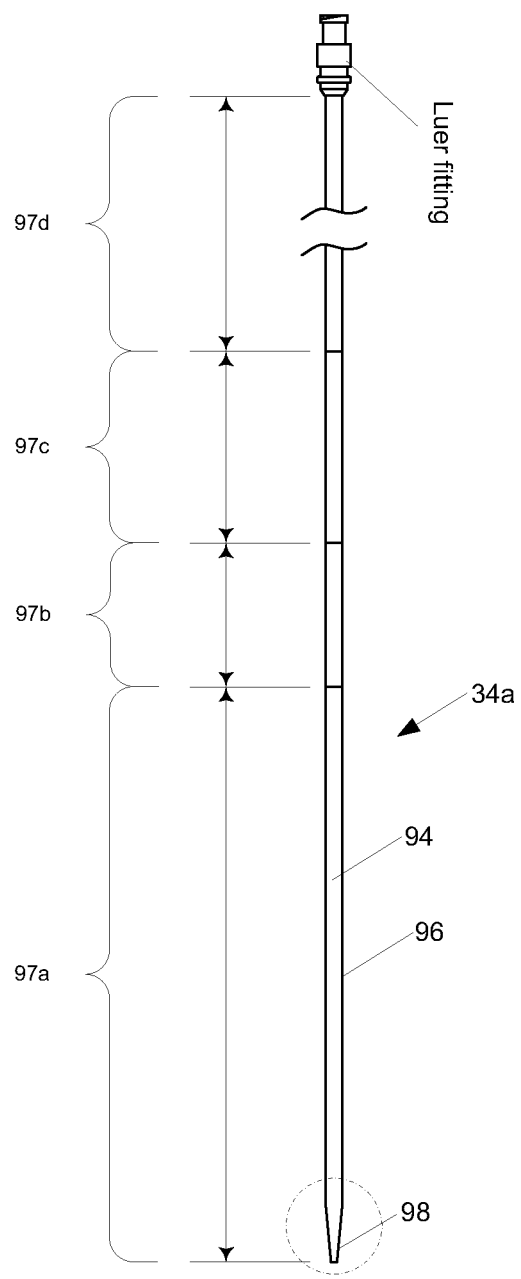
FIG. 12 illustrates a perspective view of one embodiment of a dilator consistent with the present disclosure.

One embodiment of a dilator 34a consistent with the present disclosure is generally illustrated in FIG. 12. The dilator 34a may include define at least one lumen 94 configured to receive at least a portion of the delivery guide wire 30. For example, the lumen 94 may have an internal diameter of approximately 0.038". The dilator 34a may also comprise a shaft 96 including a tapered tip region 98. The shaft 96 may comprise a plurality of segments or portions having different stiffness or hardness to produce the desired overall curvature. The shaft 96 may be formed from one or more suitable polymers such as, but not limited to, a polyether block amide. The shaft 96 may have a constant inner and/or outer diameter and may be made from different materials to provide the various stiffness or hardness. Alternatively, or in addition, the shaft 96 may have different inner and/or outer diameters and may be made from one or more materials. For example, the various stiffness or hardness of the shaft 96 may be provided by varying the thickness of the shaft 96 at the different segments or portions. The different hardness of the segments may provide differing degrees of bending stiffness to the dilator 34a which may facilitate advancing the dilator 34a into and/or out of the left ventricle 3.

As shown, the dilator 34a may comprise four different segments 97a, 97b, 97c and 97d. The first segment 97a may be disposed proximate the distal end region 98. The first segment 97a may optionally include the tapered distal tip 98 and may have a length of approximately 6 inches. The tapered distal tip 98 may be provided to facilitate advancing the tip 98 into the percutaneous puncture site in the groin as the dilator 34a is introduced over the delivery guide wire 30.

According to at least one embodiment, the first segment 97a may be formed of PEBAX™ 3533 having a durometer of 35 D. The second segment 97b may be adjacent to the first segment 97a and may have a length of approximately 1.5 inches. According to at least one embodiment, the second segment 97b may be formed of PEBAX™ 2533 having a durometer of 25 D. The third segment 97c may be adjacent to the second segment 97b and may have a length of approximately 2 inches. According to at least one embodiment, the third segment 97c may be formed of PEBAX™ 3533 having a durometer of 35 D. The forth segment 97d may be adjacent to the third segment 97c and may have a length of approximately 42.5 inches. According to at least one embodiment, the forth segment 97d may be formed of PEBAX™ 7233 having a durometer of 72 D.

It should be understood that the various lengths and hardness described above for the segments 97a-97d may be adjusted or changed depending upon the circumstances of its intended use. For example, patients with larger and/or smaller hearts may require one or more of the segments to be harder or softer. An important aspect of the segments 97a-97d is that the softest segment is the second segment 97b. Also, the second segment 97b is disposed approximately 6 inches from the tapered distal tip 98. As will be explained herein, the location of the second segment 97b may generally correspond to the of the transseptal puncture site 13 where the curvature of the dilator 34a may be greatest.

Figures 13A, 13B:
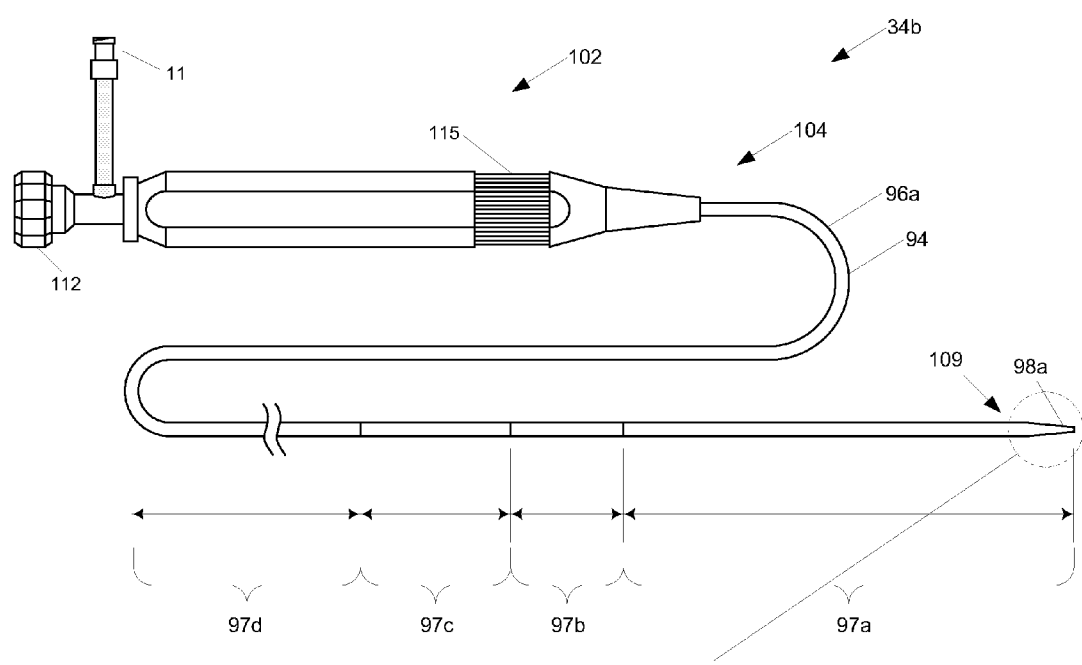
FIG. 13A illustrates a perspective view of an embodiment of a dilator consistent with the present disclosure.
FIG. 13B illustrates a close-up of one embodiment of the tip of the dilator shown in FIG. 13A consistent with the present disclosure.

Turning now to FIGS. 13A and 13B, another embodiment of a dilator 34b consistent with the present disclosure is generally illustrated. The dilator 34 may include a deflectable tip 98a configured to allow the user to bend the distal region 109 of the dilator 34b. The deflectable tip 98a may facilitate advancement of the dilator 34b through the mitral valve 61 by allowing the user to generally aim the tip 98 towards the mitral valve 61. According to at least one embodiment, the dilator 34b may include a handle assembly 102 coupled to a proximal end 104 of the shaft 96a. The shaft 96a may include a plurality of segments, for example, the segments 97a-97d described above. One or more deflecting wires 106 may be coupled to the distal end region 109 of the shaft 96a, for example, as generally illustrated in FIG. 13B. The deflecting wire 106 may optionally be disposed in a second lumen 113 disposed along the length of the shaft 96a. Additional deflecting wires 106 (not shown) may be provided in one or more additional lumens.

The deflecting wire 106 may be coupled to the handle assembly 102 such that the distal tip 98a may be bent as desired. According to one embodiment, the handle assembly 102 may include at least one knob, slider or the like 115 coupled to the deflecting wire 106 such that actuation of the knob 115 may result in movement of the distal tip 98a. For example, the knob 115 may be coupled to the deflecting wire 106 and may pull the deflecting wire 106 generally towards the handle assembly 102 causing the distal tip 98a to bend to one side.

The handle assembly 102 may also optionally include one or more valves or fittings. For example, the handle assembly 102 may include a fitting 111 (such as, but not limited to, a Luer lock fitting or the like) configured to allow the lumen 97 to be flushed. The handle assembly 102 may also optionally include a valve 112 (such as, but not limited to, a hemostasis valve) configured to seal with the delivery guide wire 30 (not shown).

The lumen 97 may have various diameters along the length of the shaft 96a. For example, the lumen 97 may have a smaller diameter proximate the distal tip 98a compared to the remainder of the shaft 96a. The lumen 97 proximate the tip 98a may be slightly larger than the diameter of the delivery guide wire 30 (for example, but not limited to, slightly larger than 0.018") such that the dilator 34a tracks well over the delivery guide wire 30. The remainder of the lumen 97 may have a larger diameter configured to reduce drag as the dilator 34a is advanced over the delivery guide wire 30.

Turning now to FIGS. 14A-14C, yet another embodiment of a dilator 34c consistent with the present disclosure is generally illustrated. The dilator 34c may comprise an expandable device 114 (such as, but not limited to a balloon or the like) configured to facilitate advancement of the dilator 34c through the mitral valve 61 without damaging the mitral valve 61 or becoming entangled in the mitral valve 61 (for example, the cusps 66, the chordae and/or papillary muscles 68 of the mitral valve 61). The expanding portion 114 may be disposed proximate the distal end region 109 of the shaft 96b, for example, substantially adjacent to the tapered tip 98a. The expanding portion 114 may be fluidly coupled to an expanding medium such as, but not limited to, a gas and/or liquid which may expand and/or enlarge the expanding portion 114 from the deflated or retracted position as generally illustrated in FIG. 14B to the inflated or expanded position as generally illustrated in FIG. 14A. According to at least one embodiment, the expanding medium may include carbon dioxide CO2 gas and/or saline. Optionally, contrast media may be introduced into the expanding portion 114 to allow the expanding portion 114 to be more easily visually located using fluoroscopy or the like. The contrast media may coat the inside surface of the expanding portion 114.

The expanding medium may be introduced through a fitting 111. According to at least one embodiment, the expanding medium may be coupled to the expanding portion 114 by way of the lumen 116a as generally illustrated in FIG. 14C. As may be appreciated, the delivery guide wire 30 may be received in the lumen 97 when the dilator 34c is expanded. The expanding medium may be coupled to the expanding portion 114 by way of a separate passageway (i.e., a passageway different from the lumen 97 configured to receive the delivery guide wire 30). This passageway may be the same lumen as the steering wire 106 is housed in, provided there is enough room for the expansion medium to pass around the steering wire.

The expanding portion 114 may include a resiliently expandable/collapsible material such as, but not limited to, silicone, Yulex™ or the like which may be selectively collapsed and/or expanded. The expanding portion 114 may be bonded to the shaft 96b of the dilator 34c and may include one or more passageways, aperture or lumen 116 fluidly coupled to the lumen 97 to allow the expansion medium to expand/collapse the expanding portion 114. The diameter of the expanding portion 114 should be small enough in the first or retracted/collapsed position to be advanced over the delivery guide wire 30 to the left atrium 6 and large enough when in the second or expanded/inflated position to be advanced through the cusps 66 and chordae 68 of the mitral valve 61 to reduce the potential of damaging the heart 1 and/or getting entangled within the mitral valve 61. For example, the shaft 97 may have an outer diameter of approximately 0.062" (e.g., a 5 Fr) and a length of approximately 110 cm or greater. The expanding portion 114 may diameter of approximately 0.100" in the first position and a diameter of approximately 15 mm to approximately 20 mm cm in the second position with a length of approximately 8 to approximately 10 mm.

The dilator 34c may optionally include a deflectable tip 98a configured to allow the user to bend the distal region 109 of the dilator 34b as generally described herein. The dilator 34c may also optionally include one or more radiopaque markers 118a-118n, for example, disposed about the distal end region 109. The position markers 118a-118n may be spaced evenly along the shaft 97 (such as, but not limited to, approximately 2 cm intervals from the distal tip 98a) and may be used to verify the position of the dilator 34c and/or for sizing the implant to be delivered.

While various embodiments of the dilator 34 consistent with the present disclosure have been described herein, it should be understood that one or more features of any of the various embodiments may be combined with any other embodiment. The dilator 34 consistent with he present disclosure may have an overall length (i.e., from the distal tip 98 to the handle assembly 102 of approximately 145 cm or less. However, the length and/or the diameter of the dilator 34 may depend upon the introduction site as well as the intended patient's physiology.

Figure 15:
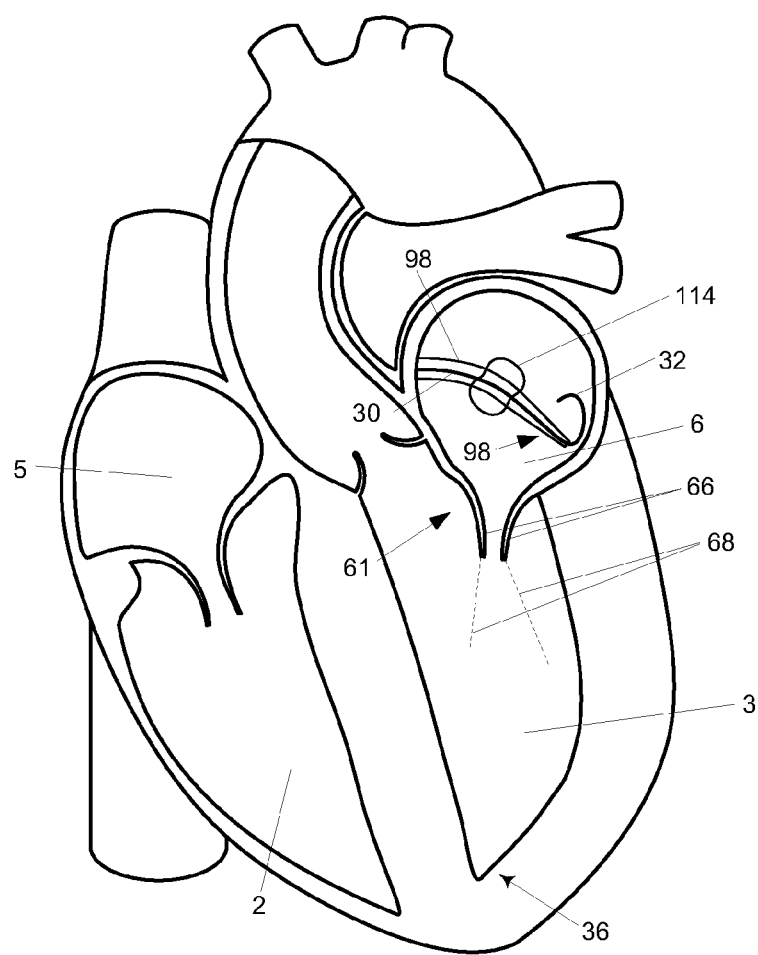
FIG. 15 illustrates a perspective view of a dilator in the inflated or expanded position located in the left atrium consistent with the present disclosure.
Figure 16:
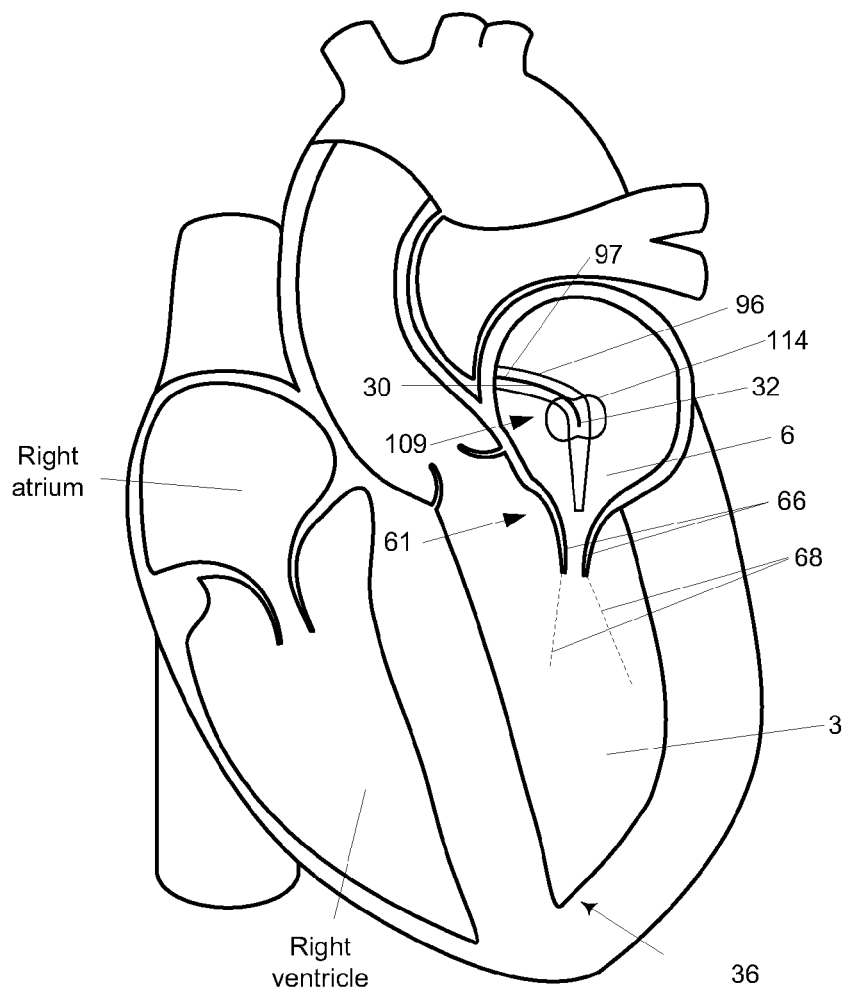
FIG. 16 illustrates a perspective view of a dilator in the inflated or expanded position located in the left atrium prior to passing through the mitral valve consistent with the present disclosure.

Turning now to FIG. 15, the dilator 34 may be advanced over the delivery guide wire 30 proximate to the tip 32 of the delivery guide wire 30. The tip 32 may still extend beyond the tip 98 of the dilator 34 to protect the atrial wall from perforation. According to one embodiment, the expanding portion 114 may be expanded as generally illustrated. The dilator 34 may aimed generally towards the mitral valve 61 as generally illustrated in FIG. 16. For example, the tip 98 may be bent or curved by actuating one or more knobs or the like (not shown) to move one or more deflecting wires as discussed herein. The tip 32 of the delivery guide wire 30 may optionally be retracted into the lumen 97 of the dilator 34 to increase the flexibility of the distal tip region 109. The curvature of the dilator 34 may be confirmed using fluoroscopic and/or echo guidance techniques or the like. For example, the contrast media and/or the radiopaque markers may be used.

Figure 17:
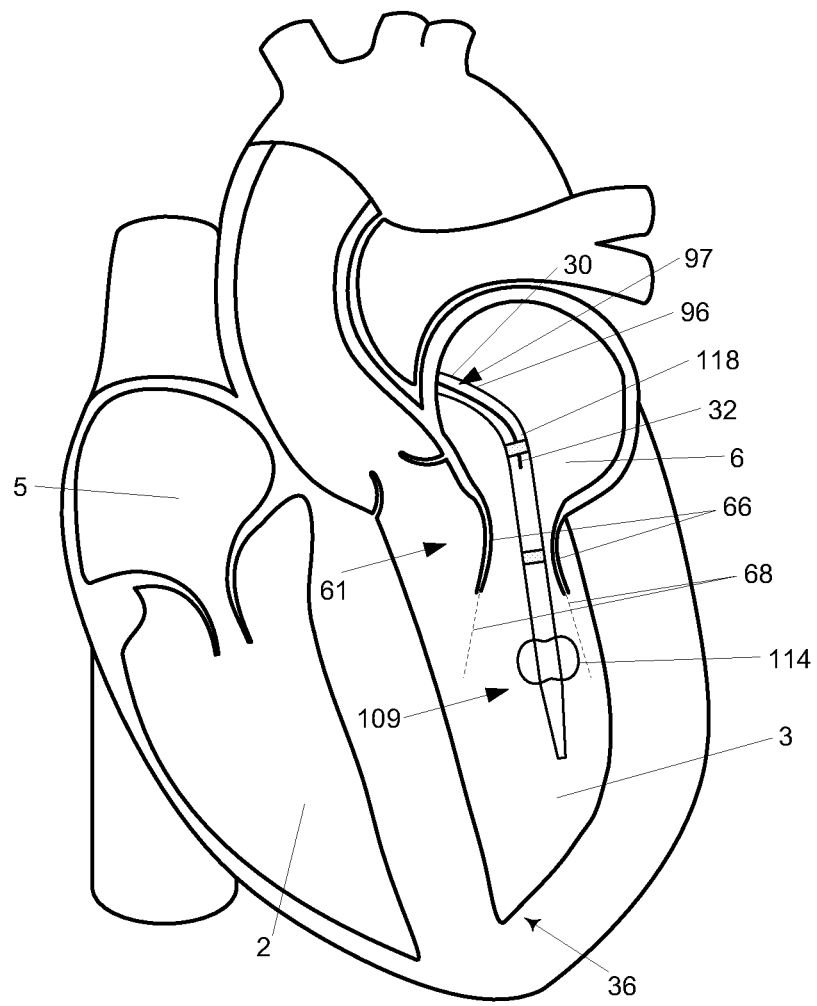
FIG. 17 illustrates a perspective view of a dilator located in the left ventricle consistent with the present disclosure.

Turning now to FIG. 17, with the dilator 34 aimed at the mitral valve 61 and the expanding portion 114 inflated, the distal end region 109 of the dilator 34 may be advanced through the mitral valve 61. It should be understood that the dilator 34 may be advanced through the mitral valve without either the deflectable tip 98 and/or the expandable portion 114; however, the use of one or more of the deflectable tip 98 and/or the expandable portion 114 may reduce the potential of damaging the heart 1 and/or getting entangled within the mitral valve 61. The second segment 97b of the shaft 96 may generally correspond to the location of the bend or curve of the dilator 34 proximate the transseptal puncture site 13. As may be appreciated, the necessary curvature of the dilator 34 between the transseptal puncture site 13 and the left ventricle 3 is relatively sharp.

The tip 32 of the delivery guide wire 30 may be still located inside the lumen 97 of the dilator 34 back in the left atrium 6 generally where it was located in FIG. 16. The dilator 34 may not yet be aimed or directed at the intended implantation site at this point. Instead, it is only important that the distal end region 109 of the dilator 34 is through the mitral valve 61 without damaging and/or entangling the cusps 66 and the chordae/papillary muscles 68.

Figure 18:
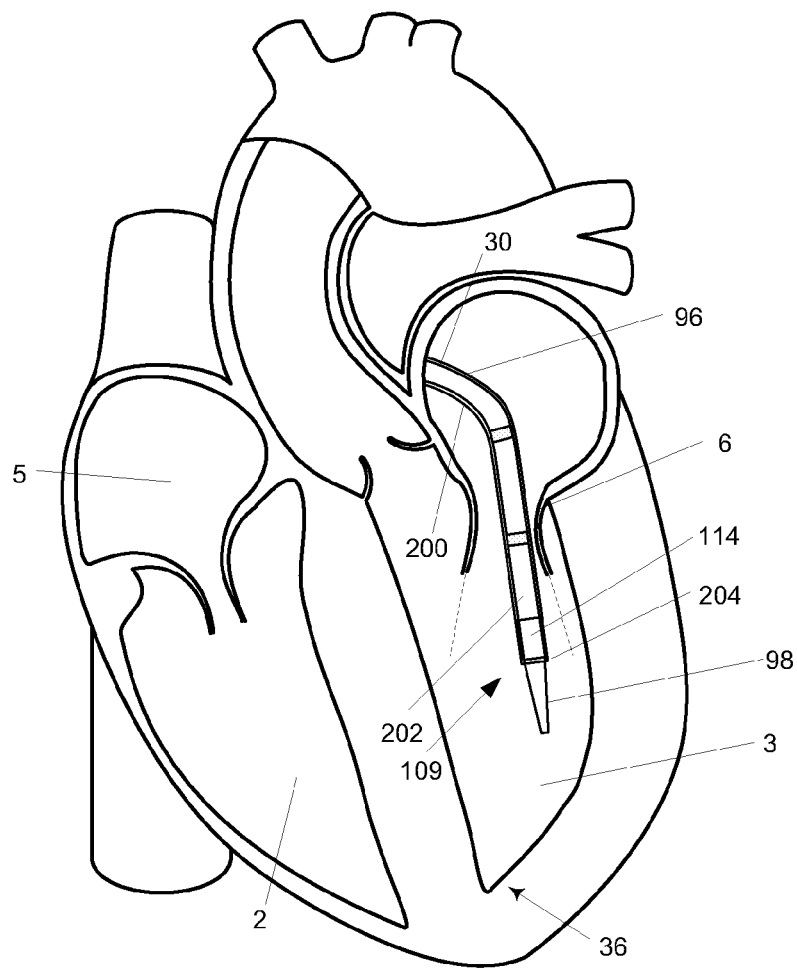
FIG. 18 illustrates a perspective view of an embodiment of a steerable catheter advanced over the dilator in the left ventricle consistent with the present disclosure.

Turning now to FIG. 18, the expandable portion 114 may be retracted/deflated and a steerable catheter 200 may be advanced over the dilator 34 into the left ventricle 3 proximate to the distal end region 109 of the dilator 34. The steerable catheter 200 may define at least one lumen 202 configured receive the dilator 34 as generally illustrated. The lumen 202 may also be configured to receive an implant (not shown) such as, but not limited to, a mitral valve implant as discussed herein with respect to FIGS. 27-39, as well as those generally disclosed in U.S. patent Ser. No. 11/940,724 filed Nov. 15, 2007 and U.S. patent application Ser. No. 12/209,686 filed Sep. 12, 2008, both of which are fully incorporated herein by reference. The steerable catheter 200 may also be configured to be selectively curved or bent to facilitate aiming of the distal tip 204 for securing the implant and/or facilitate removal of the steerable catheter 200.

Figure 19:
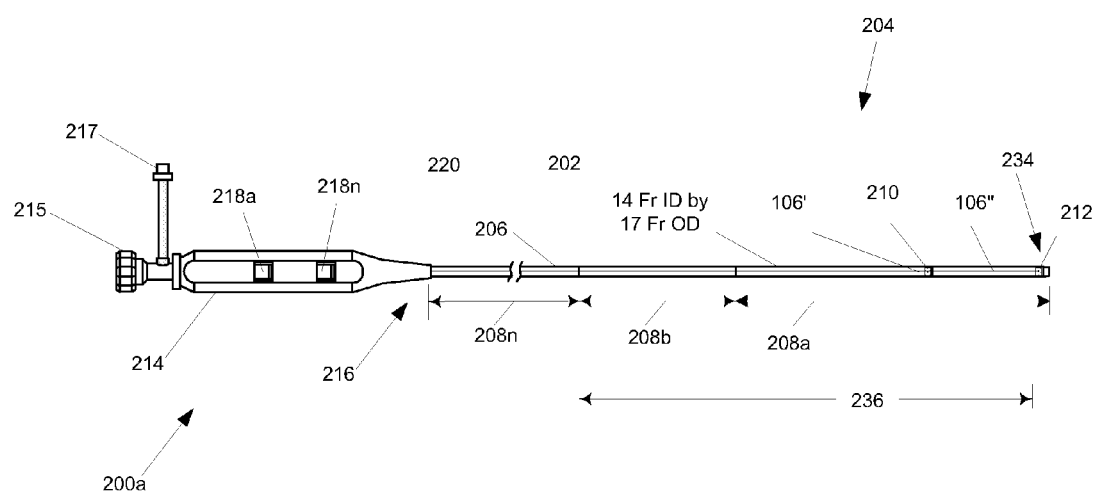
FIG. 19 illustrates a perspective view of one embodiment of a steerable catheter consistent with the present disclosure.
Figure 20A:
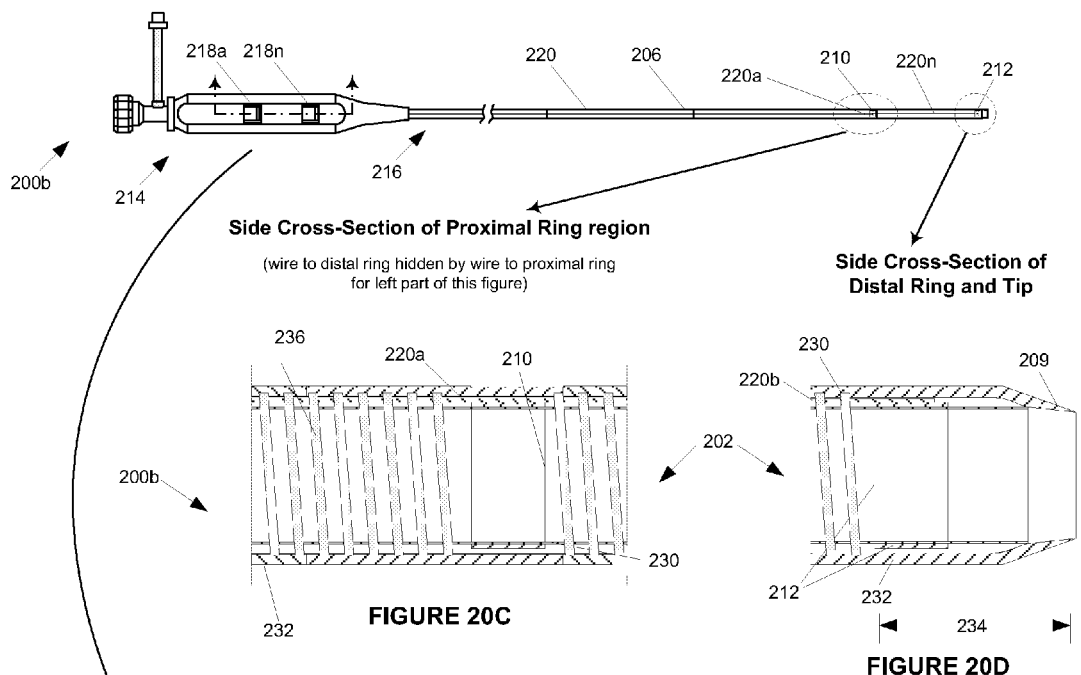
Figure 20B:
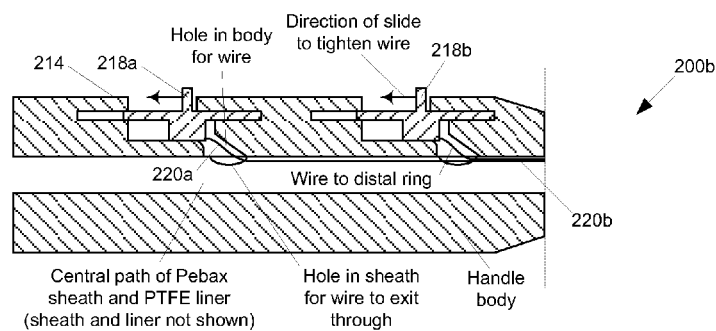

One embodiment of a steerable catheter 200a is generally illustrated in FIG. 19. The steerable catheter 200a may include shaft 206 defining at least one lumen 202. The lumen 202 may be configured to receive the dilator 34 and/or an implant (not shown). The shaft 206 may also include a plurality of segments or portions 208a-208n having different hardness or stiffness to produce the desired overall curvature. The shaft 206 may be formed from one or more suitable polymers such as, but not limited to, a polyether block amide. The shaft 206 may have a constant inner and/or outer diameter and may be made from different materials to provide the various stiffness or hardness. Alternatively, or in addition, the shaft 206 may have different inner and/or outer diameters and may be made from one or more materials. For example, the various stiffness or hardness of the shaft 206 may be provided by varying the thickness of the shaft 206 at the different segments or portions. The different hardness of the segments may provide differing degrees of bending stiffness to the steerable catheter 200a which may facilitate advancing the steerable catheter 200a into and/or out of the left ventricle 3 as well as aiming or alignment of the steerable catheter 200a.

As shown, the steerable catheter 200a may comprise three different segments 208a, 208b and 208n. The first segment 208a may be disposed proximate the distal tip 204. The first segment 208a may optionally include the tapered tip 209 and may have a length of approximately 8 inches. The tapered tip 209 may be provided to facilitate advancing the steerable catheter 200a into the percutaneous puncture site in the groin and over the dilator 34.

According to at least one embodiment, the first segment 208a may be formed of PEBAX™ 2533 having a durometer of 25 D and may have a length of approximately 4 to 6 inches. The second segment 208b may be adjacent to the first segment 208a and may have a length of approximately 2.5 inches. According to at least one embodiment, the second segment 208b may be formed of PEBAX™ 4033 having a durometer of 40 D. The third segment 208n may be adjacent to the second segment 208b and may have a length sufficiently long to extend beyond the access incision. According to at least one embodiment, the third segment 208n may be formed of PEBAX™ 7233 having a durometer of 72 D.

It should be understood that the various lengths and hardness described above for the segments 208a-208n may be adjusted or changed depending upon the circumstances of its intended use. For example, patients with larger and/or smaller hearts may require one or more of the segments to be longer or short. An important aspect of the segments 208a-208n is that the softest segment is the first segment 208a. Also, the second segment 208b is disposed approximately 4 to 6 inches from the distal tip 209. As will be explained herein, the length of the first segment 208a may generally correspond to the length between the transseptal puncture site 13 and the implantation site (e.g., the apex) in the left ventricle 3 where the curvature of the steerable catheter 200a may be greatest.

The steerable catheter 200a may also include a first steering device 210. The first steering device 210 may include a pull ring or the like which may be disposed about 1.5-4 inches from the distal end of the tip 209. The exact length of the first steering device 210 from the tip 209 may depend on the size of the patient's heart which may vary quite a bit depending on, among other things, the degree of regurgitation. For example, patients with functional mitral regurgitation often have dilated cardiomyopathy (enlarged left ventricle). According to at least one embodiment, the first steering device 210 may be located 2 inches from the tip 209.

The steerable catheter 200a may optionally include at least a second steering device 212. The second steering device 212 may include a pull ring or the like which may be disposed proximate to the distal end of the tip 209. The second or more steering devices 212 may be provided to facilitate curving or bending of the steerable catheter 200a. The first and second steerable devices 210, 212 may be configured to reduce drag during withdrawal and may also facilitate alignment or aiming of the tip 209 within the left ventricle 3. The first and second steerable devices 210, 212 may also facilitate advancement of the steerable catheter 200a over the dilator 34, through the trans septal puncture site 13, and through the left atrium 6 and down into the left ventricle 3.

The first and/or second steerable devices 210, 212 may be coupled to a handle assembly 214 which may be disposed about a proximal end 216 of the shaft 206. The handle assembly 214 may include one or more fittings and/or valves. For example, the handle assembly 214 may include a valve 215 (for example, but not limited to, a hemostasis valve or the like) and/or a fitting 217 (for example, but not limited to, a luer lock fitting or the like). The handle assembly 214 may also include one or more actuation devices 218a-218n (such as, but not limited to, knobs, sliders, or the like) coupled to the first and second steerable devices 210, 212. The actuation devices 218a-n may be configured to place the first and second steerable devices 210, 212 under tension, therefore causing the shaft 206 to deflect (e.g., curve or bend). For example, the steerable catheter 200b may include actuation devices 218a-n coupled to the first and/or second steerable devices 210, 212 by way of one or more wires or the like 220 disposed along at least a portion of the shaft 206 as generally illustrated in FIGS. 20A-20D.

By way of example, the actuation devices 218a-n may be slide distally and/or proximally within the handle assembly 214 to increase or decrease the tension placed on the wires 220. The tension in the wires 220 may asymmetrically urge/pull the first and/or second steerable devices 210, 212 (e.g., the first and/or second pull rings) to one side causing the shaft 206 to defect or curve where the wires 220 are coupled to the first and/or second steerable devices 210, 212.

Turning now specifically to FIGS. 20C-20D, the shaft 206 may optionally include an inner layer 230 configured to provide a substantially seamless inner surface of the lumen 202. The inner layer 230 may also be configured to reduce and/or minimize surface friction. According to at least one embodiment, the inner layer 230 may include PTFE or the like. The shaft 206 may also include another layer 232 configured to provide the desired stiffness. For example, the layer 232 may include Pebax™ or the like.

Optionally, the shaft 206 may include three or more sections configured to provide kink resistance, pushability, and/or flexibility. For example, the shaft 206 may include a reinforced section 234 disposed between the first steering device 210 and the second steering device 212. The reinforced section 234 may be configured to provide increased flexibility, which may facilitate navigating the shaft 206 to the left ventricle 3 and configured to provide increased kink resistance. According to at least one embodiment, the reinforced section 234 may be spiral reinforced and may have a length of 1-3 inches.

The shaft 206 may also optionally include spiral reinforced section 236 (as generally illustrated in FIGS. 19 and 20C). The spiral reinforced section 236 may extend from the first steering device 210 towards the handle assembly 214 for about 7.5 inches. The spiral reinforced section 236 may be configured to provide kink resistance when deflecting the shaft 206 using the first and/or second steerable devices 210, 212. As may be appreciated, a kink in the shaft 206 may reduce the ability of the user to locate the distal tip 209 within the left ventricle 3 and may also increase the force needed to push the implant through the lumen 202 during deployment.

The shaft 206 may also optionally include a braided reinforced section 238. The braided reinforced section 238 may extend from the proximal end of the spiral reinforced section 236 to the handle assembly 214. The braided reinforced section 238 may be configured to increase the pushability and torsional strength of the shaft 206 while reducing and/or minimizing kinking. Increasing the pushability and torsional strength and preventing kinking may be important since the length of the shaft 206 from the groin (where the steerable catheter 204 may be introduced) to the left ventricle 3 may be fairly long and involve tortuous anatomy.

Turning now to FIGS. 21-24, the effects of actuating the first and/or second steerable devices 210, 212 on the shaft 206 are generally illustrated. For example, FIG. 21 generally illustrates one embodiment of a steerable catheter 202a in which the shaft 206 is unbiased. FIG. 22 generally illustrates deflection of the distal region 240. For example, a user may actuate the second actuation device 218n (for example, but not limited to, by sliding the second actuation device 218n generally in the direction of arrow A) causing the second steerable device 212 to deflect the shaft 206 in a region 240 proximate the second steerable device 212. As may be seen, the second steerable device 212 may cause the shaft 206 to deflect and/or bend in a region 240 between the second steerable device 212 and the handle assembly 214. According to at least one embodiment, the second steerable device 212 may generally cause the shaft 206 to deflect and/or bend in a region 240 between the second steerable device 212 and the first steerable device 210. The second steerable device 212 may generally cause the shaft 206 to deflect and/or bend up to approximately 180 degrees, though angles of curvature greater than 180 degrees are also possible depending on flexibility of the shaft 206 as well as the effects of the shaft 206 needing to bend passively to accommodate the patient's anatomy. The radius of the curvature may be 1.0 inches to 2.0 inches, for example, 1.25 inches to 1.75 inches.

FIG. 23 generally illustrates deflection of the proximal region 242. For example, a user may actuate the first actuation device 218a (for example, but not limited to, by sliding the first actuation device 218a generally in the direction of arrow B) causing the first steerable device 210 to deflect the shaft 206 in a region 242 proximate the first steerable device 210. As may be seen, the first steerable device 210 may cause the shaft 206 to deflect and/or bend in a region 242 between the first steerable device 210 and the handle assembly 214. According to at least one embodiment, the first steerable device 210 may generally cause the shaft 206 to deflect and/or bend up to approximately 180 degrees, though angles of curvature greater than 180 degrees are also possible depending on flexibility of the shaft 206 as well as the effects of the shaft 206 needing to bend passively to accommodate the patient's anatomy. The radius of the curvature may be 1.0 inches to 2.0 inches, for example, 1.25 inches to 1.75 inches.

Turning now to FIG. 24, one embodiment generally illustrating the deflecting of both the first and second steering actuators 210, 210 is shown. The first and second steerable devices 210, 212 may generally cause the shaft 206 to deflect and/or bend up to approximately 180 degrees, though angles of curvature greater than 180 degrees are also possible depending on flexibility of the shaft 206 as well as the effects of the shaft 206 needing to bend passively to accommodate the patient's anatomy. The radius of the curvature may be 1.0 inches to 2.0 inches, for example, 1.25 inches to 1.75 inches, however, the exact range of the radius may depend upon the location of the first and second steerable devices 210, 212 as well as the flexibility of the regions 240, 242.

Figure 25:
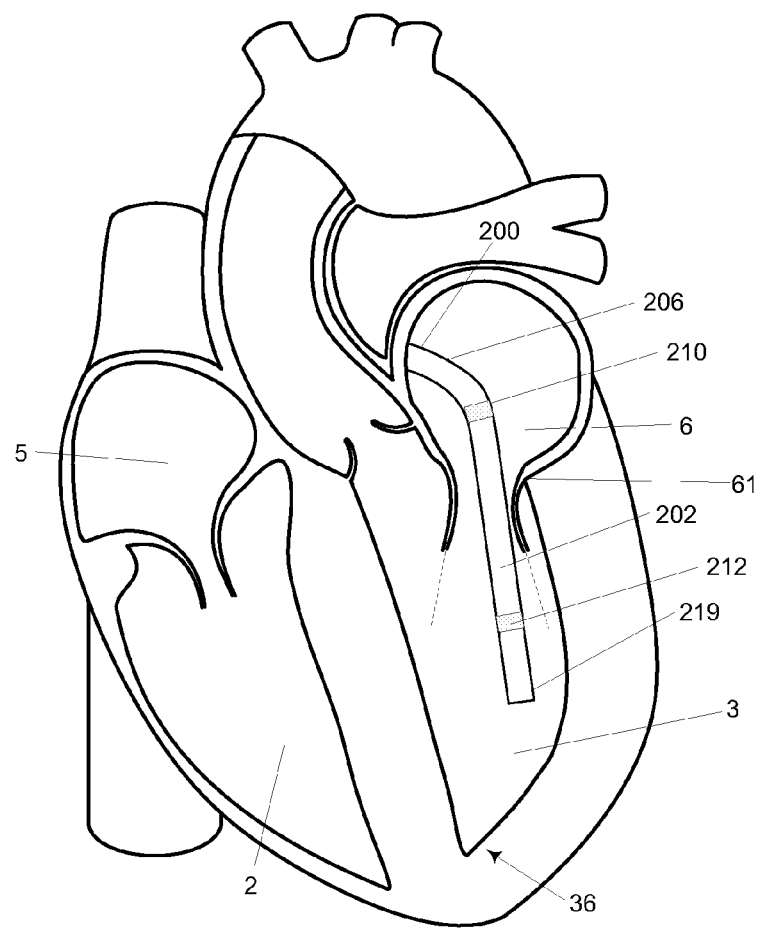
FIG. 25 illustrates a perspective view of an embodiment of a steerable catheter advanced in the left ventricle with an implant loaded consistent with the present disclosure.
Figure 26:
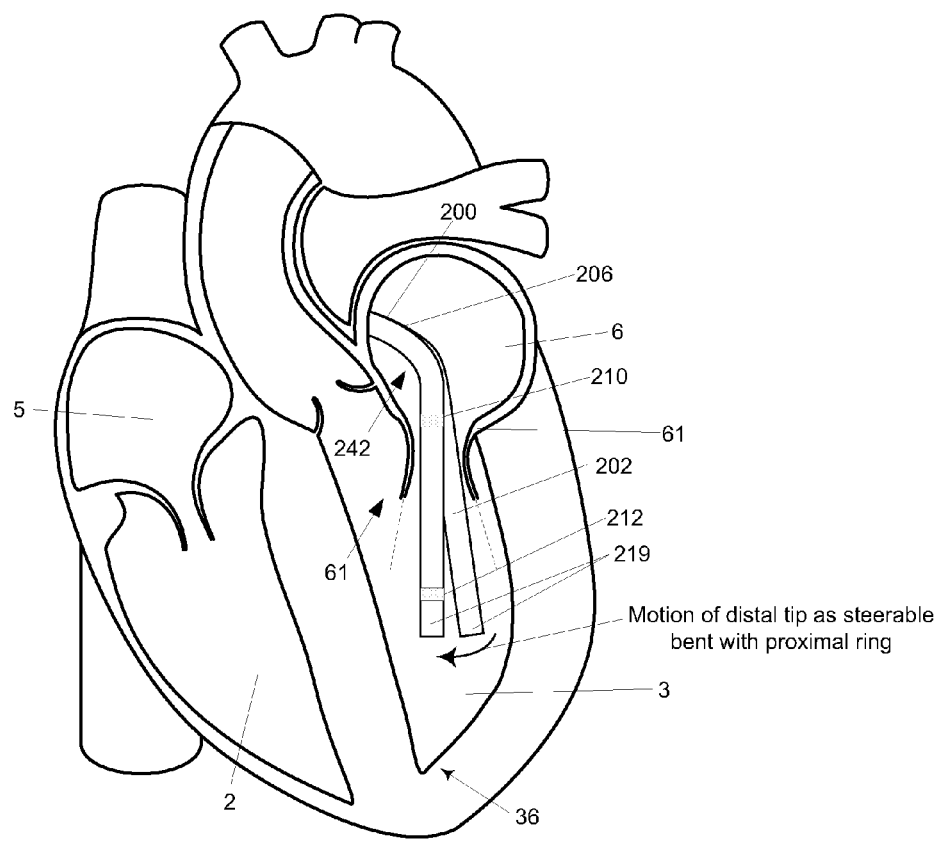
FIG. 26 illustrates a perspective view of an embodiment of a steerable catheter being aimed or aligned with the implant site consistent with the present disclosure.

Turning now to FIG. 25, the dilator 34 has been removed from the steerable catheter 200 and the implant (not shown) may be advanced through the lumen 202 proximate to the distal end 219. By actuating the first steerable actuator 210, the user may aim and/or align the distal end segment and/or distal tip 219 of the steerable catheter 200 to the desired location within the left ventricle 3 where it is desired to anchor or secure the implant by deflecting the shaft 206 in the region 242 as generally illustrated by the arrows in FIG. 26 representing the deflection of the steerable catheter 200. Fluoroscopic and/or echo guidance may be used to facilitate aiming of the steerable catheter 200 within the left ventricle 3.

As may be appreciated, the location of the first steerable actuator 210 and the region 242 along the shaft 206 may generally correspond to the position of the shaft 206 within the left atrium 6 and/or the left ventricle 3 proximate to the mitral valve 6. Ideally, the first steerable actuator 210 would reside somewhere between the annulus of the valve and the valve leaflets. This would provide for the distal section 234 to be pointed relatively straight at the desired anchor location. The differing lengths of the first section 234 may compensate for the variations in the patients' valve to apex length, although anchoring directly in the apex may not always be the desired location. In FIG. 26 the illustrated bend in the catheter may be closer to the valve 6.

Figure 27:
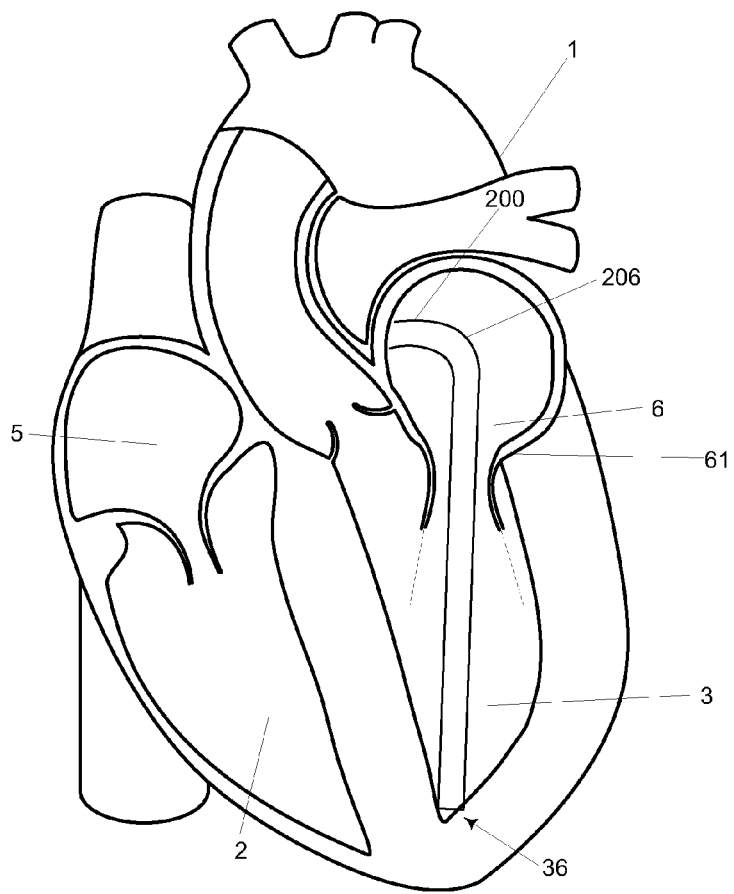
FIG. 27 illustrates a perspective view of an embodiment of a steerable catheter advanced to the implant site consistent with the present disclosure.

Once the steerable catheter 200 has been positioned through the mitral valve 61, it may be advanced to an implant location within the left ventricle 3 (for example, but not limited to, the apex 36), as generally illustrated in FIG. 27. A heart valve implant may then be delivered to the implant location using one or more delivery catheters and/or pushers advanced through the lumen of steerable catheter 200, as well be described below.

Figure 28A:
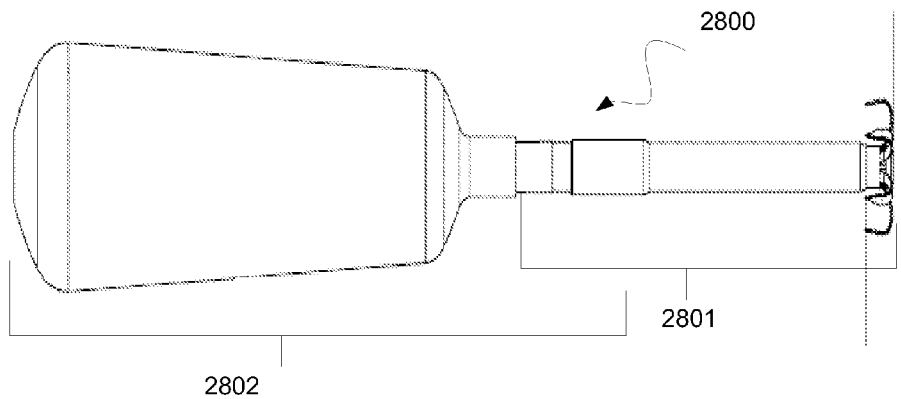
FIGS. 28A and B illustrate a side outline view and perspective view of a heart valve implant consistent with the present disclosure.
Figure 28B:
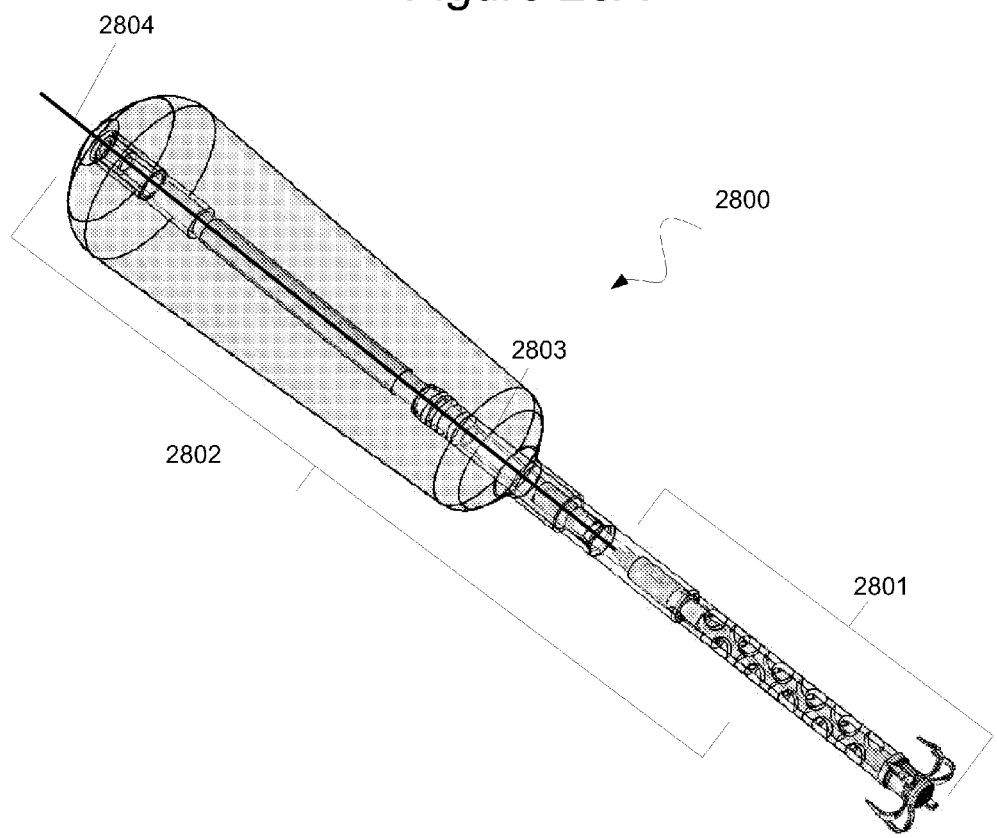

Reference is now made to FIGS. 28A and 28B, wherein an example heart valve implant illustrated. As shown, implant 2800 includes anchor assembly 2801 and balloon spacer assembly 2802. A proximal end of anchor assembly 2801 may be coupled to a delivery guide wire 2804, as generally shown in FIG. 28B and as will be described later. In general, at least a portion of the heart valve implant 2800 may be configured to be disposed proximate a mitral valve such that the implant may interact and/or cooperate with at least a portion of the mitral valve to reduce and/or eliminate excessive regurgitation through the mitral valve.

As will be discussed in detail below, anchor assembly 2801 and balloon spacer assembly 2802 may be configured to be individually delivered and assembled proximate an implant site within a heart. The implant site may be selected such at least a portion of heart valve implant 2800 is located proximate to the mitral valve. In addition, the heart valve implant 2800 may have an overall size and shape configured to accommodate, at least in part, a patient's anatomy, etiology of valve regurgitation, and/or the limitations of the implant delivery system. In this regard, at least one portion of the heart valve implant when deployed may have a dimension that is larger than the internal cross sectional dimensions of steerable catheter 200 and/or an implant delivery catheter/pusher. In this way, heart valve implant 2800 may be constructed within the heart to have an external size, contour, and shape based on, at least in part, the patient's anatomy and etiology of the regurgitate valve. As such, the heart valve implants according to one aspect of the present disclosure may provide an enhanced sealing surface for the leaflets of the mitral valve to reduce and/or eliminate excessive regurgitation.

Figure 29:
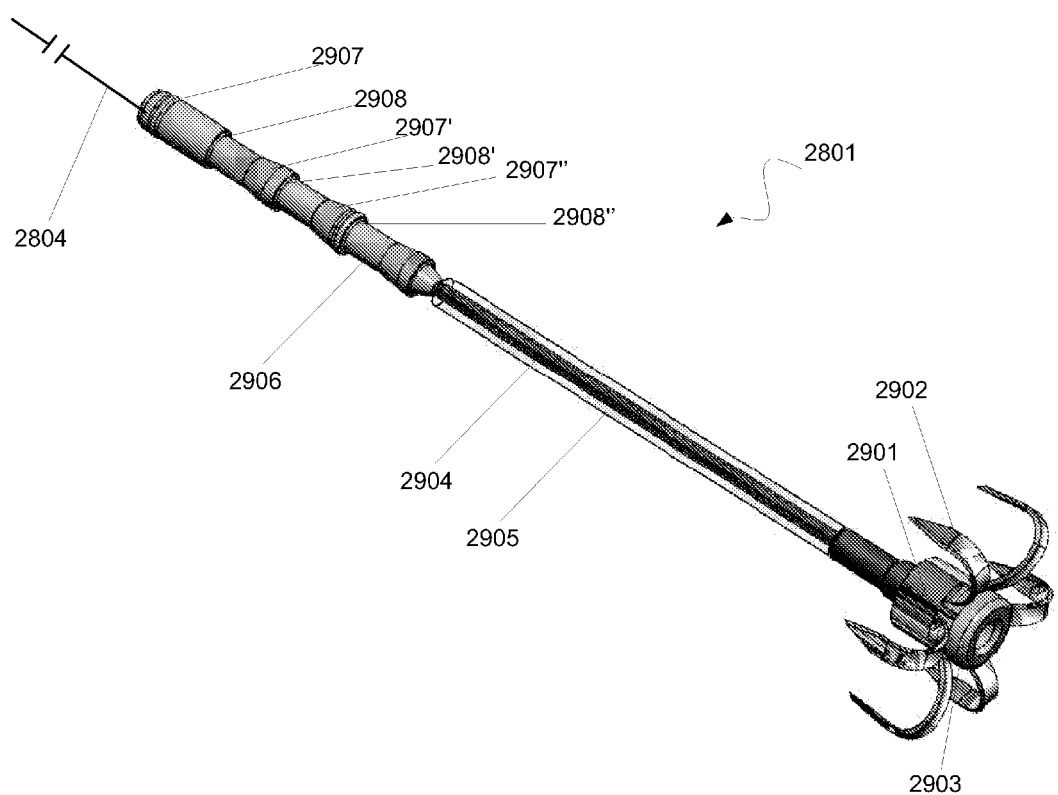
FIG. 29 illustrates a perspective view of an anchor assembly of a heart valve implant consistent with the present disclosure.
Figure 30:
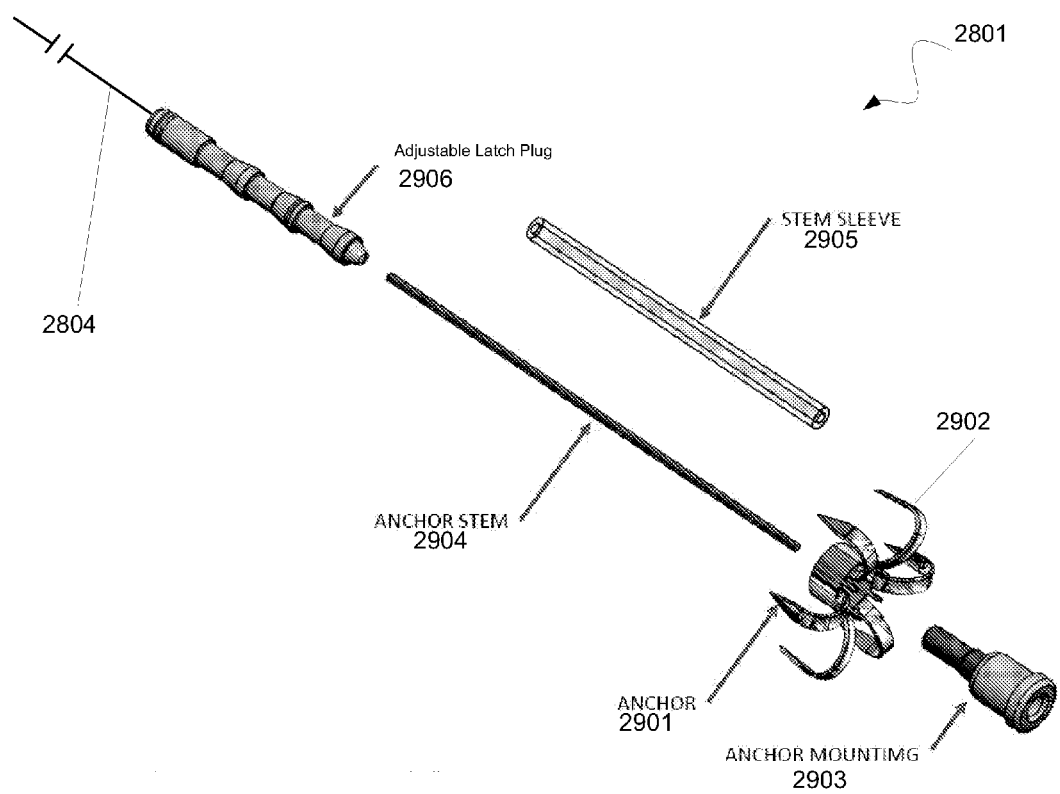
FIG. 30 illustrates an exploded view of an anchor assembly of a heart valve implant consistent with the present disclosure.

FIGS. 29 and 30 respectively illustrate perspective and exploded views of an anchor assembly 2801 consistent with the present disclosure. As shown, the anchor assembly 2801 includes anchor 2901. In the illustrated embodiment, anchor 2901 includes a plurality of barbs 2902, which may be configured to couple, attach or otherwise secure anchor assembly 2801 (and heart valve implant 2800) to native coronary tissue, such as the coronary tissue proximate to the apex of a heart. In some embodiments, barbs 2902 may be configured to be deployable from an anchor retention sheath of an anchor delivery catheter, as will be described later in connection with FIGS. 31A-31C. In such instances, barbs 2902 may be configured to engage coronary tissue proximate to a distal end of the anchor delivery catheter and draw anchor 2901 into such tissue.

Barbs 2902 may be made from any suitable material, such as stainless steel, a shape memory alloy (e.g., a nitinol (NiTi) shape memory alloy), or the like. Without limitation barbs 2902 and the body (not labeled) of anchor 2901 are preferably formed from a shape memory alloy such as a nitinol.

In addition to barbs 2902, anchor 2901 includes anchor mount 2903. In general, anchor mount 2903 is configured to couple or otherwise attach anchor 2901 to anchor stem 2904. Coupling of these components may be achieved mechanically, with an adhesive, via thermal bonding, combinations thereof, and the like. Without limitation, the anchor mount is preferably configured mechanically engage anchor stem 2904. For example, anchor mount 2903 may include a threaded proximal portion that is configured to threadably engage with corresponding threads on a distal portion of the anchor stem 2904.

Anchor mount 2904 may be manufactured from any suitable material, such as but not limited to polymers such as a polyurethane silicone blend. One example of such a blend is the material sold under the trade name ELAST-EON™ by the company AorTech.

Anchor stem 2904 generally functions to provide an offset between anchor 2901 and balloon spacer assembly 2802. Anchor stem 2904 may perform this function independently or in conjunction with latch plug 2906, as will be described in detail later with respect to FIGS. 34A-34E.

In any case, anchor stem 2904 includes a distal end coupled to anchor 2901, and a proximal end coupled to latch plug 2906. Anchor stem 2904 may be coupled to latch plug 2906 in any suitable manner, including mechanically, chemically, with an adhesive, in another manner, combinations thereof, and the like. In some embodiments, the proximal portion of anchor stem 2904 may be threaded and configured to engage with corresponding threads in a distal stem receive portion (not shown in FIG. 29) of latch plug 2906. This concept is shown in FIG. 31B, wherein it is shown that latch plug 2906 includes stem receive portion 3102 which threadably engages a threaded proximal end of anchor stem 2904.

Anchor stem 2904 may be manufactured from any suitable material, including but not limited to stainless steel, nitinol, titanium, another biocompatible material, combinations thereof, and the like. Without limitation, anchor stem 2904 is manufactured from a nitinol.

As illustrated, anchor assembly 2801 further includes stem sleeve 2905. In general, stem sleeve 2905 may function to protect or otherwise insulate stem 2904 from exposure to the environment within the heart of a patient, and vice versa. More specifically, stem sleeve 2905 may insulate anchor stem 2905 from exposure to blood or other bodily fluid which may cause anchor stem 2905 to breakdown or otherwise degrade over time. In this same way, stem sleeve 2905 may also reduce or limit the occurrence of blood clots, which may have an enhanced tendency to form if the blood of a patient were to directly contact anchor stem 2904.

Stem sleeve 2905 may be manufactured from any suitable biocompatible material, including biocompatible polymers such as silicone, polytetrafluoroethylene (PTFE), a biocompatible polyester, combinations thereof, and the like. Without limitation, stem sleeve 2905 is preferably formed from a low durometer silicone.

Latch plug 2906 is generally configured to enable adjustments to be made to the amount of offset between anchor 2901 and balloon spacer assembly 2802. In this regard, latch plug 2906 may include one or a plurality of contoured regions (not labeled) which may be configured to engage corresponding locking portions of one or more latches in a balloon spacer assembly, as will be discussed later. The number and configuration of the contoured regions may vary widely, and may be selected to accommodate a patient's anatomy, the etiology of a faulty heart valve, combinations thereof, and the like. In the illustrated embodiment, latch plug 2906 includes three contoured regions, thus enabling it to be coupled to a latch of a balloon assembly in at least three positions. As may be appreciated and as will be discussed below, these features may permit the length of heart valve implant 2800 to be adjusted while it is present inside the heart of a patient.

As also shown, latch plug 2906 may include a proximal portion that is coupled or otherwise attached to delivery guide wire 2804. Coupling of delivery guide wire 2804 and the proximal portion of latch plug 2906 may be achieved in any suitable matter. For example, delivery guide wire 2804 and latch plug 2906 may be mechanically and reversibly coupled to one another. In some embodiments, the proximal end of latch plug 2906 may be threaded and configured to threadably engage a corresponding threaded distal portion of delivery guide wire 2804. This concept is shown in FIG. 31B, wherein it is shown that latch plug 2906 includes guide wire receive portion 3103 which threadably engages a distal end of delivery guide wire 2804.

Anchor assembly 2801 may be configured such that it may be deliverable to an implant site through a lumen of steerable catheter 200. In this regard, all or a portion of anchor assembly 2801 may be configured to be collapsed and retained within an anchor retention sheath that is insertable into an anchor delivery catheter having an outside diameter that is less than the inside diameter of a lumen of steerable catheter 200. The anchor delivery catheter (including the loaded anchor retention sheath at a distal end thereof) may thus be introduced into the lumen of the steerable catheter and advanced to the implant site. Accordingly, the anchor delivery catheter may be constructed to have sufficient flexibility to enable it to navigate through the lumen of the steerable catheter to an implant site.

Figure 31A:
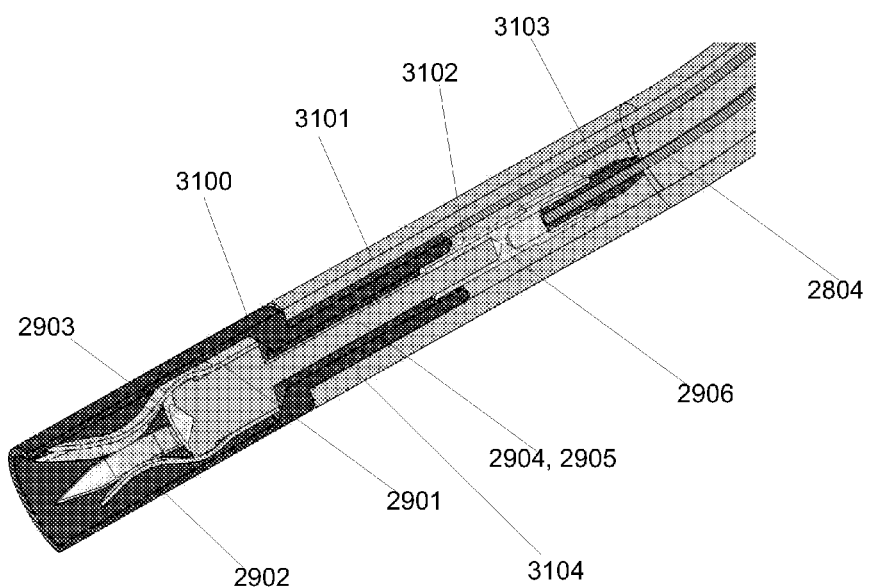
FIG. 31A illustrates cross sectional perspective view of an anchor assembly loaded within an anchor delivery system consistent with the present disclosure.
Figure 31B:
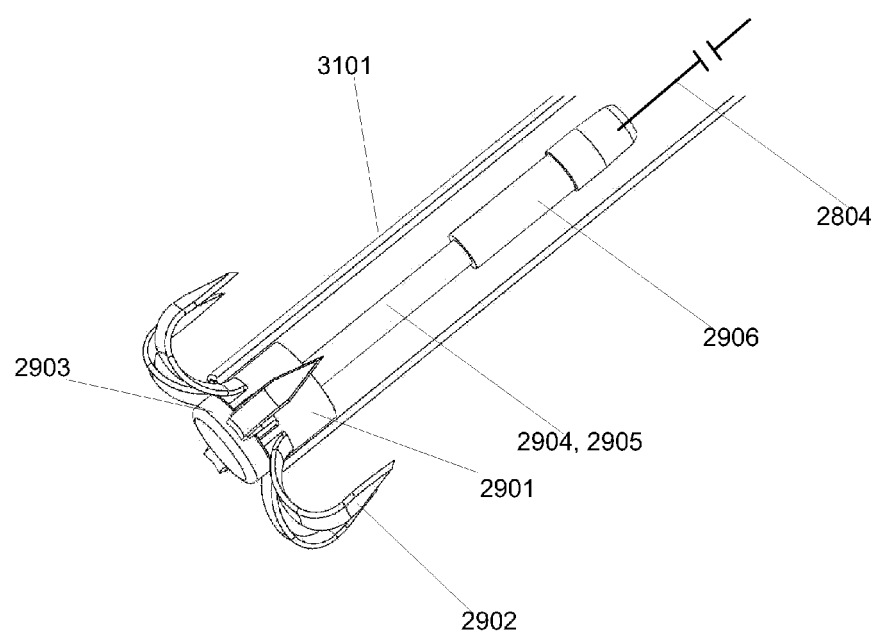
FIG. 31B illustrates a perspective view of an embodiment of an anchor delivery catheter including an anchor advanced through a steerable catheter to an implant site consistent with the present disclosure.

Reference is now made to FIG. 31A, which depicts a cross sectional perspective view of an anchor assembly 2801 loaded into an anchor delivery system consistent with the present disclosure. In particularly, anchor assembly 2801 may be loaded into an anchor retention sheath 3100, which itself may be inserted into a lumen at a distal end of an anchor delivery catheter 3101 consistent with the present disclosure.

As shown, anchor 2901 may be loaded into anchor retention sheath 3100 such that barbs 2902 are collapsed forward into a constrained loading position. In the constrained loading position, barbs 2902 may exert significant outward mechanical force against the walls of anchor retaining sheath 3101. Accordingly, the walls (not labeled) of anchor retention sheath 3100 may be configured to withstand such outward forces, such that anchor assembly 2801 may be retained in a collapsed state as it is delivered to an implant site through the lumen of steerable catheter 200. In this regard, anchor retention sheath 3100 may be manufactured from a material that can withstand significant outward forces that may be imparted by barbs 2902 in the constrained loaded position. Non-limiting examples of such materials include stainless steel and other biocompatible metals and metal alloys.

To facilitate delivery of the anchor assembly to a surgical site, anchor retention sheath 3100 may include a proximally extending insert portion 3104, which may be configured for insertion into a distal end of a lumen of anchor delivery catheter 3101. More particularly, insert portion 3104 may be configured upon insertion to mechanically or otherwise engage with the interior walls of a lumen of implant delivery catheter 3101, thereby retaining anchor retention sheath 3100 on a distal end of anchor delivery catheter 3101. This concept is illustrated in FIG. 31A, wherein proximally extending insert portion 3104 of anchor retention sheath 3100 is depicted as inserted into a distal end of a lumen of anchor delivery catheter 3101. It is noted that in the illustrated example, insert portion 3104 is relatively short, as compared to the illustrated length of anchor assembly 2801. It should be understood that this illustration is for example only, and that the length of insert portion 3104 may be longer or shorter, e.g., depending on the characteristics of the anchor retention sheath, anchor assembly 2801, and/or anchor delivery catheter 3101.

Anchor delivery catheter 3101 may be configured to facilitate the delivery of anchor retention sheath 3100 including loaded anchor assembly 2801 to an implant site via a lumen of steerable catheter 200. In this regard, anchor delivery catheter 3101 may be manufactured from one or more materials having sufficient flexibility to enable anchor retention sheath 3100 to push or otherwise advance anchor assembly 2801 through the lumen of steerable catheter 200. As non-limiting examples of materials that may be used to form anchor delivery catheter 3101, mention is made of biocompatible polymers such as PTFE, polyurethane, biocompatible polyester, polyether ether ketone (PEEK) combinations thereof, and the like.

Figure 32:
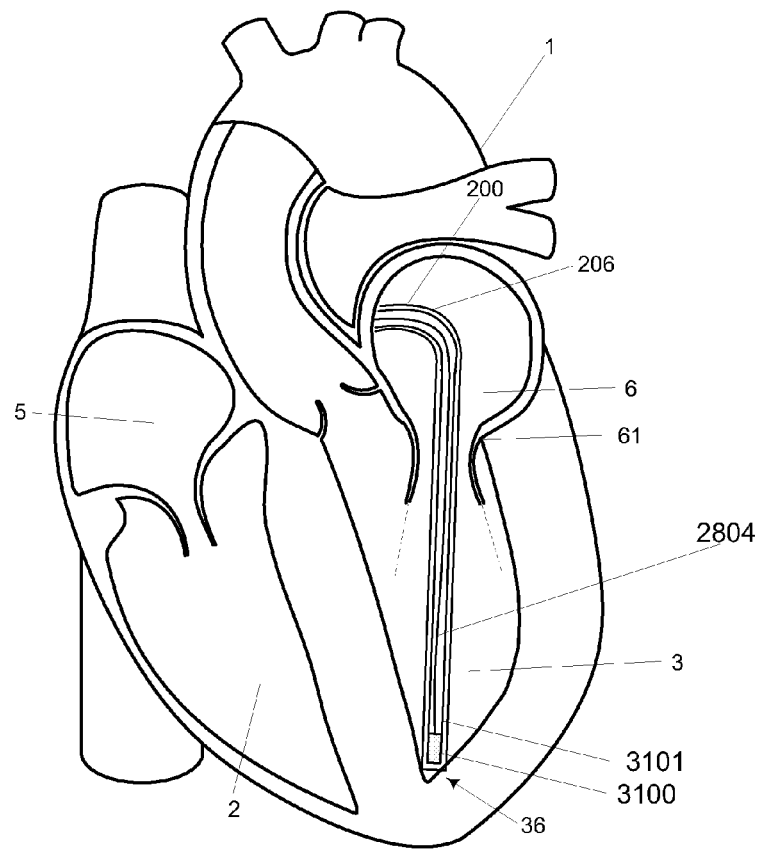
FIG. 32 illustrates an example of an anchor delivery catheter with an anchor retention sheath extended through a lumen of a steerable catheter to an implant site consistent with the present disclosure.

As further shown in FIG. 31A, anchor assembly 2801 may loaded in anchor retention sheath 3100 such that delivery guide wire 2804 coupled to guide wire receive portion 3103 of latch plug 2906 extends proximally therefrom. Delivery guide wire 2804 may further proximally extent through a lumen of anchor delivery catheter 3101 and ultimately to a region to the exterior of a patient. As will be described later, delivery guide wire may be used to facilitate the positioning and coupling of balloon spacer assembly 2802 with anchor assembly 2801 after anchor assembly 2801 is deployed from anchor retention sheath 3100 to engage native coronary tissue. This concept is illustrated in FIGS. 31A and 32, wherein delivery guide wire 2804 is depicted as extended proximally through a lumen (not labeled) of anchor delivery catheter 3101.

Once anchor assembly 2801 is loaded in anchor retention sheath 3100, anchor retention sheath may be advanced through a lumen of steerable catheter 200 to an implant site. This concept is illustrated in FIG. 32, which depicts an example of an anchor retention sheath 3100 disposed at the end of an anchor delivery catheter 3101 which has been advanced through a lumen of steerable catheter 200 to an implant site (not labeled) at a distal end of steerable catheter 200. Advancement of the anchor retention sheath 3100 through the lumen of steerable catheter 200 may be accomplished by pushing anchor retention sheath 3100 with the distal end of anchor deliver catheter 3101.

Once a loaded anchor retention sheath 3100 is present at a surgical site, anchor assembly 2801 may be deployed. In this regard, anchor assembly 2801 may be pushed out of anchor retention sheath 3100 (e.g., by the exertion of force by delivery guide wire 2804), so as to release barbs 2902 from the constrained loaded position. As barbs 2902 are released from the constrained loaded position, they may spring back to an expanded deployed position, such as the position shown in FIG. 29. This concept is illustrated in FIG. 31B, which depicts anchor assembly 2801 as it is initially deployed from anchor retention sheath 3100. As shown barbs 2902, now free of constraint by anchor retention sheath 3100, have sprung back to an expanded deployed position.

In some embodiments, deployment of anchor assembly 2801 from anchor retention sheath 3100 may occur in a manner such that barbs 2902 engage native coronary tissue as anchor assembly 2801 is deployed. More specifically, when anchor assembly 2801 is initially deployed from anchor retention sheath 3100, barbs 2902 may engage and/or enter native coronary tissue prior to springing back to an expanded deployed position. In such instances, the spring like motion of barbs 2902 when deployed may cause them to embed in native coronary tissue. In some instances, barbs 2902 may act to draw anchor 2901 towards the native coronary tissue, which may cause bards 2902 to further embed within the tissue. This may enhance the engagement and retention of anchor assembly 2801 to the native coronary tissue. The deployment of anchor assembly 2801 may then be completed by fully pushing anchor assembly 2801 out of anchor retention sheath 3100. Anchor retention sheath 3100 and anchor delivery catheter 3101 may then be withdrawn, leaving delivery guide wire 2804 extending from guide wire receive portion 313 through the lumen of steerable catheter 200. A balloon spacer assembly consistent with the present disclosure may then be advanced through lumen of steerable catheter 200 and over delivery guide wire 2804 to a position proximate to the deployed anchor assembly.

Figure 33A:
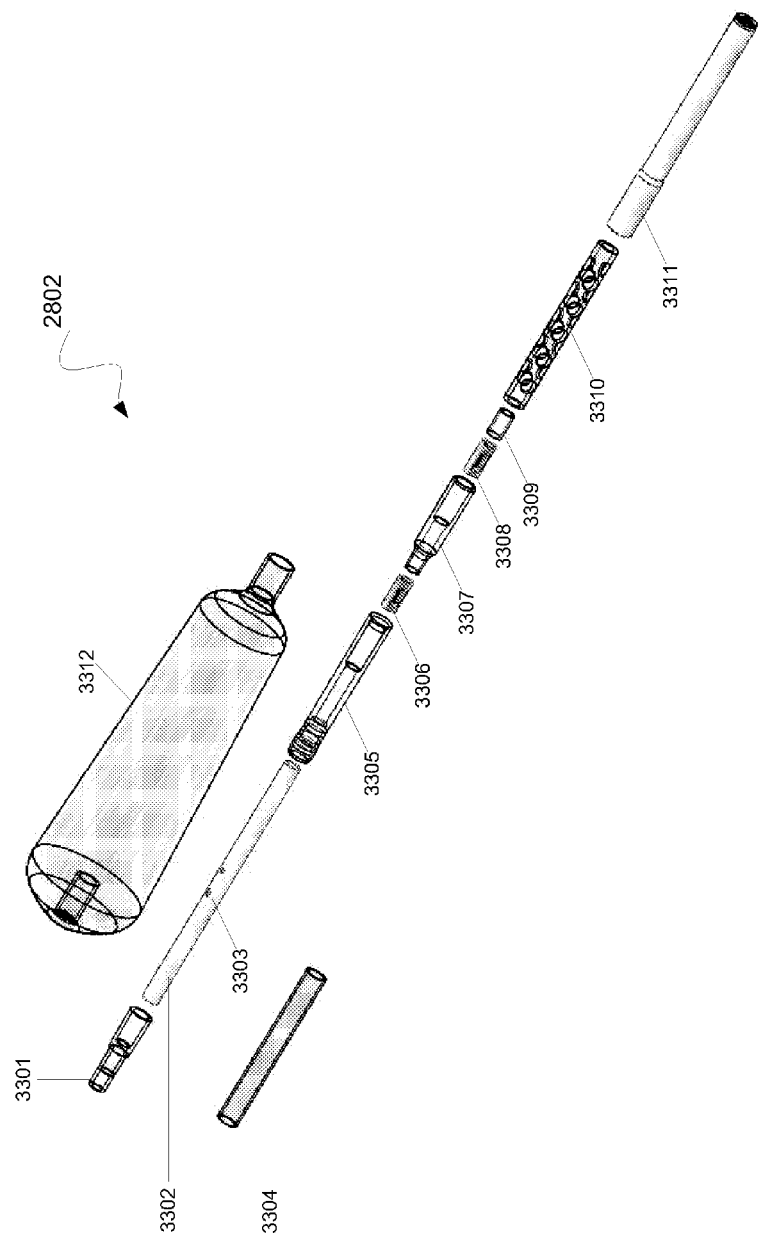
FIG. 33A illustrates an exploded view of a balloon assembly consistent with the present disclosure.
Figure 33B:
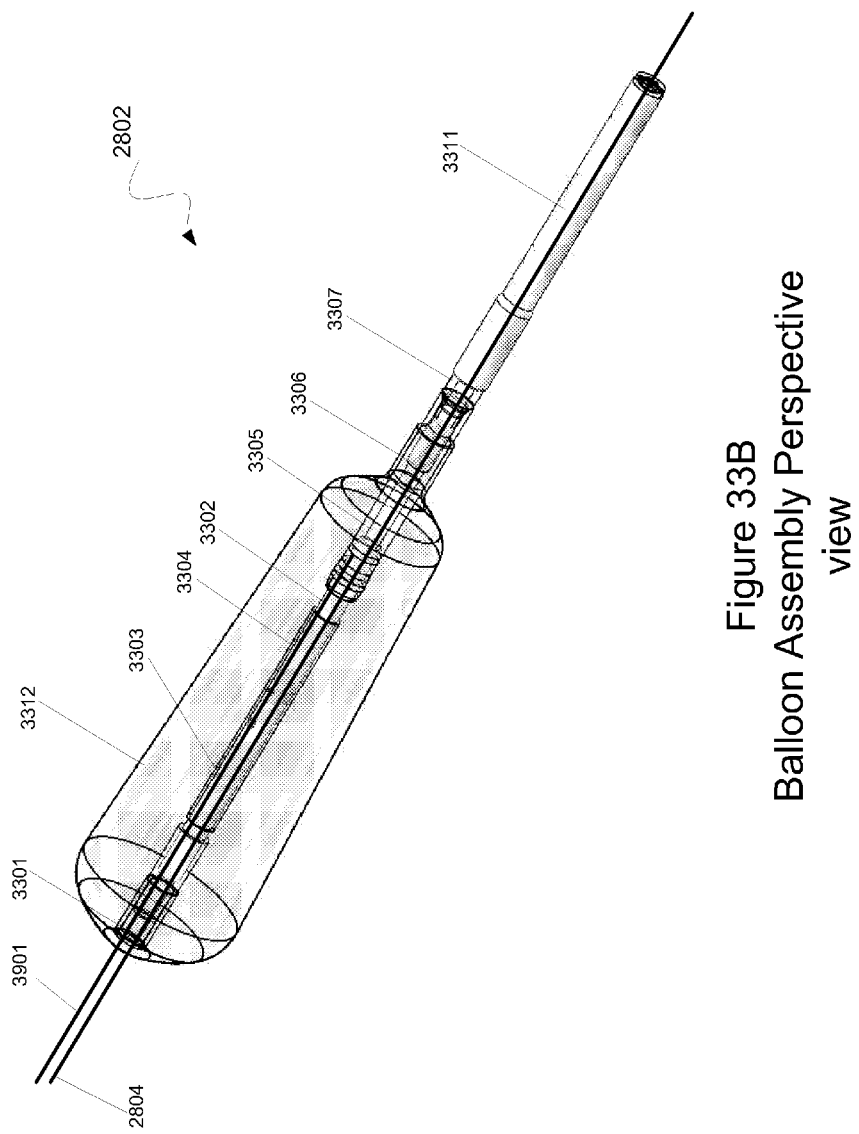
FIG. 33B illustrates a perspective view of a balloon assembly consistent with the present disclosure.

Reference is now may to FIGS. 33A and 33B, which illustrate exploded and perspective views of an example balloon spacer assembly 2802 consistent with the present disclosure. As shown, balloon spacer assembly 2801 includes proximal end cap 3301. Proximal end cap is generally configured to hermetically seal the proximal end of balloon 3312 (as generally shown in FIG. 33B), and to couple or otherwise attach balloon spacer assembly to a pusher assembly, as will be described later. Proximal end cap 3301 also includes a lumen through a central portion thereof, which is of sufficient diameter to allow delivery guide wire 2804 and a valve wire 3801 (described later) to freely pass there through. Proximal end cap 3301 may be formed from any suitable biocompatible materials, such as one or more biocompatible polymers or polymer blends. One example of a suitable polymer blend that may be used to form proximal end cap is the polyurethane silicone blend sold by AorTech under the trade name ELASTEON™.

The distal end of proximal end cap 3301 may be configured to couple with central tube 3302 of balloon spacer assembly 2801, as generally shown in FIG. 33B. Coupling of proximal end cap 3301 to central tube 3302 may be accomplished in any manner. For example, proximal end cap 3301 may be coupled to central tube 3302 mechanically, with an adhesive, with a heat bond, or a combination thereof. In the case of adhesive bonding, the proximal portion of central tube may be etched prior to the application of adhesive. Such etching may enhance or strengthen the adhesive bond with central tube 3302, particularly if central tube 3302 is manufactured from a material such as PTFE.

Like proximal end cap 3301, central tube 3302 may include lumen extending from a distal portion to a proximal portion thereof. The lumen of the central tube may be of sufficient diameter to allow delivery guide wire 2804 and a valve wire 3801 (described later) to freely pass there through. The lumen of central tube 3302 may align with the lumen of proximal end cap 3301 when such components are coupled to one another. As a result, delivery guide wire 2804 and valve wire 3801 may freely extend from guide wire receive portion 3103 of latch plug 2906 though the lumen of central tube 3302, through the lumen of proximal end cap 3301 and into a lumen of a pusher catheter coupled to proximal end cap 3301.

As will be described in detail later, central tube may be configured (alone or in connection with other components) to enable the filling of balloon 3312 with a fluid. In this regard, central tube 3302 may include one or more valves 3303 formed in a surface thereof. For example, central tube 3302 may include one or more valve openings such as proximal valve opening 3303' and distal valve opening 3303" illustrated in FIG. 39. Such openings may facilitate the flow of fluid (e.g., saline, another type of fluid, or the like) introduced into the lumen of central tube 3302 into and out of balloon 3312. Valve 3303 may perform this function in conjunction with one or more additional components, such as valve sleeve 3304 and a valve wire, such as valve wire 3801 shown in FIGS. 38A-D and FIG. 39.

Valve sleeve 3304 of balloon spacer assembly 2801 is generally configured to snugly envelope the outer circumference of central tube 3302, as generally shown in FIG. 33B. Accordingly, valve sleeve 3304 may be manufactured from a resiliently deformable material that is capable of snugly engaging the outer surface of central tube 3302. By way of example, valve sleeve 3304 may be manufactured from a low durometer silicone, which may have material properties that allow valve sleeve 3304 to snugly deform around central tube 3302. Of course, such material is exemplary only, and other suitable materials may be used to form valve sleeve 3304. In any case, a portion of valve sleeve 3304 may be adhered or otherwise bonded to central tube 3302 at a position proximal to proximal to valve 3303 and its associate openings.

As will be described later in conjunction with FIGS. 38A-D and 39, valve sleeve 3304 may act as a plug for either or both proximal valve opening 3303' and distal valve opening 3303". The "plug" formed by valve sleeve 3304 may be opened by a valve wire, such as valve wire 3801 shown in FIGS. 38A-D and 39. For the sake of illustration and ease of understanding, FIGS. 33A and 33B illustrate central tube 3302, valve 3303 and valve sleeve 3304, but omit a valve wire, such as valve wire 3801. As such, valve 3303 in FIG. 33B may be understood to be in a locked position, wherein valve sleeve 3304 snugly engages the surface of central tube 3302 and effectively plugs proximal and distal valve openings 3303' and 3303".

While various FIGS. depict valve 3303 as including two valve openings, greater or fewer openings may be employed. For example, valve 3303 may include 3, 4, 5 or more holes, provided that such holes may be adequately sealed by valve sleeve 3304, and may be opened by one or more valve wires. Similarly, central tube 3302 may include more than one valve 3303 formed therein. For example, central tube 3302 may include 2, 3, 4, 5, or more valves formed therein. In such instances, each valve may include corresponding proximal and distal valve openings, as well as corresponding valve wires.

As further shown in FIGS. 38A and B, balloon spacer assembly 2801 includes latch housing 3305, proximal latch 3306, latch spacer 3307, distal latch 3308, and distal plug 3309. Like central tube 3302, each of these components includes a lumen extending there through, each of which may be appropriately sized to permit the free passage of delivery guide wire 2804. In addition, the interior of each of these components may be configured to sealining engage with a outer surface features of a latch plug of an anchor assembly consistent with the present disclosure, such as latch plug 2906.

In addition, these components may be configured to couple with one another so as to form a unitary latch assembly, as generally depicted in FIG. 38B. In this regard, the lumen in a distal portion of latch housing 3305 may be sized or otherwise configured to receive proximal latch 3306 and a proximal portion of latch spacer 3307 therein. Similarly, the lumen in a distal portion of latch spacer 3307 may be sized or otherwise configured to receive distal latch 3308 and distal plug 3309 therein. Once those components are assembled as described above, they may be heat bonded or otherwise fixedly coupled to one another (e.g., with an adhesive), so as to form a unitary latch assembly.

Latch housing 3305, latch spacer 3307, and distal plug 3309 may be manufactured from any suitable material, such as a biocompatible polymeric material. In some embodiments, each of these components is formed from a polyurethane silicone blend, such as the blend sold under the trade name ELAST-EON™ by AorTech.

As will be described in detail later, proximal and distal latches 3306, 3308 may be configured to resiliently engage one or more contoured portions of a latch plug of an anchor assembly, such as contoured portions of latch plug 2906 shown in FIG. 29. In this regard, proximal and distal latches 3306 and 3308 may be formed from any material capable of sufficiently engaging and retaining a latch plug, while withstanding forces that may be applied to heart valve implant 2800 when implanted in a heart. Non-limiting examples of suitable materials that may be used to form proximal and distal latches 3306, 3308 include stainless steel, titanium, shape memory alloys such as a nickel titanium shape memory alloy (e.g., nitinol), combinations thereof, and the like. Without limitation, proximal and distal latches 3306, 3308 are preferably formed from a shape memory alloy such as nitinol.

In some embodiments, proximal and distal latches 3306, 3308 may be formed from a body temperature activated nitinol. In those embodiments, latches 3306, 3308 may be configured to releasably engage a latch plug of an anchor assembly. This may allow for readjustment (in particular lengthening) of the heart valve implant after it is implanted in a heart. For example, if proximal and distal latches 3306, 3308 are formed from a body temperature activated nitinol, such latches may be configured to open after in response to cooling (e.g., with cold saline introduced via proximal end cap 3301) or through another mechanism. Once opened, a latch plug previously engaged by one or both of latches 3306, 3308 may be moved distally, thereby lengthening heart valve implant 2800.

With further reference to FIGS. 33A and 33B, balloon spacer assembly also includes pledget support 3310 and pledget 3311. Pledget support 3310 may be coupled by heat binding or an adhesive to all or a portion of the latch assembly made up of latch housing 3305, proximal latch 3306, latch spacer 3307, distal latch 3308, and distal plug 3309 discussed above. In particular, pledget support 3310 may be bonded or otherwise coupled to the latch assembly so as to be disposed over at least a portion of proximal and/or distal latches 3306 and 3308. Pledget 3311 may be heat bonded or otherwise coupled to pledget support 3310.

As shown in FIGS. 33A and 33B, pledget support 3310 includes a lumen (not labeled) there through. As will be discussed later, the lumen of pledget support 3310 may be configured to receive latch plug 2906 of anchor assembly 2801 therein as anchor assembly 2801 is coupled to balloon spacer assembly 2802. In some embodiments pledget support 3310 and pledget 3311 may individually or collective act to apply a compressive force against latch plug 2906 and proximal and/or distal latches 3306, 3308 with which latch plug 2906 may be engaged. In this way, pledget support 3310 and/or pledget 3311 may apply an inward force that may resist proximal movement of latch plug 2906 through one or both of proximal and distal latches 3306, 3308. In some embodiments, the inward force applied by pledget support 3310 and/or pledget 3311 may be sufficient to resist, limit, or prevent unwanted proximal movement of latch plug 2906 through proximal and/or distal latches 3306, 3308 after heart valve implant 2800 is implanted in a heart of a patient.

In some embodiments, pledget support 3310 may formed from a biocompatible polymer, such as silicone another biocompatible elastomeric composition. In such instances, a plurality of holes may be formed in pledget support 3310 so as to cause the material to act as a polymer "spring" that applies an inward force to all of a portion of the latch assembly. This concept is illustrated in FIG. 33A, wherein pledget support 3310 is depicted as including a plurality of holes formed therein.

As noted previously, pledget 3311 may be heat bonded or otherwise adhered to pledget support 3310. Any suitable material may be used to form pledget 3311. For example, pledget 3311 may be made of or include a biocompatible fabric such as Dacron, an expanded PTFE fabric such as a GORE-TEX® fabric, an implantable polyester fabric, combinations thereof and the like.

As noted previously, balloon spacer assembly includes balloon 3312. Balloon 3312 is generally configured to define a cavity for receipt of a filling fluid (e.g., saline, air, another fluid, etc.), which may be introduce through valve 3303. As shown in FIGS. 33A and B, balloon 3312 may sealably engage proximal end cap 3301 and one or more components of the latch assembly described above, so as to form a sealed chamber with central tube 3303 extending there through. In this regard, balloon 3312 may be bonded to other components of balloon assembly 2801 in any suitable manner, including heat bonding, adhesive bonding, chemical bonding, or the like. Balloon 3312 may be formed from any suitable biocompatible material that is capable of being deflated for delivery through a catheter and inflated within a heart to an expanded fluid filled configuration. Non-limiting examples of suitable materials for forming balloon 3312 include PTFE, implantable polyesters, polyurethane silicone blends, combinations thereof, and the like. Without limitation, balloon 3312 is preferably formed from a polyurethane silicone blend, such as the polyurethane silicone blend sold under the trade name ELAST-EON™ by AorTech.

Figure 39:
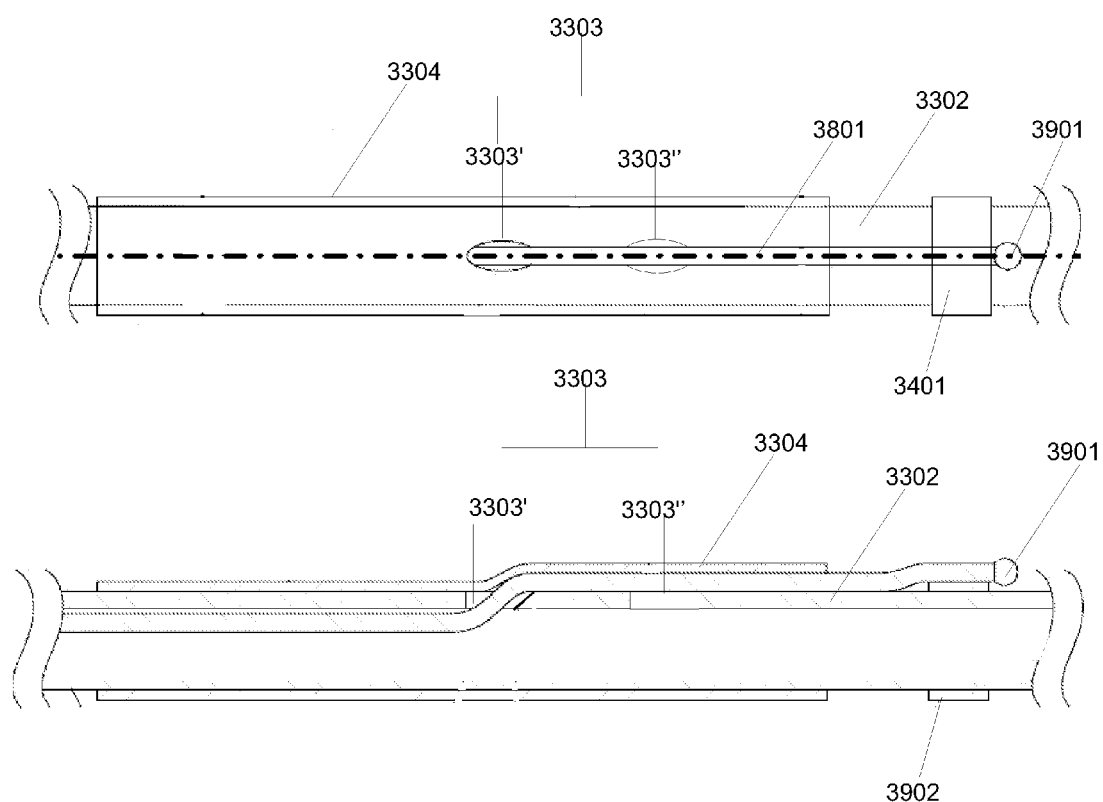
FIG. 39 illustrates a top and cross-sectional side view of an example balloon filling valve system in an open position consistent with the present disclosure

Although not shown in FIG. 33A or B, balloon spacer assembly 2802 may further include one or more radiopaque markers. Such radiopaque markers may be placed at any suitable location on or within balloon assembly 2802 so as to facilitate viewing of the assembly as it is inserted, e.g., view fluoroscopy, intracardiac echo (ICE), or another technique. In some embodiments, one or more radiopaque markers are positioned distal to valve 3303 in central tube 3302. This concept is illustrated in FIG. 39, wherein radiopaque marker 3902 is shown positioned on an outer surface of central tube 3302 distal to proximal and distal valve openings 3303', 3303". Of course, such positioning is for example only, and radiopaque markers may be placed at any suitable location on or within balloon assembly 2802, such as proximal and distal to balloon 3312.

Figure 33C:
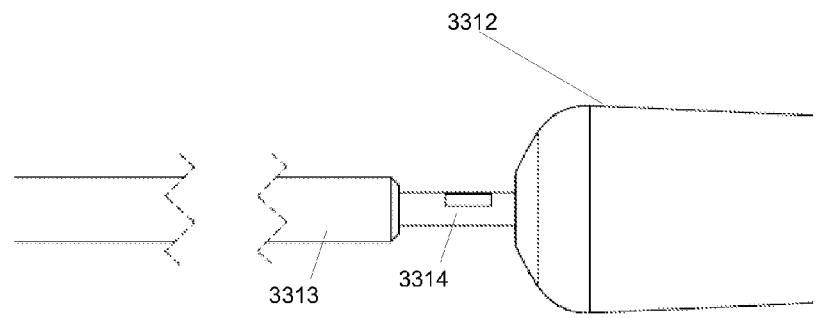
FIGS. 33C through 33E illustrates side, cross sectional, and cross sectional detail views of a balloon assembly coupled to a pusher consistent with the present disclosure.
Figure 33D:
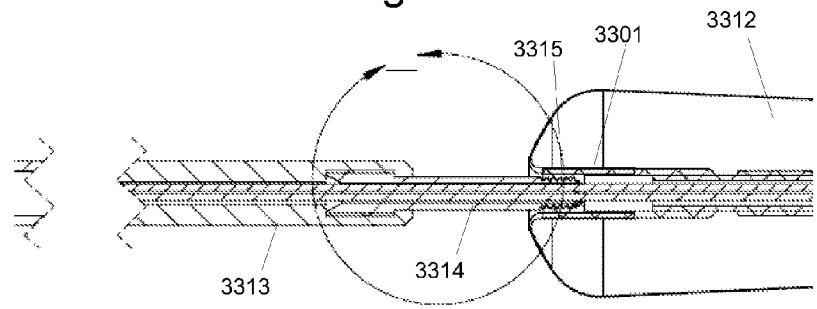
Figure 33E:
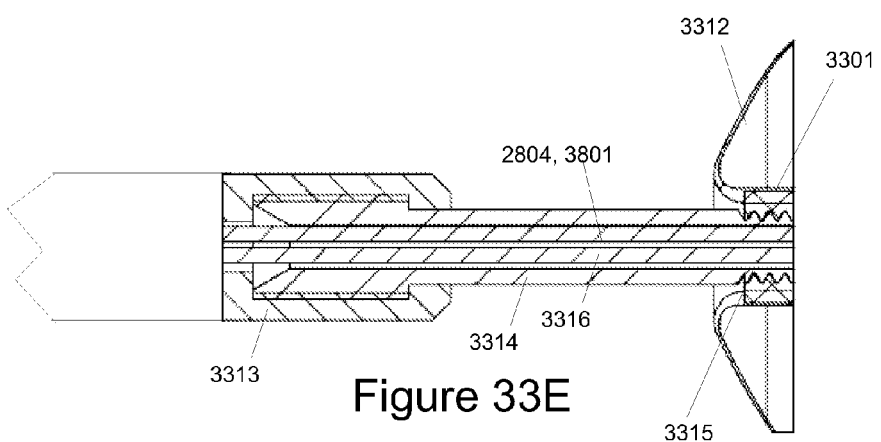

The components illustrated in FIG. 33A may be assembled as discussed above to form a unitary balloon spacer assembly 2802 of the general configuration shown in FIG. 33B. Once assembled, balloon spacer assembly 2802 may be coupled to a delivery catheter, such as the pusher catheter 3313 illustrated in FIGS. 33C-33E. In this regard, proximal end cap 3301 of balloon spacer assembly 2802 may be configured to mechanically engage coupling 3314 located at a distal end of pusher catheter 3313, as generally shown in FIGS. 33C-33E. Any type of mechanical coupling may be used to couple coupling 3314 of pusher catheter 3313 to proximal end cap 3301, provided that such mechanical coupling may enable coupling 3314 to be decoupled from proximal end cap 3301 when balloon spacer assembly 2802 is deployed in a heart.

Without limitation, proximal end cap 3301 and coupling 3314 are preferably configured to threadably engage one another so as to retain balloon assembly 2802 on a distal portion of pusher catheter 3313. This concept is illustrated in FIGS. 33D and 33E, wherein proximal end cap 3301 is illustrated as including threads 3315 on an inner surface of its lumen. In this embodiment, threads 3315 may be configured to threadably engage corresponding threads on a distal outer portion of coupling 3314. Coupling and decoupling of balloon spacer assembly 2802 may therefore be performed by rotating pusher catheter 3313 (and hence coupling 3314) to engage and disengage threads 3315 of proximal end cap 3301.

In addition to the foregoing features pusher catheter 3313 (including coupling 3314) may include a lumen extending from a proximal portion thereof to a distal portion thereof. The lumen may be sized appropriate to permit a delivery guide wire (e.g., delivery guide wire 2804) and a valve wire (e.g., valve wire 3801) to be freely disposed therein. This concept is generally shown in FIG. 33E, wherein pusher catheter 3313 and coupling 3314 are illustrated as including a lumen 3316 in a central portion thereof, with delivery guide wire 2804 and valve wire 3801 extending proximally there through.

In addition to hosting delivery guide wire 2804 and valve wire 3801, lumen 3316 of pusher catheter 3316 may facilitate the inflation and/or deflation of balloon 3312 of balloon spacer assembly 2802. In this regard, a proximal portion (not shown) of pusher catheter 3313 may be fluidly coupled to a source of fluid, such as a saline reservoir. Prior to insertion of balloon assembly 2802 into a lumen of steerable catheter 200, balloon 3312 may be subject to a de-airing process. The purpose of the de-airing process is to remove air from the internal chamber of balloon 3312 prior to implantation, so as to avoid or lessen the risk of introducing a dangerous air embolism into the vasculature of a patient, e.g., in the event that balloon 3312 may leak or be structurally compromised during or after implantation. In this regard, balloon 3312 may be repeated filled with and drained of fluid, e.g., by the introduction and withdrawal of fluid (e.g., saline) through lumen 3316 from a fluid source coupled to a proximal portion of pusher catheter 3313.

Once balloon 3312 is de-aired, balloon spacer assembly 2802 (coupled to distal end of pusher catheter 3313) may be inserted into the lumen of steerable catheter 200 and advanced (e.g., pushed) through the lumen of steerable catheter 200 with pusher catheter 3313. During this process, delivery guide wire 2804 and valve wire 3901 may be disposed through the lumens of the respective components of balloon assembly 2802, such that they extend through the entire assembly as generally shown in FIGS. 33B-33E. Pusher catheter 3313 may therefore be configured to have sufficient flexibility to navigate and push balloon spacer assembly 2802 through the route defined by the lumen of steerable catheter 200 and along delivery guide wire 2804 and valve wire 3901. In this regard, pusher catheter may be formed from any suitable biocompatible material, such as a biocompatible polymeric material, including but not limited to those specified as suitable for use in an anchor delivery catheter. In this way, balloon assembly 2802 may be delivered through the lumen of steerable catheter 200 to a position proximate to anchor assembly 2801 within the heart of a patient.

With reference to FIGS. 34A-34E, balloon assembly 2802 at this point may be urged by pusher catheter 3313 forward such that a distal end of balloon assembly 2802 (e.g., pledget support 3310, a distal end of the latch assembly (e.g., distal plug 3309) contacts and receives latch plug 2906 of anchor assembly 2801 in a lumen thereof. In this regard, the lumen in a distal end of the latch assembly (e.g., in distal plug 3309) may be configured to receive a proximal end of latch plug 2906 therein. Alignment of the lumen in distal plug 3309 and the proximal end of latch plug 2906 may be facilitated by delivery guide wire 2804, which is coupled to the proximal end of latch plug 2906 and extends through all of the respective lumens of the various components of balloon spacer assembly 2802.

Figure 34A:
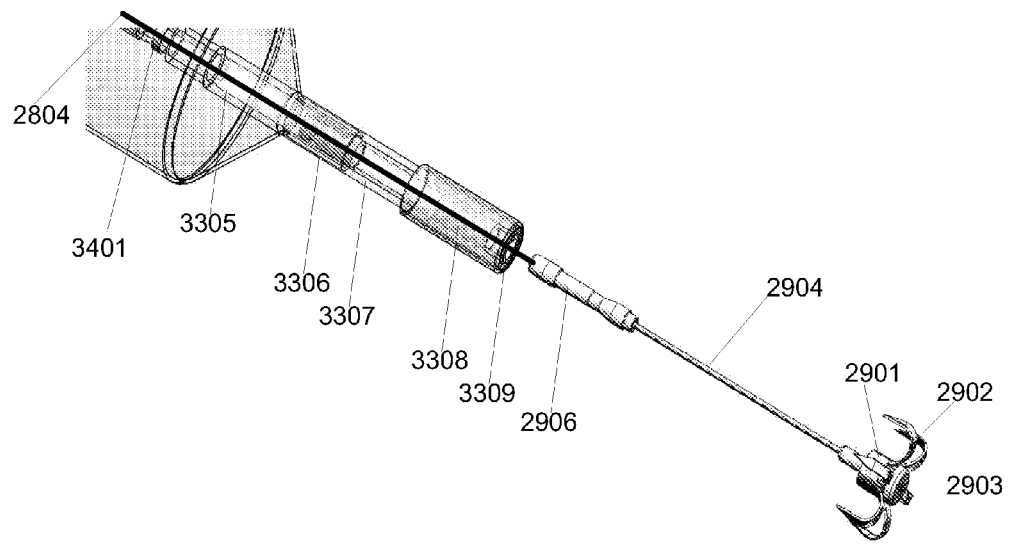
FIGS. 34A-34E illustrate an example of the coupling of a balloon assembly and anchor assembly consistent with the present disclosure.
Figure 34B:
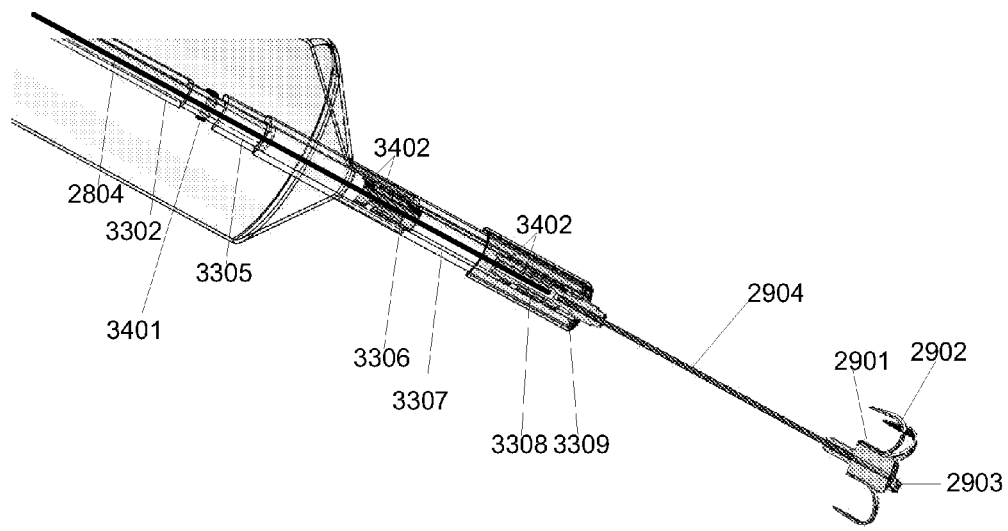
Figure 35A:
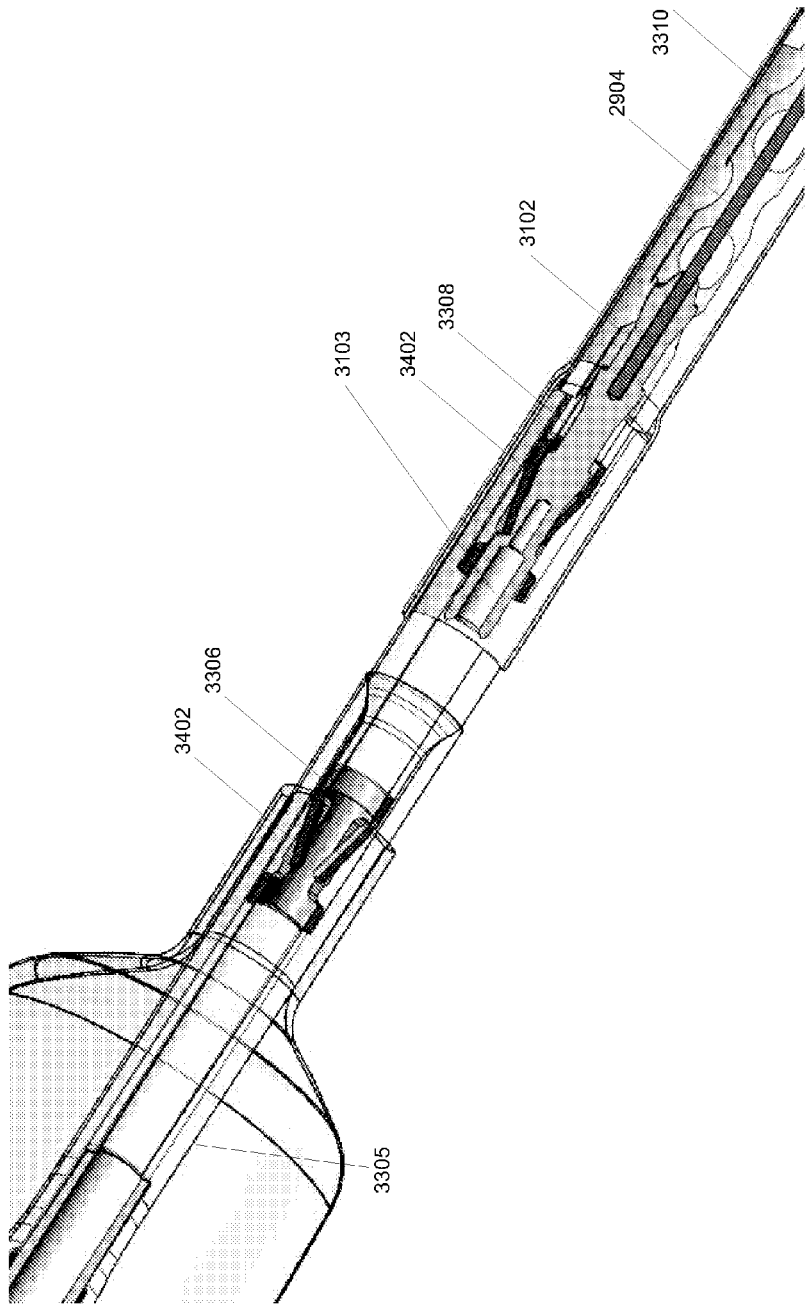
FIGS. 35A and 35B illustrate perspective views showing the interaction of latch locking elements with a latch plug consistent with the present disclosure.
Figure 35B:
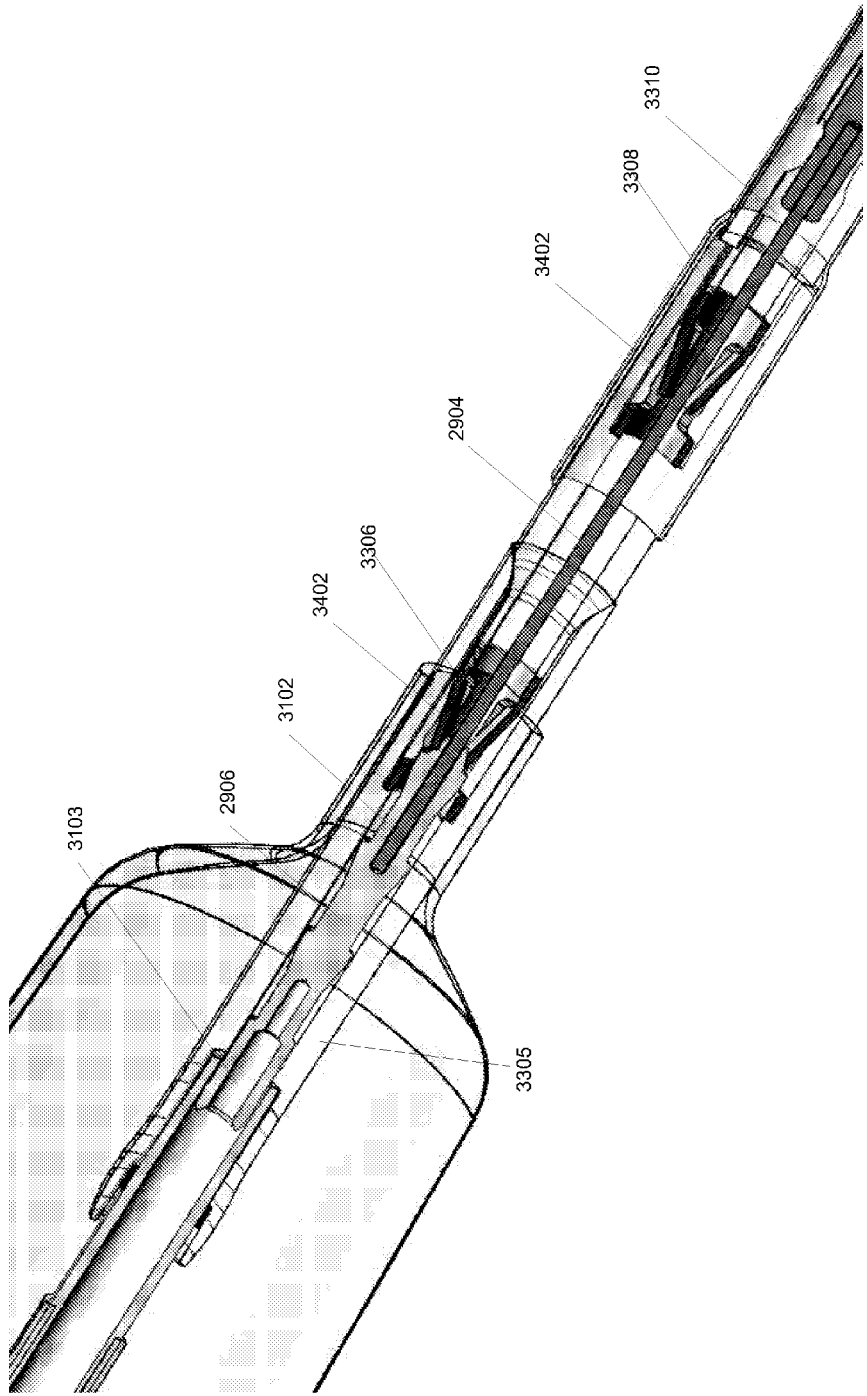

As shown in FIG. 34B, balloon assembly 2802 may be further urged forward by pusher catheter 3313 such that latch plug 2906 moves proximally through the lumen of distal plug 3309 and mechanically engages locking elements 3402 of distal latch 3308. More specifically, and with reference to FIGS. 35A and 35B, proximal and distal latches 3306 and 3308 may include one or more locking elements 3402 that may resiliently deform to receive and sealingly engage latch plug 2906 of anchor assembly 2801. More specifically, proximal and distal latches 3306 and 3308 may include locking elements in the form of one or more resiliently deformable locking arms (e.g., pawls, not labeled), as generally illustrated in FIGS. 35A and 35B. As balloon spacer assembly 2802 is urged against latch plug 2906, a proximal contoured portion of latch plug 2906 (e.g., contoured portion 2907 in FIG. 29) may contact locking element(s) 3402 of distal latch 3308, e.g., one or more resiliently deformable locking arms.

With the application of sufficient force by pusher catheter 3313, the proximal contoured portion 2907 of latch plug 2906 may resiliently deform locking element(s) 3402 of distal latch 3308 outwards. The proximal contoured portion 2907 and latch plug 2906 may then advance proximally past locking element(s) 3402 of distal latch 3308. Upon sufficient travel of latch plug 2906, locking element(s) may then return to their initial position and lock behind a ridge of latch plug 2906 distal to the proximal contoured portion, e.g., ridge 2908 shown in FIG. 29. This may lock latch plug 2906 in between the initial proximal contoured portion 2907 and a medial contoured portion 2907' of latch plug 2906. This concept is shown in FIGS. 34B and 35A, wherein locking element(s) 3402 of distal latch 3308 is/are in the form of resiliently deformable locking arms that are position to engage a ridge (2908) of latch plug 2906 after latch plug 2906 has partially moved through distal latch 3308.

In addition to the foregoing, the contoured portions of latch plug 2906 may be configured to engage with corresponding interior features of the lumens in elements 3305-3308 of the balloon assembly 2802. In this way, latch plug 2906 may form a fluid tight seal with the interior features of such lumens, thus creating a fluid seal proximate to distal end of balloon 3312. This seal may facilitate filling of balloon 3312 with a fluid, as discussed generally below.

Figure 34C:
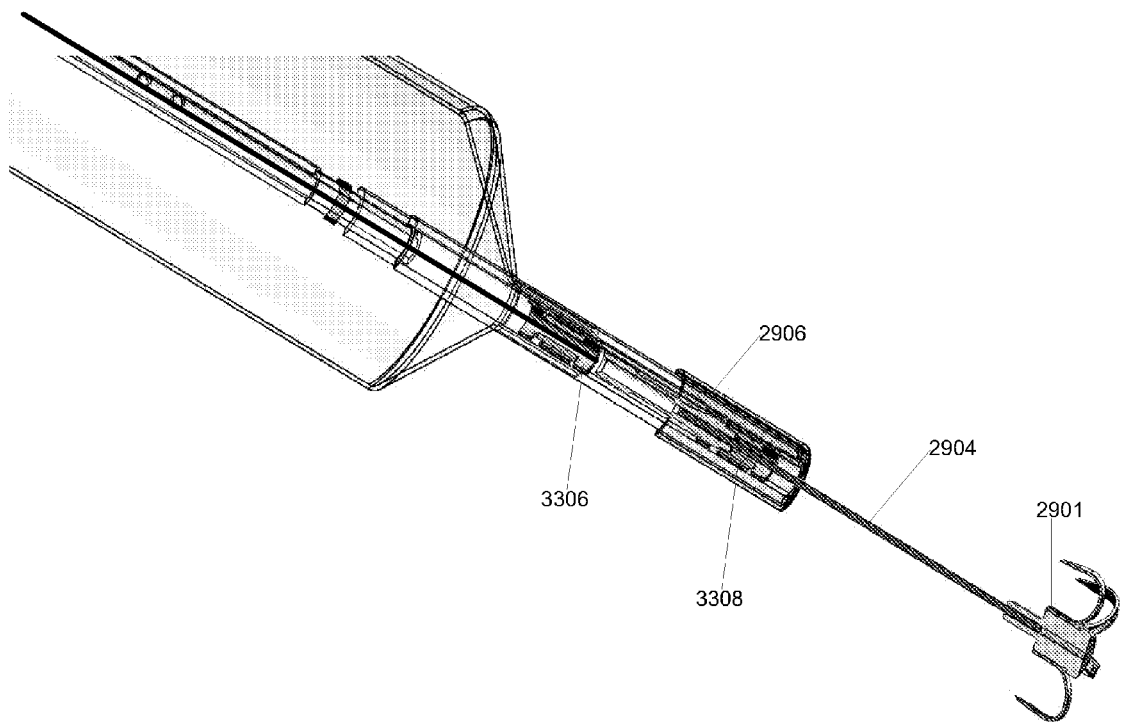
Figure 34D:
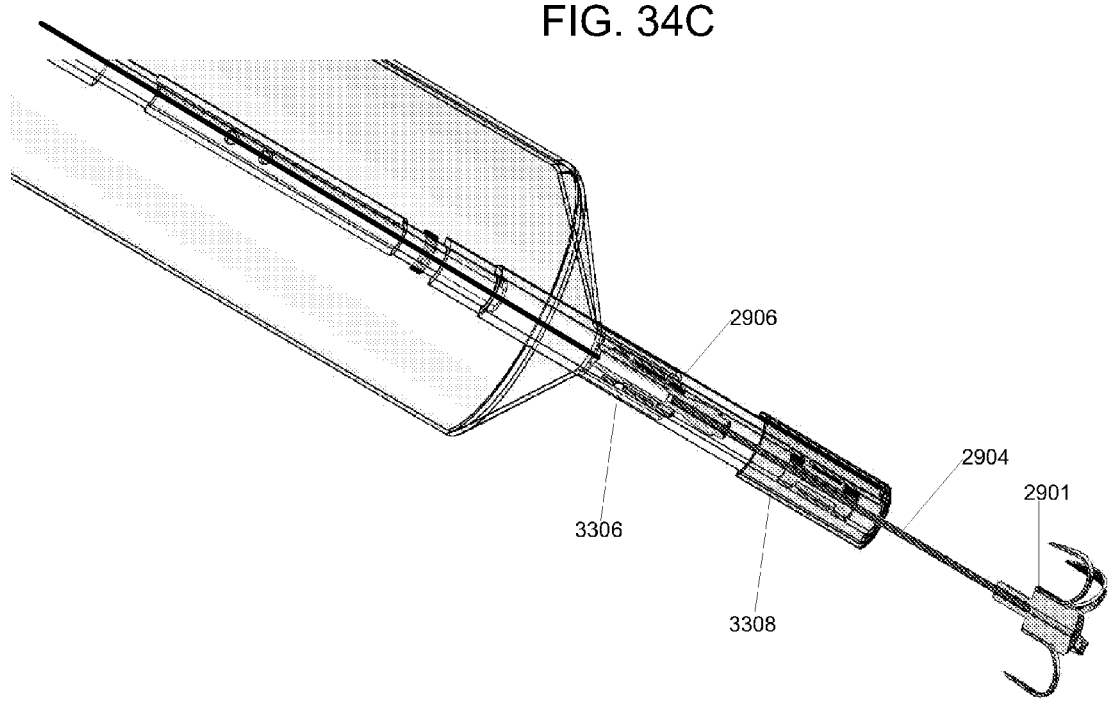

As may be appreciated, locking element(s) 3402 may permit further proximal movement (e.g., to shorten heart valve implant 2800), but may inhibit of prevent distal movement of the anchor assembly 2801 from the balloon assembly after locking elements 3402 have engaged a ridge of latch plug 2906. This concept is shown in FIGS. 34C, D, and E, wherein in response to further urging by pusher catheter 3313, latch plug 2906 further advances proximally through distal latch 3308 by resiliently deforming locking element(s) 3402 thereof. In this regard, latch plug 2906 may be configured to include multiple contoured and ridge portions, which may define several locking zones that may engage and lock with locking elements 3402 of proximal and/or distal latches 3306, 3308.

This concept is shown in FIG. 29, wherein latch plug is depicted as including multiple contoured regions (2907, 2907', 2907") and multiple corresponding ridges (2908, 2908', 2908"). As latch plug 2906 is advanced proximally through proximal and distal latches 3306, 3308, locking element(s) 3402 of such latches may be resiliently deformed by contoured regions (2907, 2907', 2907") of latch plug 2906. With the passage of each contoured region, locking element(s) 3402 may spring back and engage with a corresponding ridge (2908, 2908', 2908"), thus hindering or preventing distal movement of anchor assembly 2801. This concept is illustrated in FIG. 35B, wherein latch plug 2906 is depicted as having been advanced proximally through distal latch 3308 and proximal latch 3306 such that locking element(s) 3402 of proximal latch 3306 engage a distal ridge (not labeled) of latch plug 2906.

Figure 34E:
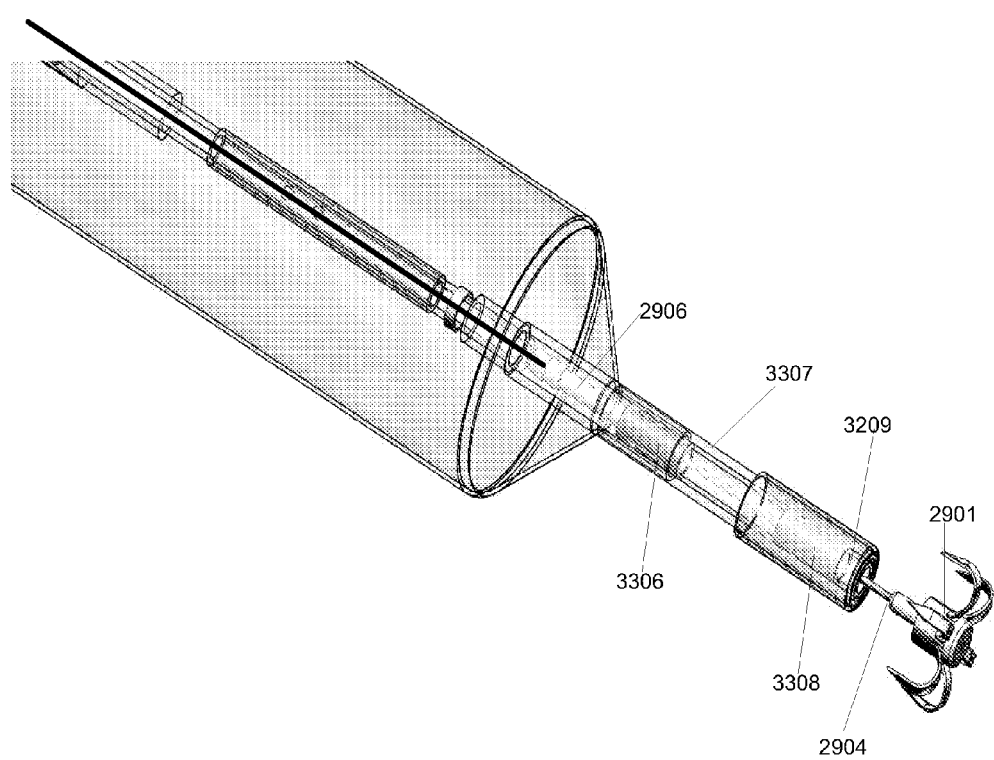

In this way, the features of latch plug 2906 and proximal and/or distal latches 3306, 3308 may enable one way adjustment of the length of heart valve implant 2800 within the heart of a patient. This concept is generally shown in FIGS. 34A-34E, which illustrate the initial coupling of balloon spacer assembly 2802 with anchor assembly 2801 and subsequent length adjustments from a maximum length (FIG. 34B) to a minimum length (FIG. 34E). This feature may be useful to adjust the length of heart valve implant to account for patient anatomy, etiology of the valve defect the heart valve implant is being used to address, or for some other reason.

As generally described above, various features of the balloon assembly and anchor assembly described herein may enable one way adjustment (i.e., shortening) of the length of a heart valve implant. Although useful, it may be desired in some instances to reverse the shortening of a heart valve implant consistent with the present disclosure. As noted previously, two way length adjustment capabilities may be achieved by forming proximal and distal latches of a body temperature activated shape memory alloy, such as a body temperature activated nitinol. In such instances, locking element(s) 3402 may be configured at body temperature to expand and lock behind one or more ridges of a latch plug, as discussed above. However, locking of the locking element(s) 3402 in these embodiments may be reversed by adjusting the temperature of the shape memory alloy used to form the latches, including locking element(s) 3402. For example, locking elements 3402 may be configured to unlock upon exposure to a relative cold fluid that drops the temperature of locking element(s) 3402 below their transition temperature. Once opened in this fashion, latch plug 2906 may be moved distally, e.g., by pushing on delivery guide wire 2804.

Figure 36:
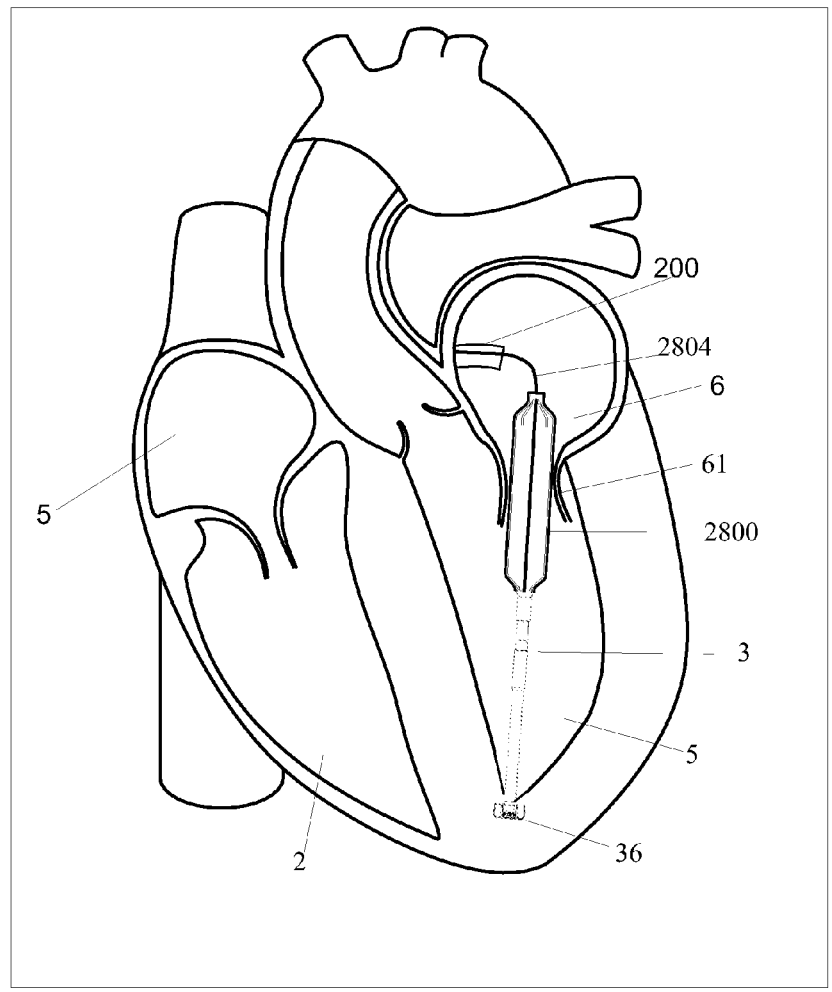
FIG. 36 illustrates an embodiment of a heart valve implant consistent with the present disclosure as implanted at an implantation site of a heart.

As described above, an anchor assembly and a balloon spacer assembly consistent with the present disclosure may each be trans-femorally delivered to an implantation site within a human heart view a lumen of a steerable catheter. Once the anchor assembly is engaged with native coronary tissue, the balloon spacer assembly may be delivered and coupled to the anchor assembly within the heart as described above. The length of the resulting heart valve implant may then be adjusted as previously described such that a balloon of the balloon spacer assembly is appropriately positioned within a heart. By way of example, the resulting heart valve implant may be positioned such that a balloon of the balloon spacer is positioned within a mitral valve 61 of a patient, as shown in FIG. 36.

As noted previously, the balloon of the balloon spacer may be de-aired prior and deflated prior to insertion into a lumen of a steerable catheter and delivery to a location proximate to an implant site within a heart. With this in mind, before or after length adjustments are performed, the balloon of the balloon spacer assembly may be inflated with an inflation medium, such as saline or another fluid. Inflation of the balloon may be performed in any suitable manner, and may cause the balloon to assume a desired shape or profile. For example, the balloon may be inflated such that it contacts or otherwise engages the leaflets of a mitral valve, thereby mitigating or eliminating excessive regurgitation there through. This concept is shown in FIG. 36, wherein heart valve implant 2800 includes a balloon (not labeled) which has been positioned and inflated such that it contacts one or more leaflets (not labeled) of mitral valve 61.

Figure 37:
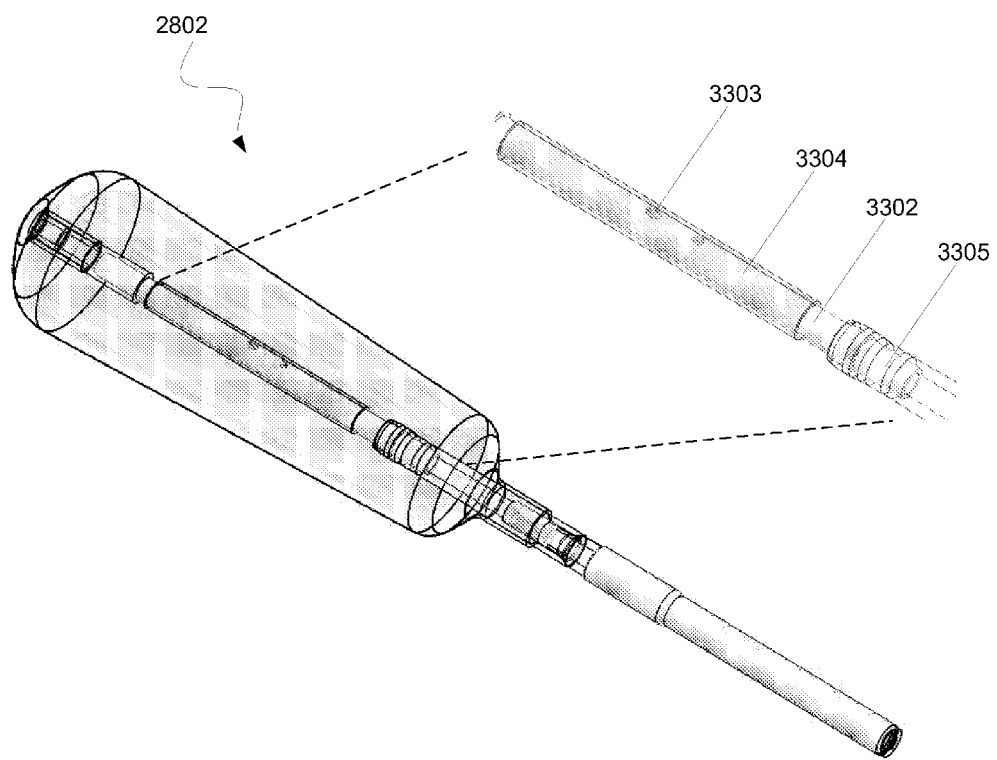
FIG. 37 illustrates a perspective view of an implant including a balloon valve system consistent with the present disclosure.
Figure 38:
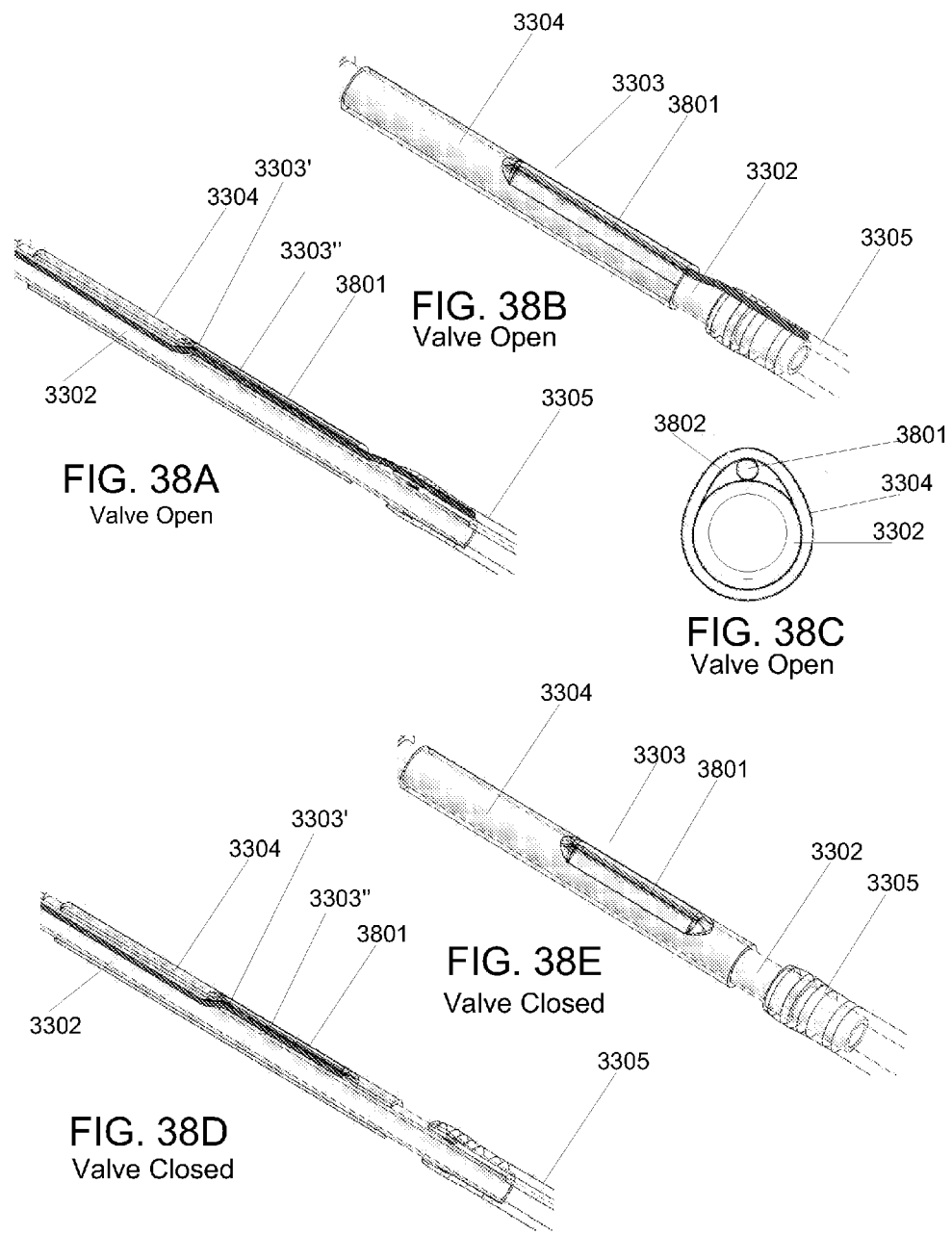
FIGS. 38A-38C illustrate cross sectional and perspective view of an example balloon valve system in an open position consistent with the present disclosure.
FIGS. 38D and 38E illustrate cross sectional and perspective views, respectively, of an example balloon valve system in a closed position consistent with the present disclosure.

As described previously in connection with FIGS. 33A-E and as highlighted in FIG. 37, balloon spacer assembly 2802 may be configured to include a central tube 3302, a valve 3303, and a valve sleeve 3304. As will be described below, these components may form in conjunction with a valve wire a balloon valve system that may control the filling and deflation of balloon 3312 of balloon assembly 2802.

In this regard, reference is made to FIGS. 38A-38E and FIG. 39, which depict various views of an example balloon valve system consistent with the present disclosure. As shown in those FIGS and explained above, the balloon valve system includes central tube 3302, valve 3303, valve sleeve 3304, and valve wire 3801. As shown in FIG. 33B, these components may be disposed within balloon 3313 of balloon assembly 2802. Valve wire 3801 may be made of any suitable material, such as a metal, metal alloy (e.g., nitinol, stainless steel, etc.), or the like. In some embodiments, valve wire 3801 is in the form of a braided metal wire, such as a braided stainless steel or nitinol wire.

Turning now to FIGS. 38A-38C, and 39, an example balloon valve system in an open position is illustrated. As shown, valve 3303 includes proximal and distal openings 3303', 3303'' formed through an outer wall of central tube 3302, so as to provide access to and from a lumen and exterior of central tube 3302. Proximal opening 3303' is generally configured to receive valve wire 3801 there through and to facilitate the proximal and distal movement of valve wire 3801 beneath valve sleeve 3304. In this regard, proximal opening 3303' may be contoured or angled so as to ease or facilitate the transition of valve wire 3801 from within a lumen of central tube 3302 to a region between the exterior of central tube 3302 and valve sleeve 3304. For example, all or a portion of the distal circumference of proximal opening 3303' may be graded and/or angled from about 15 to about 45 degrees, such as about 15 to about 30 degrees, or even about 15 to about 25 degrees.

To facilitate movement and or other functions, valve wire 3801 may be configured to include a blunt tip. This concept is illustrated in FIG. 39, wherein valve wire 3801 is illustrated as including a blunt tip 3901 in the form of a ball at a distal end thereof. Of course, valve wire 3801 need not have a spherical or ball shaped tip. Indeed, valve wire 3801 may be capped with a blunt tip of any suitable geometry. In some embodiments, blunt tip 3901 may be configured to facilitate movement between valve sleeve 3304 and central tube 3302. For example, blunt tip 3901 may be configured to allow valve wire 3801 to slide between valve sleeve 3304 and central tube 3302 without scratching or otherwise marring the exterior of central tube 3302.

In any case, valve wire 3801 may be advanced through proximal opening 3303' and beneath valve sleeve 3304, as generally illustrated. As it moves between valve sleeve 3304 and an exterior of central tube 3302, valve wire 3801 may cause valve sleeve 3304 to deform and "tent," as shown in FIG. 38C. This may cause one or more openings 3802 to form between the outer portion of central tube 3302, valve wire 3801, and valve sleeve 3304. If valve wire 3801 is advanced sufficiently such that its distal tip emerges from underneath valve sleeve 3304, openings 3802 may extend from distal opening 3303'' and potentially proximal opening 3303' to an exterior of central tube 3302 and an interior of balloon 3312.

With valve wire 3801 in the position shown in FIGS. 38A, 38B and 39, balloon 3312 may be filled by conveying a filling medium such as saline through a lumen of pusher 3313, which is coupled to a proximal end cap 3301 of balloon assembly 2802. The fluid may flow from the lumen of pusher 3313 through the lumen of proximal end cap 3301, through the lumen of central tube 3302, through proximal and/or distal openings 3303', 3303'', through opening(s) 3802, and into balloon 3312. Withdrawal of the filling medium from balloon 3312 may also be achieved with the valve wire 3801 in this position, e.g., by applying suction or another withdrawing force to the lumen of the steerable catheter.

The balloon valve system may be closed by partially or fully withdrawing valve wire 3801, i.e., by retracting the distal end of valve wire 3801 beneath a distal edge of valve sleeve 3304. To illustrate this concept, reference is made to FIGS. 38D and 38E, wherein a balloon valve system in a closed position is depicted. As shown in these FIGS., valve wire 3801 has been retracted such that its distal end is underneath the distal edge of valve sheath 3304. Although not shown, sufficient retraction of valve wire 3801 may have the effect of closing openings 3802 that may be present when valve wire 3801 is extended to or past the distal edge of valve sheath 3304. This is because valve sheath 3304 may be formed of a resiliently deformable material that may snugly envelope the outer surface of central tube 3302 when valve wire 3801 is retracted. In other words, valve sheath 3304 may upon retraction of valve wire 3801 snugly engage the outer surface of central tube 3302 and form a fluid tight seal, thus preventing fluid from entering or exiting balloon 3312.

As shown in FIGS. 38D and E, the balloon valve system may be closed without fully withdrawing valve wire 3801. That is, the balloon valve system may be closed by retracting valve wire 3801 such that its distal tip is between proximal opening 3303' and the distal edge of valve sleeve 3304. In this position, the balloon valve system is closed, and the balloon may be observed and or tested to determine whether it is filled to a desired degree. If adjustment to filling of the balloon is desired, valve wire 3801 may be advanced distally to create openings 3802, through which fluid may be added or removed. Once the balloon is filled to a desired degree, the valve system may be permanently or semi permanently locked by withdrawing valve wire 3801 through proximal opening 3303', and ultimately out of the lumen of pusher 3313.

At this point, an inflated heart valve implant has been implanted into a heart of the patient. However, the heart valve implant may remain coupled to delivery guide with 2804 and/or pusher 3313. Delivery guide wire 2804 may be detached by applying rotational or torsional force. Such force (s) may cause guide wire 2804 to threadably decouple from guide wire receive portion 3103 of latch plug 2906. Once decoupled, guide wire 2804 may be retracted through the lumens of the heart valve implant components and pusher 3313.

Pusher 3313 may then be decoupled from the proximal end of balloon assembly 2802. For example, where pusher 3313 includes a coupling 3314 that is threadably engaged with proximal end cap 3301 of a balloon assembly, the pusher may be disengaged by applying rotational and/or torsional force to the pusher. Such force (s) may cause coupling 3314 to rotate and threadably disengage from proximal end cap 3301. Once decoupled, the pusher may be withdrawn though the lumen of the steerable catheter. At this point, heart valve implant 2800 is free of connections and may be considered fully implanted in a heart.

Once the heart valve implant has been implanted, the steerable catheter 200 may be removed from the left ventricle 3 and ultimately from the heart 1 and the patient's body. According to one embodiment, the steerable catheter 200 may be removed by urging the steerable catheter 200 proximally (i.e., away from the left ventricle 3). The first steering actuator 210 may be used to minimize the force applied against the implant 110 by the steerable catheter 200 as the implant 110 exits the lumen 202 of the steerable catheter 200. If the force applied to the implant 110 by the steerable catheter 200 as the implant 110 exits the lumen 202 of the steerable catheter 200 is too great, damage may occur to the heart 1 proximate to the implant site and/or the implant 110 may be accidentally pulled out and/or disconnected from the tissue.

According to one embodiment, the force applied to the implant 110 by the steerable catheter 200 as the implant 110 exits the lumen 202 of the steerable catheter 200 may be further reduced with the aid of the second or more steerable actuators 212. For example, turning to FIGS. 40-42, one embodiment generally illustrating the deflection withdrawal sequence of a steerable catheter 200 having at least a first and a second steerable actuator 210, 212 is shown. FIG. 40 generally illustrates one embodiment of the steerable catheter 200. The implant 110 (not shown) has been secured to the tissue. The second steerable actuator 212 is illustrated in the "straight" position (i.e., the second steerable actuator 212 is not urging the shaft 206 of the steerable catheter 200). The region 240 between the second steerable actuator 212 and the first steerable actuator 210 (for example, but not limited, the distal most 3 inches of the shaft 206) is over the implant 110 from the apex 36 of the left ventricle 3 up to the mitral valve 61. The first steerable actuator 210 is in the bent or curved position to deflect the shaft 206 in order to accommodate the curve or bend from the mitral valve 60, through the transseptal puncture site 13, and into the right atrium 5.

As the steerable catheter 200 is withdrawn from the left ventricle 3, the region 240 of the steerable catheter 200 may start to encounter the curvature in the left atrium 6 between the mitral valve 61 and the transseptal puncture site 13. In order to accommodate this curvature, the second actuation device 212 may be actuated to deflect the region 240 of the shaft 206 of the steerable catheter 200 as generally illustrated in FIG. 41. Deflecting the region 240 of the shaft 206 may reduce drag of the steerable catheter 200 on the implant 110 and may also reduce the likelihood of dislodging the implant 110 from the tissue. While deflecting the region 240, the user may also un-bend the region 242 of the shaft 206 as the region 242 is moving through the transseptal puncture site 13 and into a region of reduced curvature. As the steerable catheter 200 is further removed, the second actuation device 212 may be un-bent to un-bend the region 240 of the shaft 206 as it moves through the transseptal puncture site 13 as generally illustrated in FIG. 42. At this point, both regions 240, 242 of the shaft 206 may be somewhat curved passively by the anatomy alone.

As mentioned above, the present disclosure is not intended to be limited to an apparatus, system or method which must satisfy one or more of any stated or implied object or feature of the present disclosure and should not be limited to the preferred, exemplary, or primary embodiment(s) described herein. The foregoing description of the present disclosure has been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the present disclosure and its practical application to thereby enable one of ordinary skill in the art to utilize the present disclosure in various embodiments and with various modifications as is suited to the particular use contemplated. All such modifications and variations are within the scope of the present disclosure when interpreted in accordance with breadth to which it is fairly, legally and equitably entitled.

What is claimed is:
1. An implant, comprising:
a balloon spacer assembly, the balloon spacer assembly comprising:
a balloon spacer defining a spacer cavity configured to be expanded from a deflated condition to an expanded condition with a filling fluid; and
a balloon filling valve disposed within and fluidly coupled to said spacer cavity,
wherein said balloon filling valve is configured to be fluidly coupled to a source of said filling fluid and to selectively allow the introduction and withdrawal of said fluid into and out of said spacer cavity;
wherein said balloon filling valve comprises a valve sheath, a valve wire, and a central tube comprising a lumen, an outer wall including a proximal opening and a distal opening there through;
the central tube coupled to a proximal and distal portion of said balloon spacer such that said spacer cavity is defined around said central tube;
the valve sheath disposed around said central tube, the valve sheath configured to resiliently engage an outer surface of said central tube; and
the valve wire extending through said proximal opening and comprising a tip, the valve wire configured to selectively seal and unseal said balloon filling valve depending on the location of the tip relative to a distal edge of said valve sheath.

2. The implant of claim 1, wherein said valve wire extends from an interior of said lumen of said central tube through said proximal opening, and between said valve sheath and said outer surface of said central tube.

3. The implant of claim 2, wherein said valve wire is configured to open said valve by causing the formation of an opening between said valve sheath and said outer surface of said central tube as the tip of said valve wire is distally moved relative to said proximal opening.

4. The implant of claim 3, wherein said valve is configured to close when said valve wire is sufficiently retracted under the distal edge of said valve sheath such that said valve sheath resiliently deforms to seal said opening.

5. The implant of claim 1, wherein at least a portion of said proximal opening is tapered to an angle ranging from about 15 to about 45 degrees.

6. The implant of claim 1, wherein said balloon assembly further comprises a proximal end cap coupled to said balloon spacer and said central tube, said proximal end cap including a lumen that is at least partially threaded with threads configured to threadably engage a distal end of a pusher catheter.

7. The implant of claim 1, wherein said balloon assembly further comprises a latching mechanism coupled to a distal end of said balloon filling valve, said latching mechanism configured to mechanically engage a proximal portion of an anchor assembly; wherein said latching mechanism comprises at least one latch, said at least one latch comprising a resiliently deformable locking element that is configured to resiliently deform outwards in response to an application of force from said proximal portion of said anchor assembly.

8. The implant of claim 7, wherein said proximal portion of said anchor assembly comprises a latch plug, said latch plug comprising a contoured region for resiliently deforming said locking element and a ridge distal to said contoured region.

9. The implant of claim 7, wherein said resilient deformable locking element is configured to:
    resiliently deform outwards in response to an application of force from a contoured region of a latch plug, thereby permitting said latch plug to move proximally; and
    mechanically engage and lock behind a ridge of said latch plug once said contoured region has proximally moved past said resiliently deformable locking element.

10. The implant of claim 7, wherein said proximal portion of said anchor assembly comprises:
    a latch plug comprising a plurality of contoured regions and a corresponding plurality of ridges;
    each of said plurality of contoured regions is configured to resiliently deform said locking element outward to permit proximal movement of said latch plug through said latch; and
    said locking element is configured to mechanically engage and lock behind each of said ridges of said latch plug once a corresponding contoured region has proximally moved past said locking element.

* * * * *